/

US005804379A

United States Patent [19]

Lee et al.

[11] Patent Number: 5,804,379
[45] Date of Patent: *Sep. 8, 1998

[54] DIAGNOSTIC METHODS AND KIT FOR DETERMINING KELL BLOOD GROUP GENOTYPE

[75] Inventors: Soohee Lee, Cliffside Park, N.J.; Colvin M. Redman, Franklin Square, N.Y.

[73] Assignee: New York Blood Center, Inc., New York, N.Y.

[ * ] Notice: The term of this patent shall not extend beyond the expiration date of Pat. No. 5,589,336.

[21] Appl. No.: 484,570

[22] Filed: Jun. 7, 1995

Related U.S. Application Data

[63] Continuation-in-part of Ser. No. 337,268, Nov. 10, 1994, Pat. No. 5,589,336.

[51] Int. Cl.$^6$ .............................. C12Q 1/68; C12P 19/34; C07H 21/02; C07K 5/00
[52] U.S. Cl. .................................. 435/6; 435/12; 435/71; 435/240.27; 435/252.1; 435/69.1; 424/22; 530/300; 530/388.1; 536/23.1; 536/24.3; 536/24.33
[58] Field of Search .................................. 435/6, 5, 91.2, 435/7.1–7.9, 240.27, 252.1, 172.3, 69.1; 530/300, 388.1; 424/22; 536/23.1, 24.3, 24.33

[56] References Cited

U.S. PATENT DOCUMENTS

| | | |
|---|---|---|
| 4,148,607 | 4/1979 | Bernoco et al. . |
| 4,358,436 | 11/1982 | Graham, Jr. et al. . |
| 4,403,042 | 9/1983 | Henry et al. . |
| 4,560,647 | 12/1985 | Stocker . |
| 5,213,963 | 5/1993 | Uthemann . |
| 5,302,512 | 4/1994 | Pernelle . |
| 5,324,479 | 6/1994 | Naldoni et al. . |
| 5,589,336 | 12/1996 | Lee et al. .................................. 435/6 |

OTHER PUBLICATIONS

Berkowitz et al., "Death in utero due to Kell sensitization without excessive elevation of the $\Delta od_{450}$ value in amniotic fluid," *Obstetrics & Gynecology*, 60(6): 746–749 (1982).
Branch et al., "Disulfide bonds are a requirement of Kell and Cartwright (Yt$^a$) blood group antigen integrity," *Br. J. Haematol.* 54: 573–78 (1993).
Bowman et al., "Maternal Kell blood group alloimmunization," *Obstetrics & Gynecology*, 79(2): 239–244 (1992).
Chang et al., "Molecular characterization of erythrocyte glycophorin c variants," *The American Society of Hematology—Blood*, 77(3): 644–648 (1991).
Cherif–Zahar et al., "Organization of the gene (RHCE) encoding the human blood group RhCcEe antigens and characterization of the promoter region," *Genomics* 19: 68 (1994).
Constantine, "Anti–Kell in pregnancy," *Lancet*, 338: 198 (1991).

Constantine et al., "Anti–Kell in pregnancy," *British Journal of Obstetrics and Gynaecology*, 98: 943–944 (1991).
Cullen, "Erythroblastosis fetalis produced by Kell immunization: Dental findings," *Pediatric Dentistry*, 12(6): 393–396 (1990).
Duguid et al., "Haemolytikc disease of the newborn due to anti–k," *Vox Sang*, 58: 69 (1990).
Furuhjelm et al., "The blood group antigen U1$^a$(Karhula)," *Vox Sang*. 15: 118–24 (1968).
Giblett et al., "A critique of the theoretical hazard of inter– vs. intra–racial transfusion," *Transfusion* 1: 233 (1961).
Giblett et al., "Js$^a$ a 'new' red cell antigen found in negroes: evidence for an eleventh blood group system," *Brit J. Haematol.* 5: 319–26 (1959).
Gusdon, Jr. et al., "Amniotic fluid analysis in erythroblastosis secondary to Kell immunization," *Obstetrics and Gynecology*, 33(3): 432–434 (1969).
Hardie et al., "Neuroacanthocytosis—a clinical, haematological and pathological study of 19 cases," *Oxford University Press—Brain*, 114: 13–44 (1991).
Jaber et al., "Characterization of murine monoclonal antibodies directed against the Kell blood group glycoprotein," *British Journal of Haematology*, 79: 311–315 (1991).
Jaber et al., "Characterization of the blood group Kell (k1) antigen with a human monoclonal antibody," *Blood*, 73(6): 1597–1602 (1989).
Lee et al., "The human Kell blood group gene maps to chromosome 7q33 and its expression is restricted to erythroid cells," *The American Society of Hematology—Blood*, 81(10): 2804–2809 (1993).
Lee et al., "Molecular cloning and primary structure of Kell blood group protein," *Proc. Natl. Acad. Sci. USA*, 88: 6353–6357 (1991).
Leggat et al., "Anti–Kell in pregnancy," *British Journal of Obstetrics and Gynaecology*, 98: 162–165 (1991).
Marsh et al., "Blood groups of human red cells in clinical practice of blood transfusion," (Petz et al. eds.) pp. 79–130, Churchill–Livingstone, New York (1981).
Marsh et al., "Recent developments in the Kell blood group system," *Transfusion Medicine Reviews*, 1(1): 4–20 (1987).
Marsh et al., "The Kell blood group system: a review," *Transfusion*, 30(2): 158–167 (1990).

(List continued on next page.)

*Primary Examiner*—W. Gary Jones
*Assistant Examiner*—Jeffrey Fredman
*Attorney, Agent, or Firm*—Hoffmann & Baron, LLP

[57] ABSTRACT

The invention provides a diagnostic method of determining Kell genotype by the identification of the molecular basis of a Kell polymorphism. Specifically, the invention provides a method for determining K1/K2 genotype with great accuracy, overcoming problems associated with traditional serological typing methods. The diagnostic method of the invention preferably employs amplification of K1/K2 nucleic acid sequences, and optionally employs differential cleavage of K1- and K2-specific nucleic acid sequences by a restriction enzyme. Also provided are nucleic acid oligomers useful as probes or primers for the method of the invention. Furthermore, diagnostic kits for the determination of Kell genotype are provided.

75 Claims, 31 Drawing Sheets

OTHER PUBLICATIONS

Mayne et al., "The significance of anti–Kell sensitization in pregnancy," *Clin. Lab. Haemat.,* 12: 379–385 (1990).

Moncharmont et al., "A case of hemolytic disease of the newborn infant due to anti–k (cellano)," *Acta Haematol,* 85: 45–46 (1991).

Murphy et al., "Regional chromosomal assignment of the Kell blood group locus (kel) to chromosome 7q33–q35 by fluorescence in situ hybridization: evidence for the polypeptide nature of antigenic variation," *Human Genetics,* 91: 585–588 (1993).

Parsons et al., "Monoclonal antibodies against Kell glycoprotein: serology, imunochemistry and quantification of antigen sites," *Transfusion Medicine,* 3: 1–6 (1993).

Petty et al., "Application of the maiea assay to the Kell blood group system," *Vox Sang,* 66: 216–224 (1994).

Purohit et al., "The Kell blood group locus is close to the cystic fibrosis locus on chromosome 7," *Human Genetics,* 89: 457–458 (1992).

Redman et al., "Kell blood group antigens are part of a 93,000–Dalton red cell membrane protein*," *The Journal of Biological Chemistry,* 261(20): 9521–9525 (1986).

Redman et al., "Comparison of human and chimpanzee Kell blood group systems," *Transfusion,* 29(6): 486–490 (1989).

Redman et al., "Isolation of Kell–active protein from the red cell membrane," *Transfusion,* 24(2): 176–178 (1984).

Redman et al., "The Kell antigens and McLeod red cells:" 53–69.

Redman et al., "The Kell blood group system and the McLeod phenotype," *Seminars in Hematology,* 30(3): 209–218 (1993).

Telen et al., "Erythrocyte webb–type glycophorin c variant lacks n–glycosylation due to an asparagine to serine substitution," *American Journal of Hematology,* 37: 51–52 (1991).

Vaughn et al., "Anti–Kell in pregnancy," *Lancet,* 338: 199 (1991).

Wallas et al., "Isolation of a Kell–reactive protein from red cell membrane," *Transfusion,* 26(2): 173–175 (1986).

Zelinski et al., "Genetic Linkage between the Kell blood group system and prolactin–inducible protein loci: Provisional assignment of kel to chromosome 7," *Human Genetics,* 55: 137–140 (1991).

Zelinski, "The use of dna restriction fragment length polymorphisms in conjunction with blood group serology," *Transfusion,* 31(8): 762–770 (1991).

FIG-2A

EXON 1
1-123

(SEQ ID NO:37)

```
                                                ......GAAGTGCCCCTTCTCTCCAGGATCAAGGAA     28
29   CTGGGGCGGGGGGTGTTTCCTGGACCCCCAGTCCTCCGAATCAGCTCCTAGAGTGGAACC                        87
                                                                Met
88   AGGAAGGATTCTGGAGCCACAGAAGATAGACAG ATG gtaagtccccttttggagtcagagg.....0.34kb
```

FIG-2B

EXON 2 (SEQ ID NO:38)
124-201

```
                                                       Glu Gly Gly   4
              ctccttctccctccactcacttcag                GAA GGT GGG 132

Asp Gln Ser Glu Glu Glu Pro Arg Glu Arg Ser Gln Ala Gly Gly  19
  5   GAC CAA AGT GAG GAA GAG CCG AGG GAA CGC AGC CAG GCA GGT GGA 177
133

Met Gly Thr Leu Trp Ser Gln Glu
 20   ATG GGA ACT CTC TGG AGC CAA GAG gtaagtgccctcctcctcctggtct.....0.29kb
178
```

FIG-2C

EXON 3
202-343

(SEQ ID NO:39)

```
                                        Ser Thr Pro Glu Glu Arg Leu    34
         tttcacctcttggttcctcccacag      AGC ACT CCA GAA GAG AGG CTG   222

ProValGluGly Ser Arg Pro Trp Ala Val Ala Arg Arg Val Leu          49
 35  CCCGTGGAAGGG AGC AGG CCA TGG GCA GTG GCC AGG CGG GTG CTG          267
223

ThrAlaIleLeu Ile Leu Gly Leu Leu Leu Cys Phe Ser Val Leu          64
 50  ACAGCTATCCTG ATT TTG GGC CTG CTT CTC TGT TTT TCT GTG CTT          312
268

LeuPheTyrAsn Phe Gln Asn Cys Gly Pro A
 65  TTGTTCTACAAC TTC CAG AAC TGT GGC CCT C   gtaagcaagatcccagaccccccaa.....0.26kb
313
```

FIG-2D

EXON 4 (SEQ ID NO:40)
344-520

```
                                      rg Pro Cys Glu Thr
            cccagctctgagctttcccccacag GC CCC TGT GAG ACA      79
                                                             357

80 Ser Val Cys Leu Asp Leu Arg Asp His Tyr Leu Ala Ser Gly Asn   94
358 TCT GTG TGT TTG GAT CTC CGG GAT CAT TAC CTG GCC TCT GGG AAC  402

95 Thr Ser Val Ala Pro Cys Thr Asp Phe Phe Ser Phe Ala Cys Gly  109
403 ACA AGT GTG GCC CCC TGC ACC GAC TTC TTC AGC TTT GCC TGT GGA  447

110 Arg Ala Lys Glu Thr Asn Ser Asn Phe Ser Phe Gln Glu Leu Ala Thr Lys  124
448 AGG GCC AAA GAG ACC AAT TCT AAT TTT TCT TTT CAG GAG CTT GCC ACA AAG  492

125 Asn Lys Asn Arg Leu Arg Arg Ile Leu G
493 AAC AAA AAC CGA CTT CGG AGA ATA CTG G  gtgaggaaagcaggggtggaagatgc....  ~2.6kb
```

FIG-2E

EXON 5 (SEQ ID NO:41)
521-645

```
                    tttagtcctcactcccatgcttccttctag       lu Val Gln Asn Ser Trp    139
                                                       AG GTC CAG AAT TCC TGG      537

140  His Pro Gly Ser Gly Glu Glu Lys Ala Phe Gln Phe Tyr Asn Ser           154
538  CAC CCA GGC TCT GGG GAG GAG AAA GCC TTC CAG TTC TAC AAC TCC           582

155  Cys Met Asp Thr Leu Ala Ile Glu Ala Ala Gly Thr Gly Pro Leu          169
583  TGC ATG GAT ACA CTT GCC ATT GAA GCT GCA GGG ACT GGT CCC CTC           627

170  Arg Gln Val Ile Glu Glu
628  AGA CAA GTT ATT GAG GAG      gtgagaaaagttgggatattaactt......0.33kb
```

FIG-2F

EXON 6 (SEQ ID NO:42)
646-792

```
                tcagccccctctctcctttaaag Leu Gly Gly Trp Arg Ile Ser Gly Lys   184
                                        CTT GGA GGC TGG CGC ATC TCT GGT AAA   672
185  Trp Thr Ser Leu Asn Phe Asn Arg Arg Thr Arg Leu Leu Met Ser              199
673  TGG ACT TCC TTA AAC TTT AAC CGA ACG AGA CTT CTG ATG AGT                  717
200  Gln Tyr Gly His Phe Pro Phe Phe Pro Arg Phe Ala Tyr Leu Gly Pro His      214
718  CAG TAT GGC CAT TTC CCT TTC TTC CCT AGA TTC GCC TAC CTA GGA CCT CAT      762
215  Pro Ala Ser Pro His Thr Pro Val Ile Gln
763  CCT GCC TCT CCA CAC ACA CCA GTC ATC CAG gtgagggatgcactggcgaagacac....~3.2kb
```

FIG-2G

EXON 7 (SEQ ID NO:43)
793-855

```
                                              Ile Asp Gln Pro Glu    229
     tctctccagtctctcttgtgcccag ATA GAC CAG CCA GAG                    807

230  Phe Asp Val Pro Leu Lys Gln Asp Gln Glu Gln Lys Ile Tyr Ala     244
808  TTT GAT GTT CCC CTC AAG CTC AAG CAA GAT CAA GAA CAG AAG ATC TAT GCC   852

245  Gln
853  CAG gtaagatggcacatggacaaaggcc.....0.093kb
```

FIG-2H

EXON 8 (SEQ ID NO:44)
856-1044

```
                                                                              tgtgactgacattcctctc
         Ile Phe Arg Glu Tyr Leu Thr Tyr Leu Asn Gln Leu Gly Thr
     cag ATC TTT CGG GAA TAC CTG ACT TAC CTG AAT CAG CTG GGA ACC              259
                                                                              897
260  Leu Leu Gly Gly Asp Pro Ser Lys Val Gln Glu His Ser Leu
898  TTG CTG GGA GGA GAC CCA AGC AAG GTG CAA GAA CAC TCT TTG                   274
                                                                              942
275  Ser Ile Ser Ile Thr Ser Arg Leu Phe Gln Phe Leu Arg Pro Leu
943  TCA ATC TCC ATC ACT TCA CGG CTG TTT CAG TTT CTG AGG CCC CTG              289
                                                                              987
290  Glu Gln Arg Arg Ala Gln Gly Lys Leu Phe Gln Met Val Thr Ile
988  GAG CAG CGG CGG GCA CAG GGC AAG CTC TTC CAG ATG GTC ACT ATC              304
                                                                              1032
305  Asp Gln Leu Lys
1033 GAC CAG CTC AAG gtgcctggaactgggggcagaaga.....0.23k
```

FIG-2I

EXON 9 (SEQ ID NO:45)
1045-1193

```
                                                                              ctcagcttt
                    Glu Met Ala Pro Ala Ile Asp Trp Leu Ser Cys           319
    gtgtccctcctctaag GAA ATG GCC CCC GCC ATC GAC TGG TTG TCC TGC          1077

320 Leu Gln Ala Thr Phe Thr Pro Met Ser Leu Ser Pro Ser Gln Ser           334
1078 TTG CAA GCG ACA TTC ACA CCG ATG TCC CTG TCC AGC CCT TCT CAG TCC      1122

335 Leu Val Val His Asp Val Glu Tyr Leu Lys Asn Met Ser Gln Leu           349
1123 CTC GTG GTC CAT GAC GTG GAA TAT TTG AAA AAC ATG TCA CAA CTG          1167

350 Val Glu Glu Met Leu Leu Lys Gln Ar
1168 GTG GAG GAG ATG CTG CTA AAG CAG AG gttcgccgcaggtggattgggggag....~1.3kb
```

FIG-2J

EXON 10 (SEQ ID NO:46)
1194-1323

```
                                                      g Asp Phe Leu Gln Ser His    364
             gtgtgggtctctcttgtctctccatag              G GAC TTT CTG CAG AGC CAC   1212

365  Met Ile Leu Gly Leu Val Val Thr Leu Ser Pro Ala Leu Asp Ser               379
1213 ATG ATC TTA GGG CTG GTG GTG ACC CTT TCT CCA GCC CTG GAC AGT              1257

380  Gln Phe Gln Glu Ala Arg Arg Lys Leu Ser Gln Lys Leu Arg Glu               394
1258 CAA TTC CAG GAG GCA CGC AGA AAG CTC AGC CAG AAA CTG CGG GAA              1302

395  Leu Thr Glu Gln Pro Pro Met
1303 CTG ACA GAG CAA CCA CCC ATG   gtgaggagaggagcggggtgtatttg....~6kb
```

FIG-2K

EXON 11 (SEQ ID NO:47)
1324-1434

```
                                            Pro Ala Arg Pro Arg Trp Met Lys    409
         actcattccagctttgtctccatag          CCT GCC CGC CCA CGA TGG ATG AAG    1347

410     Cys Val Glu Glu Thr Gly Thr Phe Phe Glu Pro Thr Leu Ala Ala           424
 1348    TGC GTG GAG GAG ACA GGC ACG TTC TTC GAG CCC ACG CTG GCG GCT           1392

425     Leu Phe Val Arg Glu Ala Phe Gly Pro Ser Thr Arg Ser Ala
 1393    TTG TTT GTT CGT GAG GCC TTT GGC CCG AGC ACC CGA AGT GCT gta tgtgagagctcttcccagccca....~1.6kb
```

FIG-2L

EXON 12 (SEQ ID NO:48)
1435-1533

```
                                                       ctgtccctggacctcactcccacag  Ala  439
                                                                                  GCC  1437

440  Met  Lys  Leu  Phe  Thr  Ala  Ile  Arg  Asp  Ala  Leu  Ile  Thr  Arg  Leu   454
1438 ATG  AAA  TTA  TTC  ACT  GCG  ATC  CGG  GAT  GCC  CTC  ATC  ACT  CGC  CTC   1482

455  Arg  Asn  Leu  Pro  Trp  Met  Asn  Glu  Glu  Thr  Gln  Asn  Met  Ala  Gln   469
1483 AGA  AAC  CTT  CCC  TGG  ATG  AAT  GAG  GAG  ACC  CAG  AAC  ATG  GCC  CAG   1527

470  Asp  Lys
1528 GAC  AAG  gtcaggccaggcgtcctggctggtg.....0.24kb
```

FIG-2M

EXON 13 (SEQ ID NO:49)
1534-1611

```
                                                                        tagcctctt
              ctgtgtctctctccag GTT GCT CAA CTG CAG GTG GAG ATG GGG GCT TCA   482
                               Val Ala Gln Leu Gln Val Glu Met Gly Ala Ser  1566

483           GAA TGG GCC CTG AAG CCA GAG CTG GCC CGA CAA GAA TAC AAC GAT    497
1567          Glu Trp Ala Leu Lys Pro Glu Leu Ala Arg Gln Glu Tyr Asn Asp   1611 gtgggtccctgtgttttccagctcc....0.44kb
```

FIG-2N

EXON 14 (SEQ ID NO:50)
1612-1712

```
                                                               Ile Gln    499
                            aagtcacctcctgcctcttcccccag         ATA CAG   1617

500   Leu Gly Ser Ser Phe Leu Gln Ser Val Leu Ser Cys Val Arg Ser        514
1618  CTT GGA TCG AGC TTC CTG CAG TCT GTC CTG AGC TGT GTC CGG TCC       1662

515   Leu Arg Ala Arg Ile Val Gln Ser Phe Leu Gln Pro His Pro Gln        529
1663  CTC CGA GCT AGA ATT GTC CAG AGC TTC TTG CAG CCT CAC CCC CAA       1707

530   His Ar
1708  CAC AG  gtatgacagcaggggagacacaggc....0.19kb
```

FIG-20

EXON 15 (SEQ ID NO:51)
1713-1823

```
                                            gagttcacatgtcctcttcc
                                                                              544
      g  Trp Lys Val Ser Pro Trp Asp Val Asn Ala Tyr Tyr Ser                 1752
   cacag G  TGG AAG GTG TCC CCT TGG GAC GTC AAT GCT TAC TAT TCG 545   Val Ser Asp His Val Val Phe Pro Ala Gly Leu Leu Gln Pro                 559
1753  GTA TCT GAC CAT GTG GTA GTC TTT CCA GCT GGA CTC CTC CAA CCC            1797

560   Pro Phe His Pro Gly Tyr Pro Ar
1798  CCA TTC TTC CAC CCT GGC TAT CCC AG  gtatgggtcactctgtaagggtagg.....0.15kb
```

FIG-2P

EXON 16 (SEQ ID NO:52)
1824-1891

```
                                                  g Ala Val Asn Phe Gly Ala  574
          gtcaaataagcccttgtctccctag              A GCC GTG AAC TTT GGC GCT  1842

575  Ala Gly Ser Ile Met Ala His Glu Leu Leu His Ile Phe Tyr Gln            589
1843 GCT GGC AGC ATC ATG GCC CAC GAG CTG TTG CAC ATC TTC TAC CAG            1887

590  Leu L
1888 CTC T gtgggtaacagggggccactggggagg.....0.23kb
```

FIG-2Q

EXON 17 (SEQ ID NO:53)
1892-2061

```
                                                                        tgttctcttgtcccatttca
      eu Leu Pro Gly Gly Cys Leu Ala Cys Asp Asn His Ala Leu             604
 acag TA  CTG CCT GGG GGC TGC CTC GCC TGT GAC AAC CAT GCC CTC           1932

Gln Glu Ala His Leu Cys Leu Lys Arg His Tyr Ala Phe Pro                 619
 CAG GAA GCT CAC CTG TGC CTG AAG CGC CAT TAT GCT TTT CCA                1977

Leu Pro Ser Arg Thr Ser Phe Asn Asp Ser Leu Thr Phe Leu Glu             634
 TTA CCT AGC AGA ACC TCC TTC AAT GAC TCC CTC ACA TTC TTA GAG            2022

Asn Ala Ala Asp Val Gly Gly Leu Ala Ile Ala Leu Gln
 AAT GCT GCA GAC GTT GGG GGG CTA GCC ATC GCG CTG CAG gtatgca             649
                                                                        2061 agtgtcaagggccacagt....0.35kb
```

EXON 18 (SEQ ID NO:54)
2062-2157

```
                                              cccttctctaccaccccctacccag  Ala Tyr   649
                                                                         GCA TAC  2067

650  Ser Lys Arg Leu Leu Arg His His Gly Glu Thr Val Leu Pro Ser          664
2068 AGC AAG AGG CTG TTA CGG CAC CAT GGG GAG ACT GTC CTG CCC AGC         2112

665  Leu Asp Leu Ser Pro Gln Gln Ile Phe Phe Arg Ser Tyr Ala Gln          679
2113 CTG GAC CTC AGC CCC CAG CAG ATC TTC TTT CGA AGC TAT GCC CAG          215 gtaggcagcggccacctcccgccac....~1.3kb
```

FIG-2X

EXON 19 (SEQ ID NO:55)
2158-2445

```
                                                                              ttcaataacctctcttcctgctcag
         Val Met Cys Arg Lys Pro Ser Pro Gln Asp Ser His Asp Thr His   694
2158     GTG ATG TGT AGG AAG CCC AGC CCC CAG GAC TCT CAC GAC ACT CAC   2202

Ser Pro Pro His Leu Arg Val His Gly Pro Leu Ser Ser Thr Pro   709
695      AGC CCT CCA CAC CTC CGA GTC CAC GGG CCC CTC AGC AGC ACC CCA   2247
2203

Ala Phe Ala Arg Tyr Phe Arg Cys Ala Arg Gly Ala Leu Leu Asn   724
710      GCC TTT GCC AGG TAT TTC CGC TGT GCA CGT GGT GCT CTC TTG AAC   2292
2248

Pro Ser Ser Arg Cys Gln Leu Trp ***
725      CCC TCC AGC CGC TGC CAG CTC TGG TAACTTGGTTACCAAAGATGCCACAGC    2343
2293

2344     ACAGAAATATCGACCAACACCTCCCTGGTCACATCCATGGAATCAGAGCAAGATTCCT      2402

2403     TTCTGCTTCTGTTCCAAAAATAAAAGCTGGCACTTGGCTTCCG
```

FIG-3

(SEQ ID NO:56)

```
        -176
-185   gtcacagtgcaagacaaaaggagacagaccaagggcaagattgcttggggagtgaagactc
-125   cctccctcttctcccctgagaagctgagggggaggagaagcctggtgccccc
                        GATA-1                    CACCC box
 -65   a d tgataagcaggc ccacccagaggccagtcctgtgtctggggacaaggcgaaagag
        GATA-1                                              Sp1
         -1  ▽
 -5    cagca GAA GTG CCC CTT CTC CAG GAT CAA GGA ACT GGG GCG GGG GGT
                                                         ▽
+43    GTT TCC TGG ACC CCA GTC CTC CGA ATC AGC TCC TAG AGT GGA ACC AGG
                                                    Met
+81    AAG GAT TCT GGA GCC ACA GAA GAT AGA CAG ATG gtaagtccccttttggagt
                            GATA-1
```

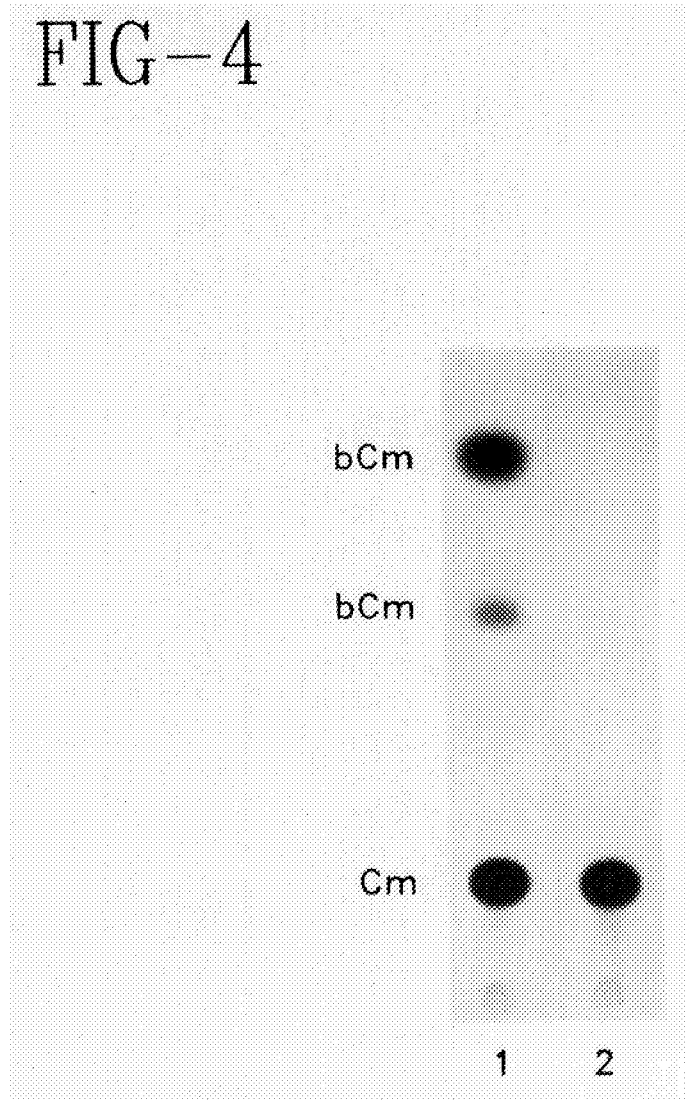

FIG-5

| Bone marrow cDNA library | Clone No. |
|---|---|
| AATAAAAAGCTGGCACTTGGCTTCCG-CCGGAATTC-3kb ext | 191 |
| AATAAAAAGCTGGCACTTGGCTTCCG(A) | 185 |
| AATAAAAAGCTGGCACTTGGCTTCC(A) | 182 |
| AATAAAAAGCTGGCACTTGGCTTC(A) | 190 |

| Peripheral blood | |
|---|---|
| AATAAAAAGCTGGCACTTGG(A) | 23 |
| AATAAAAAGCTGGCACTTGGCTTCC(A) | 22 |
| AATAAAAAGCTGGCACTTGGCTTCCGCTTGTCTCT(A) | 19 |
| AATAAAAAGCTGGCACTTGGCTTCCGCTTGTCTCTT(A) | 21 |

FIG-7

K2 (SEQ ID NO:57)

```
185                                                              199
Trp Thr Ser Leu Asn Phe Asn Arg Thr Leu Arg Leu Leu Met Ser
TGG ACT TCC TTA AAC TTT AAC CGA ACG CTG AGA CTT CTG ATG AGT
                                       →
```

K1 (SEQ ID NO:58)

```
TGG ACT TCC TTA AAC TTT AAC CGA ATG CTG AGA CTT CTG ATG AGT
Trp Thr Ser Leu Asn Phe Asn Arg Met Leu Arg Leu Leu Met Ser
```

FIG-10

K 6, -7 genotype

```
                                                                  Ala Val Asn Phe Gly Ala
                                                             ....A GCC GTG AAC TTT GGC GCT    589
                                                                                              1887

575   Ala Gly Ser Ile Met Ala His Glu Leu Leu His Ile Phe Tyr Gln        604
1843  GCT GGC AGC ATC ATG GCC CAC GAG CTG TTG CAC ATC TTC TAC CAG        1932
      Exon 16 | Exon 17
590   Leu Leu Pro Gly Gly Cys Leu Ala Cys Asp Asn His Ala Leu            619
1888  CTC TTA CTG CCT GGG GGC TGC CTC GCC TGT GAC AAC CAT GCC CTC        1977
                              CCC
                              Pro
605   Gln Glu Ala His Leu Cys Arg His Tyr Ala Ala Phe Pro                634
1933  CAG GAA GCT CAC CTG TGC CGC CAT TAT GCT GCC TTT CCA                2022
620   Leu Pro Ser Arg Thr Ser Phe Asn Asp Ser Leu Thr Phe Leu Glu        649
1978  TTA CCT AGC AGA ACC TCC TTC AAT GAC TCC CTC ACA TTC TTA GAG
                                                              TTG
635   Asn Ala Ala Asp Val Gly Gly Leu Ala Ile Ala Leu Gln ........
2023  AAT GCT GCA GAC GTT GGG GGG CTA GCC ATC GCG CTG CAG ........
```

FIG-13

Molecular basis of K10 (Ul$^a$)

EXON 13
1534-1611

```
                    Val Ala Gln Leu Gln Val Glu Met Gly Ala Ser    484
      ctgtgtctctccag GTT GCT CAA CTG CAG GTG GAG ATG GGG GCT TCA   1566

485   Glu Trp Ala Leu Lys Pro Glu Leu Ala Arg Gln Glu Tyr Asn Asp  499
1567  GAA TGG GCC CTG AAG CCA GAG CTG GCC CGA CAA GAA TAC AAC GAT 1611
                                                GTA
                                                Val  K10(Ul$^a$)

gtgggtccctgtgttttccagctcc....0.44kb
```

FIG-14

Molecular basis of Kpª, Kpᵇ and Kpᶜ

EXON 8
856-1044 (Wild-Type Kpᵇ)

```
856                 Ile Phe Arg Glu Tyr Leu Thr Tyr Leu Asn Gln Leu Gly Thr
            cag     ATC TTT CGG GAA TAC CTG ACT TAC CTG AAT CAG CTG GGA ACC   259
                                                                              897

260         Leu Leu Gly Gly Asp Pro Ser Lys Val Gln Glu His Ser Ser Leu
898         TTG CTG GGA GGA GAC CCA AGC AAG GTG CAA GAA CAC TCT TCC TTG       274
                                                                              942

275         Ser Ile Ser Ile Thr Ser  Arg  Leu Phe Gln Phe Leu Arg Pro Leu
943         TCA ATC TCC ATC ACT TCA  CGG  CTG TTC CAG TTT CTG AGG CCC CTG     289
                                    TGG                                       987
                                    Trp         Kpª
                                    CAG
                                    Gln         Kpᶜ

290         Glu Gln Arg Arg Ala Gln Gln Gly Lys Leu Phe Gln Met Val Thr Ile
988         GAG CAG CGG CGG GCA CAG CAG GGC AAG CTC TTC CAG ATG GTC ACT ATC   304
                                                                              1032

305         Asp Gln Leu Lys
1033        GAC CAG CTC AAG gtgcctggaactg
```

DIAGNOSTIC METHODS AND KIT FOR DETERMINING KELL BLOOD GROUP GENOTYPE

CROSS REFERENCE TO RELATED APPLICATIONS

This application is a continuation-in-part of U.S. application Ser. No. 08/337,268 filed on Nov. 10, 1994, now U.S. Pat. No. 5,5,336 the entire disclosure of which is incorporated herein by reference.

This invention was made with Government support under Grant HL35841 awarded by the NIH. The Government has certain rights in this invention.

BACKGROUND OF THE INVENTION

This invention relates to a method for determining Kell blood group genotype. More particularly, the invention relates to molecular genetic methods for the determination of inter alia K1/K2, K6/K7, K10/K(-10), and K3/K4/K21 genotypes.

The Kell blood group system is a well-known but complex group of blood antigens, comprising over 20 different related antigens. Of these, the antigen K1 (K, Kell) is known to be the strongest immunogen among the 23 known phenotypes. Serologically, the K1 sublocus has an allelic relationship with a high frequency antigen K2 (k, Cellano). Approximately 9% of the population has the K1 red cell phenotype, and antibodies to K1 are developed in about 5% of persons receiving a single unit of incompatible blood (Ref. 1).

Hemolytic disease of the newborn (HDN) is usually associated with maternal alloimmunization to Rh(D), but K1 incompatibilities can also cause severe hemolytic disease in newborns (Refs. 2–7). K1 sensitization from a previous pregnancy can result in HDN and complications during subsequent pregnancies if the fetus is a K1 carrier. Similar types of problems can arise in the more rare case of K2 sensitization. The identification of the fetal K1/K2 genotype would be of particular significance in situations in which the father is a K1/K2 heterozygote. Since the mother must be a homozygote in order to have been previously sensitized, there is a 50% chance that the fetus with a K:1,2 father is in danger of HDN. Because of this 50% risk, identification of the homozygosity or heterozygosity of the K1/K2 genotype of the fetus in these pregnancies becomes important in order to aid in their proper management. It is important to recognize, however, that the determination of parental genotype with respect to Kell antigens other than K1/K2 can also be of significance for managing pregnancies.

Kell inheritance is autosomal and codominant, and the gene for the Kell protein (KEL) has been mapped to chromosome 7q33 (Refs. 8–11). Kell antigens appear to be encoded in 5 sets of antithetical paired alleles expressing high and low prevalence antigens. Thus, K1 (K) and K2 (k) are products of alleles, as are K3 ($Kp^a$), K4 ($Kp^b$) and K21 ($Kp^c$); K6 ($Js^a$) and K7 ($Js^b$); K17 and K11; and K24 and K14. However, a number of high prevalence antigens such as K12, K13, K18 and K22 are independently expressed. Some Kell phenotypes are segregated by racial or ethnic groups. For example, K6, which was first reported in 1958, is more frequent in African-Americans, occurring in up to 19.5% in this group in a study performed in Seattle, Wash. (Ref. 12). Also, K10 ($Ul^a$) is more prevalent in Finns (Ref. 13). These various relationships, and their places in the Kell system, have been established through the years by serological analyses of informative families (Refs. 14–18).

A variety of studies, including a molecular cloning, established that Kell blood group antigens are carried on a 93 kDa type II glycoprotein (Refs. 19–25) found on the surface of red blood cells (Ref. 26). The Kell protein has a short, 46 amino acid, N-terminal domain in the cytoplasm, and a large C-terminal portion, of 665 amino acids, on the external surface of the red cell. All of the carbohydrates are N-linked (Ref. 27), probably located in 5 sites, at asparagines 93, 115, 191, 345 and 627. Early biochemical studies suggested that Kell antigens reside on a protein whose conformation is largely dependent on disulfide bonds (Ref. 28). The Kell protein has 16 cysteine residues, one in the transmembrane region and 15 in the external portion (Ref. 25). Reduction of red cells by sulfhydryl reagents results in loss of Kell antigens and exposure of some neo-epitopes (Ref. 28).

The antigenic structure of the Kell protein has also begun to be mapped. A recently developed immunological test, MAIEA, which uses monoclonal antibodies to different Kell antigens, indicates that certain of the identified Kell antigens occur in spatially distinct regions of the glycoprotein (Ref. 26). For example, the K1/K2, and K6/K7 domains appear to be close together, while K3/K4 epitope is in a different location and K18 is in yet another protein domain (Ref. 29).

The determination of Kell genotype has heretofore been confined to inferences drawn from the detection and identification of Kell antigens. Such methods employ antibodies or other compounds which identify and interact with the Kell protein or portions thereof. For example, various antibodies specific for particular Kell antigens have been identified (Refs. 13, 22). Agglutination methods for detecting Kell protein and other blood group antigens are described in U.S. Pat. Nos. 5,324,479, 5,302,512, 5,213,963, 4,560,647, 4,403,042, 4,358,436, and 4,148,607. These methods provide information about expressed protein profiles, not about protein molecular structure or the molecular genetic makeup of the individual. Zelinski et al. describe a method for indirectly inferring Kell genotype from linkage studies using marker genes (Ref. 30). Such methods, however, provide only limited and indirect information about Kell genotype. Generally, these methods also require obtaining blood samples from subjects being examined. Determining fetal Kell phenotype also normally requires a fetal blood sample. This involves a potentially dangerous procedure in which the fetus is susceptible to hemorrhage and possibly death. None of the methods previously described discloses any method by which Kell genotype might be determined simply and directly on the basis of the KEL gene structure.

As a result, there exists a need for a method of safely and conveniently detecting Kell genotype. It would also be desirable to provide a method for determining Kell genotype in a fetus without the requirement for obtaining blood samples. A test based on DNA samples taken from amniotic cells would allow the clinician to avoid the risk of harm to the fetus and to more accurately predict the potential of anti-Kell-associated HDN.

SUMMARY OF THE INVENTION

The present invention provides a diagnostic method for the differential determination of Kell blood group genotype in a subject. The diagnostic method includes generating a characteristic nucleic acid product, from a source or sample of nucleic acid containing a Kell polymorphism locus, in an amount which is sufficient to enable the characterization of Kell genotype. The method may be employed to determine Kell genotype with respect to one or more Kell polymorphisms or Kell phenotypes. Preferably, the method is directed to detecting the Kell polymorphism loci which determine: K1/K2 genotype, K6/K7 genotype, K10/K(–10) genotype, and/or K3/K4/K21 genotype.

In a first preferred embodiment, the method includes:
selectively cleaving a nucleic acid sample which includes a Kell polymorphism locus, preferably genomic DNA of the subject, to provide a nucleic acid product which includes one or more nucleic acid fragments in an amount sufficient to characterize Kell genotype. Preferably, the method includes selectively cleaving nucleic acid which includes one or more of the K1/K2 polymorphism locus, the K6/K7 polymorphism locus, the K10/K(–10) polymorphism locus, and the K3/K4/K21 polymorphism locus.

The selective cleaving of DNA is accomplished by digesting the sample nucleic acid with a restriction enzyme which cleaves the DNA differentially based on a Kell polymorphism locus. Any suitable restriction enzyme may be employed as desired. In the case of K1/K2 polymorphism locus, a preferred restriction enzyme is BsmI. In the case of the K6/K7 polymorphism locus, preferred restriction enzymes include MnlI and/or DdeI. In the case of K10 genotype, a preferred restriction enzyme is AccI. In the case of the K3/K4/K21 polymorphism, preferred restriction enzymes include NlaIII and/or PvuII. Combinations of such enzymes may be employed when more than one Kell polymorphism is desired to be differentiated.

This diagnostic method preferably includes amplifying Kell DNA from a DNA sample obtained from a subject. Typically the amplification involves using a primer which amplifies only nucleic acid including the locus which determines a specific Kell polymorphism. Primers may be selected to selectively amplify DNA including particular Kell polymorphism loci, including the K1/K2 polymorphism locus, the K6/K7 polymorphism locus, the K10/K(–10) polymorphism locus, and/or the K3/K4/K21 polymorphism locus.

Preferably, the digesting of Kell nucleic acid by a restriction enzyme is performed following amplification of nucleic acid obtained from the subject, but the digesting may be performed preceding such amplification.

In a second preferred embodiment, the diagnostic method of the invention involves differentially amplifying a nucleic acid sample which includes a Kell polymorphism locus to provide a nucleic acid product which can be employed to characterize Kell genotype. Preferably, the sample nucleic acid operates as template permitting amplification by means of a primer which differentially amplifies nucleic acid encoding one specific allele of a set of alleles associated with a Kell polymorphism.

In the diagnostic methods of the invention which require a primer or primer set, the primer or primer set may include a single primer, or may include a plurality of primers, including, for example, a plurality of primer pairs. For example, in a preferred mode, the method of the invention may employ a primer which specifically amplifies K1 DNA (K1 allele-specific primer), a primer which specifically amplifies K2 DNA (K2 allele-specific primer), and two primers which each amplify both K1 and K2 DNA (allele-non-specific primers). In this mode, different sized PCR products are produced which correspond to a K1 DNA, K2 DNA and K1/K2 DNA. The pattern of PCR fragments serves to differentiate among K1/K1, K2/K2, and K1/K2 genotypes.

Primers are included which differentially amplify nucleic acid templates containing a K6 locus and/or a K7 locus. Primers are also included which differentially amplify nucleic acid templates containing a K10 locus and/or a K(–10) locus. Also, primers are included which differentially amplify nucleic acid templates associated with a K3 locus, a K4 locus, and/or a K21 locus.

An especially preferred oligonucleotide primer which is allele-specific for K1-containing nucleic acid comprises a nucleotide sequence selected from the group of nucleotide sequences including: ATA CTG ACT CAT CAG AAG TTT CAG CA (SEQ ID NO:1), and ATA CTG ACT CAT CAG AAG TCT CAG CA (SEQ ID NO:2), and ATA CTG ACT CAT CAG AAG TGT CAG CA (SEQ ID NO:61).

An especially preferred oligonucleotide primer which is allele-specific for K2-containing nucleic acid has the nucleotide sequence: TGG ACT TCC TTA AAC TTT AAC TGA AC (SEQ ID NO:3).

Especially preferred oligonucleotide primers specific for K1- and K2-containing nucleic acids (but allele-non-specific) have nucleotide sequences selected from the group of nucleotide sequences including: TTT AGT CCT CAC TCC CAT GCT TCC (SEQ ID NO:4), and TAT CAC ACA GGT GTC CTC TCT TCC (SEQ ID NO:5), TTA GTC CTC ACT CNC CAT GCT TCC (SEQ ID NO:62), and TCA CAC AGG TGT CCT CTC TTC C (SEQ ID NO:63). The primers may be used in pairs for amplification.

An especially preferred oligonucleotide primer specific for K6- and K7-containing nucleic acids has nucleotide sequences selected from the group of nucleotide sequences including: CTC ACC TAG GCA GCA CCA ACC CTA (SEQ ID NO:64) and TTA CCT GGA GGG CAT GGT TGT CAC T (SEQ ID NO:65).

The diagnostic method of the invention preferably further includes the derivation of information of information from generated nucleic acid restriction fragments or amplification products. Preferably, the derivation of information includes separating the nucleic acid products to provide a pattern of fragments which provides specific information characterizing Kell genotype. More preferably, the separation provides a pattern of nucleic acid products which provides specific information characterizing K1/K2 genotype, K6/K7 genotype, K10/K(–10) genotype, and/or K3/K4/K21 genotype. In addition, it is preferred to detect some or all of the Kell nucleic acid products, such as by marking or staining one or more products. Products may be marked with a non-specific marker substance. Such substances may be used to stain some or all of the products to permit their differentiation based on the pattern of their separation. Alternatively, the detecting step may include marking one or more of the Kell nucleic acid products with one or more hybridization probes in a selective or specific fashion. Preferably, a hybridization probe(s) is employed which specifically marks one or more nucleic acid products which include a Kell polymorphism locus of interest, such as the K1 locus or the K2 locus.

The molecular genetic method of the invention generally involves obtaining nucleic acid, preferably genomic DNA, from a biological sample from a human subject or patient. A blood sample is typically preferred, but other types of tissue samples which contain erythroid tissue are useful. In a particularly preferred embodiment, the invention provides a method for determining K1/K2 Kell blood group genotype in a fetus. In this embodiment, the preferred tissue sample includes a sample of amniotic fluid or chorionic villus.

The invention further provides Kell-based nucleic acid oligomers which include nucleotide sequences which are at least substantially complementary to a polymorphic region of a Kell-based nucleic acid, such as Kell genomic DNA, mRNA or cDNA. In particular, the invention provides nucleic acid oligomers which include a nucleic acid sequence substantially complementary to K1 DNA, as well as oligomers which include a nucleic acid sequence substantially complementary to K2 DNA. Preferably, the oligomers of the invention are exactly complementary to the region of interest.

Moreover, the invention provides nucleic acid oligomers which include a nucleic acid sequence substantially homologous to a polymorphic region of a Kell-based nucleic acid, such as Kell genomic DNA, mRNA or cDNA. In particular, the invention provides nucleic acid oligomers which include a nucleic acid sequence substantially homologous to K1 DNA, as well as oligomers which include a nucleic acid sequence substantially homologous to K2 DNA. These oligomers of the invention preferably include a nucleic acid sequence which is at least in part, exactly homologous to a target region of a Kell-based nucleic acid.

The nucleic acid oligomers of the invention may be used as hybridization probes to identify the presence of target nucleic acid sequences, through binding to or hybridizing with such target sequences. Accordingly, the nucleic acid oligomers may be detectably labeled by being linked to a detectable marker moiety such as a fluoresent label, an electron dense substance, a reporter moiety, a specific or nonspecific binding moiety, or other detectable moiety such as is known in the art. Optionally, the oligomers of the invention may further include a reactive moiety permitting cross-linking with a target nucleic acid sequence. Furthermore, the oligomers of the invention may be linked to a substrate material, for example, to a gel or resin to immobilize the oligomers.

The oligomers of the invention may also be employed as amplification primers which specifically bind to and cause elongation through a region of Kell nucleic acid comprising a Kell polymorphism locus. Preferred primers bind to or cause elongation through Kell nucleic acid which contains a K1/K2 locus, a K6/K7 locus, a K10/K(−10) locus, and/or a K3/K4/K21 locus.

Moreover, the identification of the locus characterizing the K1/K2 polymorphism now permits the preparation of Kell-based polypeptides which include amino acid sequences which are substantially homologous to the K1 domain or to the K2 domain of the Kell protein. The polypeptides may be derived from natural sources and substantially purified or may be synthesized in substantially pure form as desired. Such polypeptides may also be detectably labeled, may be attached to reactive moieties, and may be bound to a substrate in accordance with methods known in the art. The polypeptides of the invention are useful as probes for, for example, detecting alloimmunization in a subject or patient. In such an assay, the polypeptide may comprise an amino acid sequence which is substantially homologous to K1 antigen and presents an immunologic profile which permits specific reaction with anti-K1 antibodies.

Thus in another embodiment, the invention provides a diagnostic method for detecting alloimmunization of a patient to a Kell antigen, preferably K1 antigen. In this embodiment, the method includes obtaining a blood sample from a patient or subject, and measuring a parameter of immune reactivity of the sample with a polypeptide probe. The polypeptide probe preferably includes an amino acid sequence which is substantially homologous to the K1/K2 domain of the Kell protein. Moreover, it is desirable that the polypeptide probe be specifically reactive with anti-K1 antibodies present in the sample. The invention also enables comparable methods for the detection of alloimmunization of a subject to other Kell antigens, including K6, K10, as well as K3 and K21.

In another embodiment, a diagnostic kit is provided for determining Kell blood group genotype in a sample of tissue from a patient. In this embodiment, the invention provides a diagnostic kit for determining Kell blood group genotype by detecting target nucleic acid sequences, such as sequences specific to K1 and K2. The kit includes amplification primers, i.e., oligonucleotides that bind to or cause elongation through sequences specific to K1 and K2. The in vitro kit further includes a container, such as a microtiter plate having a plurality of wells, having bound thereto oligonucleotide capture probes having nucleic acid sequences substantially complementary to the K1 and K2 target sequences.

Alternatively, the invention provides a diagnostic kit for determining Kell blood group genotype by detecting target nucleic acid sequences specific to particular Kell antigens, such as K1 and K2. In this embodiment, the kit includes:

(a) a primer set including first and second PCR primers wherein the first PCR primer is an oligonucleotide that will bind to or cause elongation through a sequence specific to K1 and the second PCR primer is an oligonucleotide that will bind to or cause elongation through a sequence specific to K2; and (b) a container, such as a microtiter plate having a plurality of wells, having bound thereto oligonucleotide capture probes having a nucleic acid sequence substantially complementary to the target sequences.

The invention further provides recombinant expression vectors which carry Kell nucleic acid sequences. The invention provides expression vectors which include a nucleic acid sequence which encodes at least a part of the Kell protein including a part of the protein which encodes a site of Kell polymorphism. In particular, the invention provides expression vectors which carry K1 cDNA permitting transformation of cells to produce transformed cells or transformants which express K1 protein on their cell surfaces. Vectors are also provided which carry K6 cDNA, as well as vectors which carry K3 or K21 cDNA, permitting transformation of cells to express K6, as well as K3 and K21, respectively. The invention also provides a stable cell lines which have been modified (i.e., transformed) to express protein on its cell surface, as well as a method for transforming a cell line to express such protein. With respect to the K1 expression, such protein preferably includes at least the K1 domain, and more preferably, the protein is K1 protein. Similarly expression of K6 as well as K3 and K21, the expressed protein preferably includes the K6, the K3 or the K21, domain respectively; more preferably, the protein is K6, K3, or K21 protein, respectively. The invention further provides a method of making an antibody specific for a Kell antigen, by inducing the generation of at least one antibody against a Kell antigen expressed by a transformed cell line produced according to the invention. Polyclonal antibodies are contemplated, but the antibody is preferably monospecific, such as a monoclonal antibody or an antigen-binding region thereof.

Accordingly, as a result of the invention, there is now provided a safe and convenient diagnostic method for differentially determining the Kell genotype of patients. In particular, there is now provided a method for determining Kell genotype in a fetus in utero without requiring the taking of a blood sample. A test based on determining Kell genotype, in particular K1/K2 genotype, from DNA obtained from amniotic fluid now allows the clinician to reduce the degree of risk to the fetus being tested. Moreover, the new diagnostic method permits the accurate prediction of the potential of anti-K-associated hemolytic disease of the newborn.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawing, wherein:

FIGS. 2A–2R and 2X show the nucleotide sequences of the exons of the Kell gene.

FIG. 3 shows the 5' flanking region and exon 1 of the Kell gene.

FIG. 4 shows an autoradiogram illustrating the promoter activity of the 5' flanking region of the Kell gene.

FIG. 5 shows a comparison of the 3' ends of the Kell gene obtained from various clones of the gene.

FIG. 7 shows a comparison of corresponding portions of K1 DNA and K2 DNA.

FIG. 10 shows a comparison of corresponding portions of K6 DNA and K7 DNA.

FIG. 13 shows a comparison of corrsponding portions of K10 DNA and K(-10) DNA.

FIG. 14 shows a comparison of corresponding portions of K3 DNA, K4 DNA, and K21 DNA.

DETAILED DESCRIPTION OF THE INVENTION

Figure 1:
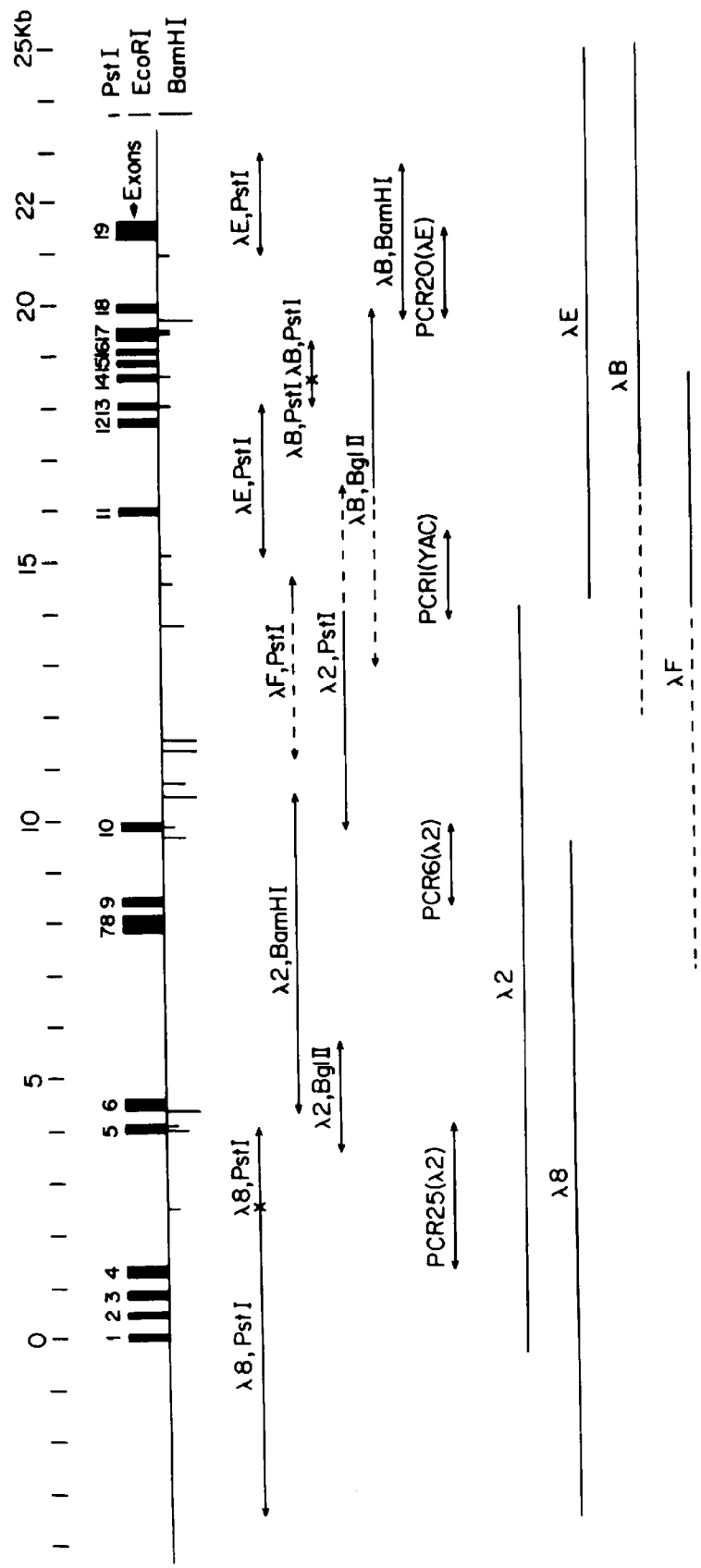
FIG. 1 shows a map of the Kell gene indicating the loci of the Kell exons, the relationships among the clones used to establish the exon locations, as well as restriction sites in the Kell gene.

The Kell blood group system is distinguished by its antigenic complexity (Ref. 18). Over 20 different antigens have been ascribed to the Kell system. A majority of the antigens are organized in 5 antithetical sets of high and low frequency antigens, with other Kell antigens being independently expressed. The molecular basis for this antigenic diversity has not previously been understood. The present invention, which involves description of the organization of the KEL gene and the boundaries of its 19 exons, now enables the molecular characterization of the different Kell phenotypes.

The molecular basis of the different Kell phenotypes has not previously been determined. Having now studied the structure of the KEL gene, and identified for the first time the 19 exons which encode Kell protein, molecular bases of polymorphisms in the Kell genotype have now been determined.

In particular, the K1/K2 polymorphism and its locus has now been determined by sequencing the exons of K1/K1 DNA and comparing them to K2/K2 sequences. It was unexpectedly been found that base substitution in exon 6 of the K1 genotype predicts an amino acid change. This base substitution also creates a restriction enzyme site which has been employed to test over 40 different samples to confirm that the base substitution identifies the K1 genotype.

As another of the Kell group of antigens, K6 (also known as $Js^a$) is a low frequency red cell antigen which has an allelic relationship with the high frequency K7 antigen. K6 appears in less than 1.0% of the total population, but up to 19.5% of African-Americans carry the K6 antigen. We have now determined the molecular basis of polymorphism in the K6/K7 polymorphism by sequencing the 19 exons of the Kell gene (KEL) of a K:6,–7 person. Comparisons of the sequence obtained from K:6,–7 DNA with that of K:6,7 DNA showed an unexpected base substitution in exon 17 that predicts an amino acid change from leucine to proline. This base change also causes a deletion of a restriction enzyme cleavage site. Another base change in K7 is silent in that it does not result in change in the expressed protein, yet it causes the deletion of another restriction enzyme cleavage site which can be exploited to differentiate K6/K7 genotype.

The K10 ($Ul^a$) antigen is a low frequency Kell antigen for which there is no corresponding serologically detectable high frequency antigen. Thus, the wild-type phenotype (designated herein as K(-10) is characterized by a lack of the K10 antigen. It has now been determined that the molecular basis of the K10 polymorphism resides in exon 13. A point mutation at nt 1601 has been found to predict an amino acid change from glutamic acid to valine. This base change also creates a new restriction enzyme cleavage site which can be employed to determine K10 genotype according to the invention.

Another of the antithetical allelic sets in the Kell genotype is the K3/K4/K21 ($Kp^a/Kp^b/Kp^c$) set. Our study of the KEL gene has also unexpectedly revealed that the three alleles in this set may be differentiated on the basis of changes in two adjacent nucleotides in exon 8, each of which predicts a discrete amino acid change at the same position in the amino acid sequence of the Kell protein. Each of the base changes also creates a new and distinct restriction enzyme cleavage site in the gene.

The most prevalent Kell phenotype is K:-1, 2, -3, 4, -6, 7, 9, 11, 12, 14, 18, 19, 22. We have now defined the 19 exons of the KEL gene of a person with common Kell phenotype. To determine the molecular basis of Kell polymorphisms we designed a series of primers which would amplify the 19 exons of KELL. We then compared the DNA sequences of persons expressing various combinations of high and low frequency antigens to determine sequence variations potentially related to the observed variations in antigen expression.

For example, we compared the DNA sequences of K1/K1 and K2/K2 DNA. The only base change which would encode a different amino acid was found in exon 6, and changed a threonine to a methionine at a consensus N-glycosylation motif (Asn.X.Thr→Met). This change would prevent N-linked glycosylation at this site. Based on the amino acid sequence of Kell protein of common phenotype, there are 6 possible N-glycosylation sites, i.e., asparagine residues 93, 115, 191, 345, 627 and 724. However, the asparagine at position 724 is probably not glycosylated because it is part of a sequence Asn.Pro.Ser and the presence of proline between asparagine and serine/ threonine inhibits N-glycosylation (Ref. 31). In any event, changing threonine to methionine at position 193 would prevent glycosylation at asparagine 191. Thus, K1 protein would be composed of at most 4 instead of 5 carbohydrate moieties. Lack of a carbohydrate side-chain may expose different parts of the protein leading to immunogenicity. The loss of glycosylation in a red cell surface protein can lead to a change in blood group phenotype. The Webb glycophorin C variant also lacks an N-glycan (Refs. 32–33).

It has also now been observed that the point mutation from C to T in exon 6 also creates a new restriction enzyme site, 5'-GAATGCT-3', which can be cut by BsmI, a well known restriction endonuclease. The use of restriction enzyme digestion allows the differentiation of K1 /K1 and K2/K2 homozygotes and of K1/K2 heterozygotes, permitting the development of a diagnostic genotype procedure.

While not wishing to be bound by theory, it is known that, in very rare cases, red blood cells will be observed which do not express any Kell antigens. In this phenotype, known as $K_o$ (null), the red cells appear not to have any Kell protein on the cell membrane. Yet, preliminary experiments in our laboratory indicate that two $K_o$ persons contain Kell mRNA in peripheral blood and that the sequence of the mRNA from the initiation ATG codon to the poly A tail is identical to mRNA obtained from persons with common Kell phenotype. This indicates that the base sequences in the 19 exons of K2 and of some $K_o$ persons are identical. Therefore, PCR amplification of exon 6 and genotyping by treatment with BsmI could indicate a K2 genotype in $K_o$ persons. Serological analysis easily detects the $K_o$ homozygote, but the $K_o$ heterozygotes would be serologically identified as K2 or K1, and BsmI analysis would provide no further discrimination. Presumably, the same would occur in the Kmod phenotypes in which expression of all Kell-related antigens are weakened. Nonetheless, for practical purposes, such ambiguous phenotypes are less clinically significant since $K_o$ and Kmod phenotypes are very rare. $K_o$ heterozygotes would be phenotypically, and therefore clinically, equivalent to K1 or K2 homozygotes. What is generally important in K1-sensitized pregnancies is to identify whether the fetus is a K1 carrier or not. The method of the invention now allows identification of Kell genotype, including identification of the K1 gene.

We have also now determined the molecular basis of polymorphism in the K6/K7 allelic set ("K6/K7 polymorphism") by sequencing the 19 exons of the Kell gene (KEL) of a K:6,–7 person. Comparisons of the sequence obtained from K:6,–7 DNA with that of K:6,7 DNA showed a T to C base substitution at nt 1910 in exon 17 that predicts an amino acid change from leucine in K7 to proline in K6. The T to C substitution at nt 1910 eliminated an MnlI restriction enzyme site found in K7. Analysis of a 111 bp PCR-amplified product of exon 17 spanning the T to C substitution was performed with MnlI. Eight unrelated persons with the K6 phenotype were tested and all contained the T to C substitution at nt 1910. Another base substitution from A to G at nt 2019 in exon 17 was also noted, but this point mutation did not encode a different amino acid. Even so, this substitution was found to create a new DdeI restriction enzyme site. Thus, these base substitutions permit diagnostic procedures for the differentiation of K6 from K7 according to the invention.

The molecular bases of the K3/K4/K21 polymorphism have also now been characterized. Two discrete changes in a single codon have been found to be associated with changes in protein expression from K4 to either of K3 or K21. The same changes also encode new and unique restriction cleavage sites which specifically characterize K3 and K21 nucleic acid as distinct from wild-type K4 nucleic acid. In the case of K3, a C 961 T substitution results in an Arg 281 Trp change. This base substitution also creates a new NlaIII restriction enzyme site. In the case of K21, a G 962 A substitution encodes Arg 281 Gln. This substitution also creates a new PvuII restriction enzyme site. Accordingly, the differentiation of K4 from K3 and K21 genotypes is possible by employing the diagnostic method of the invention.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional interpretations may be implied.

As used herein, the term "restriction fragment length polymorphism" or "RFLP" refers to the differences in DNA nucleotide sequences that are randomly distributed throughout the entire genome and that produce different restriction endonuclease patterns for different individuals upon digestion of genomic DNA. Likewise, "restriction site" refers to a site in a nucleic acid at which a restriction enzyme cleaves the nucleic acid. Cleavage of a nucleic acid by a restriction enzyme generates pieces of nucleic acid termed "restriction fragments". When a restriction site is gained or lost as a result of mutation or allelism, the restriction fragment pattern can vary, yielding information about the location of the site.

"Polymorphic" or "DNA polymorphism" refers to the condition in which two or more variations of a specific DNA sequence coexist in the same interbreeding population. Polymorphic differences are caused by differences in amino acid sequence which may be due to point mutations, gene rearrangements or alternative splicing. "Alleles" are genes which are polymorphic variants of one another and occur alternatively at a given locus in the genome.

A gene encoding a Kell protein is designated a "Kell gene". The region of a Kell gene which encodes a specific domain of a Kell protein is termed a "Kell locus". For example, it has been determined as a result of the present invention that the K1 antigen and the K2 antigen are encoded by alleles of the Kell gene. More specifically, the K1 antigen and the K2 antigen are alternate versions of the same domain of the Kell protein, in which a single amino acid substitution has been found to result in the difference between Kell protein including the K1 antigen and Kell protein including the K2 antigen. This single amino acid substitution has now been found to arise from a single nucleotide substitution in the Kell gene. Thus, the portion of the Kell gene which includes this site of nucleotide variation is designated the "K1/K2 locus". When the K1/K2 locus encodes K1 antigen this region of the Kell gene is designated the "K1 locus". When the K1/K2 locus encodes K2 antigen, this region of the Kell gene is designated the "K2 locus". The K1 /K2 locus is also said to be the site or locus which determines or characterizes the "K1/K2 polymorphism", i.e., the observed phenotypic difference between the K1 and K2 antigens. Similarly, other Kell loci determine or characterize other Kell polymorphisms, such as the K6/K7, K10/ K(–10), and K3/K4/K21 polymorphisms.

For purposes of this invention, Kell protein which includes a particular domain of interest may be designated according to that domain regardless of the other domains in the protein. Thus, if a Kell protein includes the domain responsible for K1 antigen, the protein may be designated "K1 protein", while Kell protein which includes the K2 antigen or K2 domain is designated "K2 protein". Using similar analysis, DNA encoding K1 protein may be termed "K1 DNA", while DNA encoding K2 protein may be termed "K2 DNA" regardless of whether or not the DNA further encodes other Kell domains. It is also to be understood that other Kell-related or Kell-based chromosomal DNA (including exons and introns and parts thereof), nucleic acid templates, nucleic acid transcripts, as well as cDNA, may be similarly designated as K1/K2, K1, or K2, depending on context or application. Similar considerations apply in the context of other antigens in the Kell system, such as the K6/K7, K10, and K3/K4/K21 antigens.

As a result of the present invention, it is now possible to design probes and/or primers comprising nucleic acid oligomers or oligonucleotides which can be employed to detect polymorphisms in the Kell gene. The probes or primers suitable for this purpose preferentially hybridize with or are specific for a region of the Kell gene comprising a site or region in which a point change in nucleotide sequence causes a change in the Kell gene product characterizing a polymorphism. Accordingly, the probes or primers include those which hybridize with higher frequency alleles as well as those which hybridize with lower frequency alleles. In certain applications, it is desirable to define the presence of heterozygosity. In such cases probe or primer combinations enabling differential detection of two or more alleles and/or loci have been found to be useful.

For example, a probe of the invention may be said to bind to or hybridize with Kell DNA if it specifically recognizes a defined region of Kell DNA. Greater precision is intended when a probe is said to hybridize with a specific allele such as a "K1 probe" which is understood to hybridize with K1 DNA.

A primer of the invention may be said to specifically amplify Kell DNA if it binds to or causes elongation through a defined region of Kell DNA. Thus, a primer specifically amplifies K1/K2 DNA if it preferentially amplifies a region including the K1/K2 locus. Accordingly, a K1/K2 primer amplifies DNA including the K1/K2 locus but nonselectively amplifies both K1 DNA and K2 DNA. On the other hand, a primer is specific for a particular allele, such as K1 (K1 primer), if it specifically amplifies only DNA associated with that allele, such as K1 DNA, while a primer specific for K2 (K2 primer) specifically amplifies only K2 DNA. Similar considerations apply to other polymorphisms in the Kell system.

It is particularly preferred that probes be capable of differentiating two alleles which differ by no more than a single nucleotide modification. It is known in the art that it is possible to control the specificity of hybridization by selectively constructing probes and primers and by adjusting hybridization or other experimental conditions. There may be situations, however, in which it would be desirable to employ probes which hybridize somewhat less selectively. Accordingly, it is within a particular context that a probe or primer according to the invention is said to be "substantially complementary" to a specific Kell sequence. That is, if the situation demands high precision, a probe or primer is substantially complementary to a target sequence if there exists only a very small probability that the oligomer will bind with a sequence other than the specific target sequence. In other situations, a probe or primer may be deemed to be substantially complementary to a target sequence if the probability of a unique hybridization is substantially less than 1.0. Thus, a probe or primer of the invention may be "substantially complementary" to a target region if it is either exactly complementary, or even only partially complementary, to the target region, depending on the required stringency of the method parameters.

Thus, the invention provides probes and primers which hybridize with parts or all of the Kell locus. Such probes are useful when the Kell gene or transcripts thereof are desired to be characterized. Moreover, the invention provides probes and primers which include part or all of one or more introns in the Kell locus in chromosomal DNA. Such probes are useful when the Kell gene itself is desired to be characterized and additional information is desired to be obtained about the structure of the gene in a particular individual.

The probes or primers of the invention may also include, as part of their nucleotide sequences, regions which are not substantially complementary to any region adjacent to or near a target sequence. Thus, in any probe or primer of the invention, at least a part of the probe or primer is substantially complementary to a target segment.

"Amplification" refers to any molecular biology technique for detection of trace levels of a specific nucleic acid sequence by exponentially amplifying a template nucleic acid sequence. Techniques are known for the amplification of DNA as well as RNA, and for the generation of amplified RNA from DNA and vice versa. In particular, amplification techniques include such techniques as polymerase chain reaction (PCR), and ligase chain reaction (LCR). The PCR is known to be a highly sensitive technique, and is in wide use. The LCR is known to be highly specific, and is capable of detecting point mutations. In certain circumstances it is desirable to couple the two techniques to improve precision of detection. The PCR is a well-known technique and is described, for example, in Innis et al. (Ref. 34). The LCR is more recently developed and is described in Landegren et al. (Ref. 35) and Barany et al. (Ref. 36). An LCR kit is available from Stratagene. Other amplification techniques may be expected to be employed according to the method of the invention.

"Primer" refers to an oligonucleotide, whether natural, cloned, or synthetic, which is capable of initiating nucleic acid synthesis for exponential amplification of a target or template nucleic acid sequence by an amplification technique. For PCR the primer acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. For LCR the primer is capable of annealing to a target nucleic acid and of being ligated to an adjacent primer to serve as a template for amplification. Also for purposes of the LCR, the primer generally includes paired sets of adjacent, complementary oligonucleotides which can anneal to single stranded target molecules and ligate them together. For LCR amplification of DNA, the primers include two sets of adjacent, complementary oligonucleotides.

A primer is preferably an oligodeoxyribonucleotide and is single stranded for maximum efficiency in amplification, but may also be double stranded. If double stranded, the primer is generally first treated to separate its strands before being used to prepare extension products. Typically. LCR primers are double stranded. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template. An example of a non-complementary sequence which may be incorporated into the primer is a sequence which encodes a restriction enzyme recognition site (see U.S. Pat. No. 4,800,159).

"Primer", as used herein, may refer to more than one primer, particularly in the case where there is some ambiguity in the information regarding one or both ends of the target region to be amplified. For instance, if a nucleic acid sequence is inferred from a protein sequence, an operable "primer" may actually include a collection of primer oligonucleotides containing sequences representing some or all of the possible codon variations based on the degeneracy of the genetic code. One of the primer oligonucleotides in this collection will be homologous with the end of the target sequence. Likewise, if a "conserved" region shows significant levels of polymorphism in a population, mixtures of primers can be prepared that will amplify adjacent sequences.

A primer or probe according to the invention can be labeled, if desired, by incorporating a label detectable by spectroscopic, photochemical, biochemical, immunochemical, or chemical means. For example, useful labels include $^{32}$P, fluorescent dyes, electron-dense reagents, reporter molecules such as enzymes (as commonly used in ELISAs), biotin, or haptens or proteins for which antisera or monoclonal antibodies are available. A label can also be used to "capture" the primer, so as to facilitate the immobilization of either the primer or amplified DNA on a solid support.

"Oligonucleotide" or "nucleic acid oligomer" refers to primers, probes, nucleic acid fragments to be detected, nucleic acid controls, and unlabeling blocking oligomers and is defined as a molecule comprised of two or more deoxyribonucleotides or ribonucleotides. The nucleic acid oligomers of the invention may be single-stranded oligomers of deoxyribonucleic acid (DNA) or ribonucleic acid (RNA). The exact size of an oligonucleotide will depend upon many factors and the ultimate function or use of the oligonucleotide. The oligodeoxyribonucleotides and oligoribonucleotides may be obtained or derived by known methods from natural sources. Alternatively, the oligonucleotides may be produced synthetically according to methods known in the art. Such methods include, for example, cloning and restriction of appropriate sequences and direct chemical synthesis by a method such as the phosphotriester method of Narang et al. (Ref. 37); the phosphodiester method of Brown et al. (Ref. 38); the diethylphosphoramidite method of Beaucage et al. (Ref. 39); and the solid support method in U.S. Pat. No. 4,458,066. It is preferred that the oligomers be at least substantially purified to avoid introduction of artifacts into the genotype determination method.

The invention also provides oligonucleotides which are structurally homologous to a part or all of genetic material related to or derived from the Kell gene. An oligomer is said to be "substantially homologous" to another if, despite variations in the nucleotide sequence, the oligomer encodes an amino acid sequence which is phenotypically identical to the sequence to which it is being compared. Thus, sequences are not substantially homologous if, when expressed, the sequences result in shift in Kell phenotype. On the other hand, two sequences encoding the same locus or sublocus are substantially homologous if they are not identical but nonetheless encode sequences which correspond to parts or all of phenotypically non-differentiable variants of the Kell protein. Accordingly, sequences which encode K1 domain and sequences which encode the K2 domain are not substantially homologous, even though they differ, as has now been discovered, by a single nucleotide substitution. In contrast, variations in nucleotide sequence which do not result in an amino acid shift in the encoded gene product may be substantially homologous.

The method of the invention is a molecular genetic method which permits the determination of one or more aspects of the Kell genotype of a subject. The method generally involves obtaining DNA or other nucleic acid from a biological sample from a human subject or patient. Typically, the method requires a blood sample, but other types of tissue samples which contain erythroid tissue are useful. The method may be employed to test any individual for Kell genotype. In a particularly preferred embodiment, however, the invention provides a method for determining Kell blood group genotype in a fetus. In this embodiment, the preferred tissue sample includes a sample of amniotic fluid. It is understood, however, that such samples can be obtained from sample libraries or tissue archives such as blood banks, or from forensic evidence, etc. Accordingly, the method may be used on a unique or irreplaceable sample or may be used to screen large numbers of samples.

In general, the method of the invention includes generating at least one characteristic nucleic acid product from a nucleic acid sample. The sample nucleic acid is obtained or derived from a subject for whom Kell genotype is desired to be determined, and preferably includes a nucleotide sequence which contains a Kell polymorphism locus, although the exact sequence or structure need not be well defined beforehand. In preferred embodiments the nucleic acid sample includes genomic DNA of the subject.

The method of the invention generates a nucleic acid product, characteristic of specific Kell genotype, in an amount sufficient to permit characterization of at least one aspect of Kell genotype. Preferably, the method of the invention generates a characteristic nucleic acid product which permits the differentiation of alleles of a Kell polymorphism, such as K1 and K2; K6 and K7; and K3, K4, and K21; or which permits the differentiation of K10 from the wild-type K(−10).

In one preferred embodiment, the diagnostic method of the invention includes exposing Kell DNA to a restriction enzyme which differentially cleaves or digests nucleic acid containing a Kell polymorphism locus. Typically, the restriction enzyme generates a nucleic acid product which includes at least one restriction fragment which is distinctive in size and can be associated with a specific Kell allele on a consistent basis. For example, the restriction enzyme may digest one allele of a polymorphism set while failing to digest other alleles of the set. Alternatively, the restriction enzyme cleaves alleles in the set except for one which is left intact and is recognizable on that account.

Numerous restriction enzymes are known in the art, and any restriction enzyme which produces at least one distinctive or characteristic fragment in this way may be employed according to this embodiment of the method of the invention.

For K1/K2 differentiation, a preferred restriction enzyme is BsmI which cuts at a restriction site which, it has now unexpectedly been found, occurs in K1 DNA but not in K2 DNA. Thus, BsmI cleaves K1 DNA while leaving K2 DNA intact. For the K6/K7 polymorphism, preferred restriction enzymes include MnlI and DdeI, which unexpectedly cleave K7 DNA but not K6 DNA. For K10, a preferred restriction enzyme is AccI, which unexpectedly cleaves K10 DNA, but not wild-type K(−10) DNA at that locus. In the K3/K4/K21 group, preferred restriction enzymes include NlaIII, which unexpectedly cleaves only K3 (Kp$^a$) DNA, and/or PvuII, which unexpectedly cleaves only K21 (Kp$^c$) DNA; K4 (Kp$^b$) DNA remains uncleaved by either of these enzymes. Combinations of these or other enzymes may be employed as desired.

In another preferred embodiment, the diagnostic method of the invention involves differentially amplifying DNA including a Kell polymorphism locus. Preferably, the Kell DNA is amplified by means of a primer which differentially amplifies a specific allele in a set of alleles associated with a Kell polymorphism. For example, by carefully selecting an appropriate amplification primer, DNA containing a K1 locus may be amplified to produce a distinctive amplified product, while DNA containing a K2 locus is not amplified to any substantial degree. Alternatively, a set of primers may be employed which produce distinctive set of amplified products which may be analyzed to determine the presence or absence of alleles. For example, a K1 specific primer may produce a product characteristic of K1 genotype and a K2 primer may produce a product characteristic of the K2 genotype. Other alleles of other Kell polymorphisms may also be differentially amplified by selecting appropriate primers.

Any combination of primers may be employed according to this embodiment provided that the amplification product(s) permits characterization of a desired aspect of Kell genotype. Preferred primer sets include: primers which differentially amplify K1 and K2 DNA; primers which differentially amplify K6 and K7 DNA; primers which differentially amplify K10 and K(−10) DNA; primers which differentially amplify K3, K4, and K21 DNA; or combinations thereof.

It is among the advantages of this approach that, by using appropriate primer combinations, specific fragments of DNA are amplified to provide products in an amount sufficient to characterize Kell genotype without any requirement for digesting the DNA with restriction enzymes. Nonetheless, it is within the invention to employ primers which provide differentiating sets of DNA fragments, and to supplement the differentiation of products and consequent characterization of Kell genotype by means of selectively cleaving the fragments with restriction enzymes. This may be particularly helpful in situations where some fragments are not completely separable or differentiable due to limitations of technology, while selective cleavage of the fragments resolves an ambiguity.

The diagnostic methods of the invention typically yield a nucleic acid product, such as digested DNA or RNA fragments or amplified DNA or RNA products, in amounts sufficient to permit the characterization of Kell genotype. The pieces of nucleic acid permit such characterization since they carry information in their sequences and/or sizes which permits at least some of the fragments to be differentiated from the others. The differentiating characteristics of the fragments may be exploited by any methods known in the art.

For example, fragments may be separated from each other on the basis of physical characteristics. A highly preferred differentiating characteristic is molecular weight. Specific and characteristic molecular weights of the fragments are directly determined by site-specific cleavage by restriction enzymes. Particular primers may generate amplification products having specific molecular weights. The fragments may be separated from one another by methods such as polyacrylamide gel electrophoresis which relies on molecular weight as well as net molecular charge for separation. Such techniques produce informative patterns of fragments permitting determination of Kell genotype.

Kell nucleic acid products may also be differentiated from one another on the basis of their sequence identity. Specific probes may be employed according to known methods to hybridize specifically or uniquely with specific fragments. By the differential labeling of several probes, the presence or absence of particular Kell polymorphism-specific fragments may be established. Alternatively, following separation of fragments, their detection may be enabled by marking or some or all of the fragments specifically or non-staining specifically according to known methods. Various sequence non-specific marker substances are known, such as ethidium bromide.

Hybridization probes may be employed to detect the presence or absence of specific Kell nucleic acids in a testable system. Diagnostic tests based on hybridization techniques can be both extremely specific and highly sensitive, providing information characterizing Kell genotype. Such techniques are described, for example, in Glick B. R. and Pasternak J. J., *Molecular Biotechnology: Principles and Applications of Recombinant DNA*, ASM Press, Washington, D.C., pp. 192–201 (1994) (Ref. 40).

In a preferred embodiment, the diagnostic method includes:
 (a) obtaining DNA from a tissue sample from a patient;
 (b) amplifying the DNA by polymerase chain reaction using a primer or primer set which specifically amplifies DNA characterizing or determining a specific Kell polymorphism;
 (c) selectively cleaving the amplified DNA by a restriction enzyme which differentially cleaves Kell DNA to produce a pattern of DNA fragments; and
 (d) separating the DNA fragments according to molecular weight to form a pattern of DNA fragments, wherein the pattern of DNA fragments provides specific information characterizing the Kell genotype of the patient with regard to the specific Kell polymorphism.

In another preferred embodiment, the diagnostic method includes:
 (a) obtaining DNA from a tissue sample from a patient;
 (b) amplifying the DNA by polymerase chain reaction using a primer or primer set comprising at least one primer which amplifies only DNA of one allele in a Kell allelic set; and
 (c) separating the amplified DNA according to molecular weight to form a pattern of DNA fragments, wherein the pattern of DNA fragments provides specific information characterizing the genotype of the patient with respect to the specific Kell polymorphism.

In still another embodiment, the diagnostic method includes:
 (a) obtaining DNA from a tissue sample from a patient;
 (b) amplifying the DNA by ligase chain reaction using a primer set which amplifies only DNA of a Kell allelic set to produce a pattern of DNA fragments; and
 (c) separating the DNA fragments according to molecular weight to form a pattern of DNA fragments, wherein the pattern of DNA fragments provides specific information characterizing the genotype of the patient with respect to the Kell polymorphism.

Moreover, in another embodiment, the diagnostic method includes:
(a) obtaining DNA from a tissue sample from a patient;
(b) selectively cleaving the DNA by a restriction enzyme which differentially cleaves DNA of at least one allele in a Kell allelic set to produce a pattern of DNA fragments;
(c) amplifying the pattern of DNA fragments by polymerase chain reaction using a primer or primer set which amplifies only DNA of the allelic set; and
(d) separating the amplified DNA according to molecular weight to form a pattern of DNA fragments,
wherein the pattern of DNA fragments provides specific information characterizing the genotype of the patient with respect to the Kell polymorphism.

In yet another embodiment, the invention provides a diagnostic method which includes:
(a) obtaining DNA from a tissue sample from a patient;
(b) exposing the DNA to a restriction enzyme which differentially cleaves K1 DNA and K2 DNA to produce a pattern of DNA fragments;
(c) separating the DNA fragments according to molecular weight to form a pattern of DNA fragments; and
(d) determining the presence of K1 DNA and/or K2 DNA using detectably labeled Kell cDNA probes;
wherein the pattern of DNA fragments provides specific information characterizing the K1/K2 genotype of the patient. Such methods include, for example, Southern blot methods such as are known in the art.

In an alternative embodiment, the invention provides a diagnostic method for detecting a target nucleic acid which is specific to K1 or K2. In this embodiment, the method includes:
(a) obtaining a nucleic acid fraction from a tissue sample from a patient;
(b) ascertaining the presence in the nucleic acid fraction of a target nucleic acid encoding at least a part of the Kell protein and including the site characterizing the K1/K2 polymorphism. In this method, the presence of the target nucleic acid is ascertained by means of a probe nucleic acid which includes a nucleic acid sequence which is known to specifically bind to or hybridize with K1 DNA or K2 DNA or transcripts thereof. The probe nucleic acids useful in this method may be any of the Kell-based oligomers described herein, including those which are detectably labeled or attached to a substrate. This method may be used to detect target nucleic acids which are chromosomal or genomic DNA, mRNA, and cDNA, as well as other related forms of nucleic acid encoding the K1/K2 domain of the Kell protein. Such methods include, for example, dot blot methods such as are known in the art.

In still another embodiment, the invention provides a method for the determination of Kell blood group genotype. In this embodiment, the method includes the steps of:
(a) selecting a probe nucleic acid sequence substantially corresponding to at least part of a known Kell exon or a transcript thereof, wherein the known Kell exon comprises a Kell polymorphism locus and codes for a specific Kell allele;
(b) contacting a sample nucleic acid sequence obtained or derived from a subject, the subject having an unknown phenotype with respect to the Kell polymorphism locus, with the probe nucleic acid sequence under conditions which permit hybridization when the nucleic acid sequences are significantly complementary; and
(c) measuring an amount of hybridization between the probe nucleic acid sequence and the sample nucleic acid sequence.

In this embodiment, the detection of an amount of hybridization corresponding to an amount resulting from significantly complementary sequences indicates that the subject possesses the specific Kell allele under investigation. On the other hand, detection of an abnormally low amount of hybridization indicates that the subject lacks the specific Kell allele being investigated.

The invention further provides recombinant expression vectors which carry Kell nucleic acid sequences. Such vectors permit transformation of cells, particularly eukaryotic cells such as yeast and human cells, to cause such cells to express a heterologous protein product. The invention provides expression vectors which include a nucleic acid sequence which encodes at least a part of the Kell protein including a part of the protein which encodes a site of Kell polymorphism. In particular, the invention provides expression vectors which carry K1 cDNA permitting transformation of cells to produce transformed cells or transformants which express K1 protein on their cell surfaces. Vectors are also provided which carry K6 cDNA, as well as vectors which carry K10 cDNA, and vectors which carry K3 or K21 cDNA, permitting transformation of cells to express K6, as well as K10, and K3 and K21, respectively. The invention also provides stable cell lines which have been modified (i.e., transformed) to express protein on its cell surface, as well as a method for transforming a cell line to express such protein. With respect to the K1 expression, such protein preferably includes at least the K1 domain, and more preferably, the protein is K1 protein. Similarly, with respect to expression of K6, K10, as well as K3 and K21, the expressed protein preferably includes the K6, the K10, the K3 or the K21, domain, respectively; more preferably, the protein is K6, K10, K3, or K21 protein, respectively. Methods for preparing recombinant expression vectors, and for transforming cell lines using such vectors are known in the art, and are described generally in Glick B. R., and Pasternak J. J., *Molecular Biotechnology: Principles and Applications of Recombinant DNA* ASM Press, Washington, D.C. (1994) Chapter 5 (Ref. 40), the disclosure of which is incorporated herein by reference.

The Kell genotype determination method of the invention is of particular utility in the determination of the fetal Kell genotype. The molecular genetic method described herein can easily be applied to DNA samples obtained from amniotic fetal cells and is useful in determining the Kell genotype of the fetus. The methods of the invention are also useful in a variety of other situations in which molecular genetic information about a person is desired. For example, the methods of the invention are useful in situations in which it is desired to obtain information concerning the identity of an individual from forensic samples. Alternatively, the methods of the invention are useful for obtaining genetic information enabling the determination of paternity in those situations in which paternity is in doubt or dispute. In addition, the methods of the invention are useful for the determining the Kell genotype of a recipient of a blood transfusion, as well as for the screening of stored blood for Kell genotype, to avoid transfusion incompatibility. The peptide based methods of the invention are particularly useful in determining alloimmunization of a person to a Kell antigen, such as K1. Information about such alloimmunization would be expected to be useful in advising women about risk entailed in future pregnancies. Other applications of the methods of the invention will suggest themselves to the skilled artisan.

In addition, the genotype characterization method of the invention may be performed selectively so as to permit description of some or all of the Kell family of alleles. The method may also be performed in conjunction with the determination of phenotype of some or all of the Kell family of antigens. Thus, it is possible to confirm Kell genotype by employing serological testing in conjunction with genomic analysis using a restriction enzyme. Such serological testing steps may be performed either prior to, in parallel with, or after the prescribed genomic testing. Moreover, the planning of testing procedures may be based on preliminary partial results which rule out or imply the possibility of, for example, certain rare genotypes. It may also be desirable to perform genotype testing for other markers or blood groups together with the Rh genotyping method of the invention. For example, the genotyping method described in U.S. application Ser. No. 08/553,888 filed Nov. 6, 1995, relating to the determination of Rh genotype, may be performed in conjunction with the method of the invention to provide counsel as to a broader spectrum of possible difficulties in pregnancy. In general, the diagnostic method, compositions and kits of the invention are expected to be employed in conjunction with a wide variety of known medical tests and assays to enhance and complement the information available to the clinician concerning a patient. See e.g., Walker R. H. et al., eds., *Technical Manual*, 10th ed., American Association of Blood Banks, Arlington, Va. (1990) (Ref. 41).

The following examples are intended to assist in a further understanding of the invention. The particular materials and conditions employed are intended to be further illustrative of the invention and are not limiting upon the reasonable scope thereof.

For each of the examples described herein, the molecular biology techniques employed were performed generally in accordance with methods accepted in the art. See, for example, Sambrook et al. (Ref. 42), and Innis et al. (Ref. 34), the disclosures of which are incorporated herein by reference.

EXAMPLE 1

The organization of the KEL gene was determined using the following procedure.

Screening of a Genomic Library

A human placental genomic DNA library constructed in EMBL3 Sp6/T7 was obtained from Clontech, Inc. (Palo Alto, Calif.). The genomic DNA library was constructed by partially digesting human placenta genomic DNA with Sau3A1 and ligating the fragments into the BamHI site of the vector. For screening, the λ phage library was grown in either NM528 or LE392 strain of *E. coli* and plated. The DNA was lifted on Hybond#-N+ membranes (Amersham Co., Arlington Heights, Ill.) and hybridized with Kell cDNA probes according to standard procedures (Ref. 43). The cDNA probes were labeled with $^{32}$P by random primer extension using a commercial kit (Boehringer Mannheim Inc., Indianapolis, Ind.). The specific activity of the probes was approximately $1\times10^8$ cpm/µg. Fourteen positive clones were isolated.

Characterization of Exons and Introns

Of the 14 positive clones identified, five (λ2, λ8, λB, λF, and λE) were selected for further characterization. Two of the clones (λ2 and λE) span most of the Kell gene and cover about 21.5 Kb (see FIG. 1). Clone λ8 was studied because it extended more of the 5' flanking region and also served to reconfirm the sequences determined from clone λ2. Clones λB and λF were used because they overlapped with λE, and in addition a small segment of λF overlapped with the 3' end of λ2 (see FIG. 1)

These five clones were initially mapped by digestion with XhoI plus PstI and with XhoI plus EcoRI, followed by Southern blot hybridization using different oligonucleotides specific for various locations in the Kell cDNA sequence. The genomic clones were then digested with the following enzymes: PstI, EcoRI, BamHI, BglII and XhoI, either individually or in combination. The individual gene fragments were subcloned into PUC18 (Gibco BRL, Gaithersburg, Md.) or pGEM-3Zf(+) (Promega Co.) and sequenced on an automated 373A DNA sequencer (Applied Biosystems, Inc., Foster City, Calif.). The exons, determined in relation to the Kell cDNA sequence, and their flanking regions, were fully sequenced, as were some short introns. With one exception, the long introns were sized by PCR using primers from the flanking regions of the introns. The longest intron, between exons 10 and 11, was partially sized using primers from known intron sequences obtained from λ2 and λE, using a YAC clone as template. (Seven yeast artificial chromosome (YAC) clones were separately isolated by PCR specific for KEL exon 6 from a YAC resource enriched for chromosome 7 DNA.) This area of the intron was confirmed by PCR using human genomic DNA as template.

Restriction Enzyme Mapping and Southern Blot Analysis of the Genomic Clones

Subclones were mapped with BamHI, EcoRI and PstI. The different sizes of digested DNA were resolved by agarose gel electrophoresis. The DNA fragments were in some cases further analyzed by Southern blots using $^{32}$P-labeled oligonucleotides derived from different locations of Kell cDNA and also identified with available sequences of the subcloned gene fragments. The combination of these procedures allowed a restriction map of BamHI, EcoRI and PstI to be constructed. Sequence analysis of the subcloned Kell gene fragments from these 5 genomic clones revealed that the human KEL gene contains 19 exons ranging in size from 63 bp (exon 7) to 288 bp (exon 19) which includes a 3' untranslated region.

FIG. 1 shows the newly determined structure of the human Kell gene (KEL) with restriction enzyme sites. The position of exons are shown as dark boxes and the introns are shown as lines connecting the exons. The vertical lines of different heights mark the restriction enzyme sites in the Kell gene. The λ phase, genomic clones are shown at the bottom of the diagram (λ2, λ8, λE, λB and λF). Two of the genomic clones from the commercial genomic library, clones λB and λF, gave inconsistent sequences when compared to other clones (λ2 and λ8). The 5' segments of clones λB and λF should be identical to the 3' segments of λ2 and λ8 but sequence analysis showed that they were different. The reason for this is not known, but could be due to ligation of DNA material during the preparation of the genomic library. These areas of difference are depicted in FIG. 1 by broken lines. The restriction enzyme digested products which were subcloned and analyzed are shown above the genomic clones. Each sub-clone shows the restriction enzymes used and the genomic clones from which it was derived. Four PCR-derived sub-clones (PCR25, PCR6, PCR1 and PCR20) are also shown. In parenthesis each PCR product shows the genomic clone from which it was amplified. A small segment of the large intron not covered by clones λ2, λ8 and λE was determined by sequencing PCR products (PCR6) from a YAC clone (yWSS679) and from the genomic DNA. This strategy was employed even though the λF clone covers the 3' end of the λ2 clone. This allowed us to cover the entire Kell gene and to size the intron between exons 10 and 11 without ambiguity.

All exon/intron splice junctions were found to contain the 5' donor -gt and the 3' acceptor -ag sequences. The introns ranged in size from 93 bp to approximately 6 kb. there were 6 introns which were longer than 1 kb (FIGS. 1 and 2). The long introns were not fully sequenced, but were sized by PCR. There was ambiguity in analyzing the intron between exons 10 and 11 because the 5' region of clones λB and λF, which were expected to overlap with the 3' region of clones λ2 and λ8, did not. These ambiguous areas of clones λB and λF are shown as dotted lines in FIG. 1. Because of this uncertainty, the small gap of the gene not covered by clones λ2 and λE was bridged by PCR amplification of YAC clone yWSS679 containing the Kell gene (FIG. 1). The size of this PCR amplified region was further confirmed by PCR of genomic DNA obtained from a person of common Kell phenotype using the same primers used for the YAC clone.

All of the exons were sequenced and compared to that of a full length Kell cDNA isolated from a human bone marrow library obtained from Clontech Laboratories, Inc. The Kell phenotype of this library was unknown. Differences were noted in 4 bases in exon 3 as compared with the published sequence for Kell cDNA (Ref. 14). These differences were due to sequencing errors in the original study. The corrected sequences were submitted to EMBL/GenBank Updates (National Center for Biotechnology Information, Bethesda, Md.) under accession No. M64934. One notable difference is a base substitution in the membrane-spanning region, which encodes a leucine instead of proline. The corrected base sequences are shown in bold type in FIG. 2.

FIGS. 2A–2D illustrate the sequence of the individual exons encoding human Kell protein with the immediate intron flanking splice junction sequences. The base sequences of the individual exons are shown in capital letters and the flanking intron sequences in small letters. The amino acid sequences encoded by the exons are shown above the base sequences. The numbers on the left-side, below the indicated exons, refer to the base numbers from the cDNA. The other numbers on the left and right sides indicate the amino acid residues and the bases, as previously described for the cDNA (Ref. 25). Intron sizes are specified at the end of the exons. 5' and 3' splice sites are also shown.

Since the Kell phenotype of the person from whom the genomic DNA library was constructed is unknown, we isolated RNA from peripheral blood of a person of known common phenotype (K:−1,2,−3,4,−6,7). cDNA was prepared by RNA-PCR and sequenced according to methods known in the art. The deduced amino acid sequence was identical to that shown in FIG. 2 as obtained from the Clontech genomic library. In the person of known phenotype, C to T base differences occurred in two locations (nt 1656 and 1664), but these substitutions did not change the predicted amino acids.

Of interest is that exon 1 includes the 5' untranslated region and codes for only initiation methionine. The single membrane spanning region is located in exon 3 and the pentameric sequence (HELLH) (SEQ ID NO:59) which conforms with a consensus sequence (HEXXH) (SEQ ID NO:60) found in the active sites of zinc neutral endopeptidases (Ref. 43) is in exon 16 (FIG. 2).

The coding region of the native protein is present in 18 of the 19 exons; the first exon contains the 5' untranslated region and the initiation methionine. Other examples having only the initiation codon in the first exon are known (Ref. 44). The single transmembrane region is encoded in exon 3 with exons 4 to 19 encoding most of the extracellular portion. The HEXXH (SEQ ID NO:60) motif, which is unique to zinc metallopeptidases (Ref. 29) is encoded in a 68 bp exon (exon 16). In addition to the consensus pentameric sequence, Kell has sequence and structural homology with a family of membrane-associated zinc neutral endopeptidases (EC24.11) (Ref. 25) of which the enkephalinases and CALLA are examples (Refs. 45–46). The CALLA gene is larger than the Kell gene, about 80 kb, and is composed of 24 exons (Ref. 47). In CALLA the putative enzyme active site is encoded in exon 19 and a comparison of base sequences of exons 18 and 19 of CALLA with exons 15 and 16 of Kell shows 54.5% base identity.

EXAMPLE 2

Transcription Initiation Site

The transcription initiation site of the KEL gene was determined by the rapid amplification of cDNA ends (5' RACE) employing a human fetal library (5' RACE Ready™ cDNA library, Clontech laboratories, Palo Alto, Calif.). The source of poly (A)$^+$ RNA was normal liver pooled from 2 female Caucasian fetuses, 22 and 26 weeks of gestation. The single stranded cDNA library was made by reverse transcription, using random hexamers as primers. An oligonucleotide anchor 3'-NH$_3$-GGA GAC TTC CAA GGT CTT AGC TAT CAC TTA AGC AC-p-5' (SEQ ID NO:6) was ligated to the cDNA. For the 5' RACE, 2 sets of nested PCR reactions were carried out, using primers from 2 different locations on Kell cDNA (nt 132 and nt 178). In the first PCR, 5' RACE Ready™ cDNA was used as template. The primers used for one set (PCR1) included the anchor primer provided by Clontech (5'-CTG GTT CGG CCC ACC TCT GAA GGT TCC AGA ATC GAT AG-3' ) (SEQ ID NO:7) and Kell anti-sense primer (5'-CTC GGC TCT TCC TCA CTT TGG TCC-3', nt 132) (SEQ ID NO:8). For the other set (PCR2), the primers included the Clontech anchor primer (SEQ ID NO:7) and Kell anti-sense primer (5'-CTC TTG GCT CCA GAG AGT TCC CAT-3', nt 178) (SEQ ID NO:9). For the second nested PCR the products of the first PCR reactions were used as template and the Clontech anchor primer (SEQ ID NO:7) was again used as sense primer for both parallel reactions. In PCR1 a Kell anti-sense primer (5'-CCC ACC TTC CAT CTG TCT ATC TTC-3', nt 109) (SEQ ID NO:10) was used. For PCR2, the Kell anti-sense, nt 132, (SEQ ID NO:8) was used.

PCR was performed in an automated thermocycler (Minicycler, MJ Research Inc. Watertown, Mass.) using an initial cycle of 94° C. for 3 minutes, 62° C. for 1 minute, and 72° C. for 30 seconds. In cycles 2 to 30 the conditions were 94° C. for 30 seconds, 62° C. for 30 seconds and 72° C. for 30 seconds. In the last cycle the polymerization step at 72° C. was extended to 10 minutes. The final concentrations of reagents were 50 mM KCl, 10 mM Tris-HCl (pH 9.0), 3 mM MgCl$_2$, 400 nM of each primer, 200 μM of each dNTP, 0.1% Triton-X100, and 2.5 units of taq polymerase, in a final volume of 50 μL. The "hot start" method using Ampliwax™ from Perkin Elmer (Branchburg, N.J.) was employed. The PCR products were separated by electrophoresis in 0.8% low melting agarose gels, eluted and directly ligated to pT7-Blue(R) plasmid vector from Novagen (Madison, Wis.) and transformed in DH5αF' strain of E. coli.

Each primer yielded 3 different size products. These products were subcloned and sequenced. The largest product from each PCR reaction had a 5' end at 120 bp upstream from the initiation codon. The 2 shorter PCR products ended at 81 and 30 bp upstream from the initiation codon.

FIG. 3 illustrates the nucleotide sequence of the KEL 5' flanking region showing exon 1 and possible cis regulatory elements. A 185 bp region upstream from the probable cap site is shown. The three possible transcription initiation sites are marked by ▽. Consensus sequences for GATA-1, Sp1 and a CACCC region are boxed. The region −176 to −1, which was copied by PCR and placed in a CAT-expression vector is shown. The initiation methionine is in bold letters.

Three possible transcription initiation sites were found using the 5' RACE procedure and poly (A)+ RNA from fetal liver. The first of these cap sites, located 120 bp upstream from the initiation ATG, is also the 5' end of a cDNA cloned from a human bone cDNA library (Ref. 25) the other 2 sites are 81 and 30 bp upstream from the initiation codon. All 3 sites were obtained using 2 different Kell cDNA anti-sense primers. Although all 3 locations are purine bases and could act as transcription initiation sites. It is also possible that those at 81 and 30 bp upstream from the ATG are artifactual due to incomplete reverse transcription. This is unlikely given that random hexamers were used to prepare the cDNA library. However, secondary RNA structures can also cause premature termination of reverse transcription.

EXAMPLE 3
Analysis of 5' Flanking Region

The constitution of the 5' flanking region was obtained by DNA sequencing of sub-clone λ8, following digestion with PstI (see FIG. 1). The 5' flanking region was determined to span nucleotides −176 to −1.

FIG. 5 shows a 185 bp sequence upstream from the first possible initiation transcription site. Analysis of this region, and of exon 1, indicates that there are no TATA sequences but several other possible transcription factor binding sites were noted. At least 2 GATA-1 sites are present close to a CACCC box. Sp1 and GATA-1 sequences are present in exon 1. The 5' flanking region contains purine-rich regions. These areas of interest are shown in FIG. 3.

The transcriptional activity of the 5' flanking region from −176 to −1 (FIG. 3) was determined by CAT assay in transfected K562 cells as compared to the promoter-less pCAT vector. In this procedure, a PCR product spanning nucleotides −176 to −1 relative to the first cap site was subcloned into PCAT basic vector obtained from Promega Co. Cells of the erythroleukemic cell line K562 were then transfected using the lipofectin method. Construction of the CAT-vector, transfection and chloramphenicol acetyltransferase (CAT) activity were assayed following the protocol provided by Promega Co. CAT enzymatic activity was measured using [$^{14}$C]-chloramphenicol (50–60 mCi/mmol, Amersham Co., Arlington Heights, Ill.). The reaction products were measured by liquid scintillation spectrometry and analyzing the reaction products by thin layer chromatography. As a negative control the pCAT basic vector without promoter was used. All cell extracts were normalized by protein analysis in order to compare values.

Introduced in front of a CAT reporter gene, the 5' flanking region exhibited promoter activity in the erythroleukemic cell line K562. pCAT vector with the 5' flanking region was found to express approximately 0.8 units of CAT activity per milligram of cell extract protein. A unit of CAT enzyme activity is defined as the amount of enzyme required to transfer 1 nmol of acetate of chloramphenicol in 1 minute at 37° C. FIG. 4 shows CAT activity of the 5' flanking region. An autoradiogram, exposed for 48 hours, is shown. Lane 1 has pCAT vector with the 5' flanking region and lane 2 has pCAT basic vector without promoter. The radioactive butyrylated chloramphenicol is indicated as "bCm", and the unreacted chloramphenicol is indicated as "Cm".

The putative promoter region does not contain the typical TATA box usually located −25 to 30 nt relative to the cap site (Ref. 48). However, as in several erythroid specific genes, consensus sequences for GATA-1 factor were found in the promoter region. In addition, possible Sp1 and GATA-1 binding sites were noted in exon 1. It is not known whether GATA-1 and Sp1 regulate KEL gene expression but GATA-1 is common in erythroid genes (Refs. 49–55) and is known to be expressed at low levels in hematopoietic progenitor cells and up-regulated during erythroid maturation (Refs. 56–58). If these transcription factors define erythroid tissue specificity it will be in agreement with our Northern blot studies which detected Kell transcripts in bone marrow and fetal liver but not in several non-erythroid tissues (Ref. 8).

EXAMPLE 4
Analysis of the 3' End

Exon 19 is the largest Kell exon, encoding the C-terminal 53 amino acids and containing the 3' untranslated region with a polyadenylation signal 100 bp downstream of the termination codon. Previous Northern blot analysis showed that the major Kell transcript in bone marrow and fetal liver is 2.5 kb although smaller amounts of larger mRNAs, notably 6.6 kb, also were observed (Ref. 8). In originally cloning the Kell cDNA from a human bone marrow library, we isolated a cDNA with a large (3 kb) 3' untranslated region (Ref. 25).

To determine the 3' end structure of the Kell gene, RNA was isolated from peripheral blood as described by Goosens et al. (Ref. 59) and cDNA was prepared by reverse transcription and PCR amplification using a Perkin Elmer RNA PCR kit (Roche Molecular Systems, Inc., Branchburg, N.J.). First strand synthesis was initiated using an anchored oligo d(T)$_{16}$ primer. PCR amplification of the 3' end of Kell cDNA was performed using the anchor primer and an oligonucleotide primer from the coding sequence of Kell cDNA. The anchor antisense primer used was oligo 5'-GACTCGAGTCGACAACGTT(T)$_{16}$-3' (SEQ ID NO:11) and the sense primer from the 3' end coding sequence of Kell cDNA was 5'-ATGGGGAGACTGTCCTG-3' (SEQ ID NO:12).

A PCR product of about 400 bp was obtained and was sub-cloned and sequenced. The 3' end sequences of different sub-clones are shown in FIG. 5. The base sequences, prior to the poly A region, of cDNA clones from a human bone marrow library (top) and from peripheral blood of a person with common Kell phenotype (bottom) are shown. (A) indicates the poly A region.

The 3' end sequences of four different subclones, obtained from peripheral blood are shown in the bottom portion of FIG. 5. All four of the subclones had identical sequences from the termination codon to the polyadenylation signal (AATAAA). At the 3' end, the base sequences differ slightly in length before the start of the poly A sequence. The distance between the polyadenylation signal and the cleavage site is known to be variable (Ref. 60). Similar variations in 3' end sequences were observed in 3 different Kell cDNAs obtained from a human bone marrow cDNA library (Clones 185, 182 and 190).

Only one of the cDNA clones, the original full-length cDNA obtained from the bone marrow library (Clone 191), contained a large 3' untranslated region. The 3 kb untranslated fragment from this cDNA clone does not hybridize with human genomic DNA indicating that it is foreign DNA. This foreign fragment is preceded by an EcoRI site and a possible liner and may have been artificially inserted during the preparation of the library.

Sequences of the 3' segments of transcripts in peripheral blood by RNA PCR only detected short 3' untranslated regions, which varied slightly in length before the poly A tail. Similar sequences were obtained when other cDNAs from the human bone marrow library were analyzed. The larger Kell transcripts could not be amplified using the RNA PCR method because of their length, but Northern analysis indicates their presence. The occurrence of multiple transcripts with larger 3' untranslated region is not uncommon and although their function is not well understood, the 3' untranslated regions are thought to play roles in regulation of expression (Refs. 61–62).

EXAMPLES 5–7

DNA Preparation

In Examples 5–7, DNA was prepared from peripheral blood obtained from persons whose Kell phenotypes have been determined serologically. DNA was prepared either from 1 to 5 ml of whole blood collected with anticoagulants or, when red cells were removed by centrifugation at 1000×g for 10 mins, from the resulting buffy coat. In both cases, the procedure described by John et al. (Ref. 63) to prepare DNA was used. Some of the DNA samples were obtained from Canadian Hutterites and serological studies of these families indicated that they were homozygous for either K1 or K2. In these samples DNA was isolated as described by Zelinski et al. (Ref. 30).

Polymerase Chain Reaction

For Examples 5–7, the polymerase chain reaction was performed as follows: Denaturation, annealing and polymerization steps were performed in an automated thermocycler (Minicycler, MJ Research Inc., Watertown, Mass.). An initial cycle of 94° C. for 3 min., 62° C. for 1 min., and 72° C. for 30 seconds. In cycles 2 through 30 the conditions were 94° C. for 30 seconds, 62° C. for 30 seconds, and 72° C. for 30 seconds. In the last cycle the polymerization step at 72° C. was extended to 10 minutes. The final concentrations of reagents were 50 mM KCl, 10 mM Tris-HCl (pH 9.0), 3 mM $MgCl_2$, 350 nM of each primer, 200 μM of each dNTP, 0.1% Triton-X1000, 100–200 ng genomic DNA and 2.5 units of taq polymerase in a final volume of 100 μL. The "hot start" method using Ampliwax™ from Perkin Elmer (Branchburg, N.J.) was employed. The amplified PCR products were separated by electrophoresis on 0.8% agarose gels and detected by ethidium bromide staining.

Restriction Enzyme Digestion

BsmI was added directly to the final PCR reaction mixture. The PCR mixture (10 μL) was optimized by BsmI digestion by adding 2 μL of 35 mM $MgCl_2$, 1 μL of 10 mM mercaptoethanol or 10 mM DTT, 1 μL of 10X BsmI buffer, 4 μL of water, and 2 μL of 5 units/mL BsmI. The mixture were incubated for 90 min. at 65° C. The DNA in the reaction mixture was analyzed by electrophoresis in 0.8% agarose.

Other Reagents

Taq DNA polymerase and dNTPs were purchased from Promega Co. (Madison, Wis.). X-Gal was purchased from Appligene Inc. (Pleasanton, Calif.). The DNA 1 kb ladder standards, DH5αF' strain *E. coli* competent cells, and the low melting agarose were purchased from Bethesda Research Laboratories (Gaithersburg, Md.). T4 DNA ligase and BsmI were purchased from New England Biolabs (Beverly, Mass.). pT7 blue (R) plasmid vector was purchased from Novagen (Madison, Wis.). Quick Spin™ Column (G-50 Sephadex) for DNA purification was purchased from Boehringer Mannheim, Inc. (Indianapolis, Ind.).

EXAMPLE 5

Comparison of K1 and K2 DNA Sequences

Figure 6:
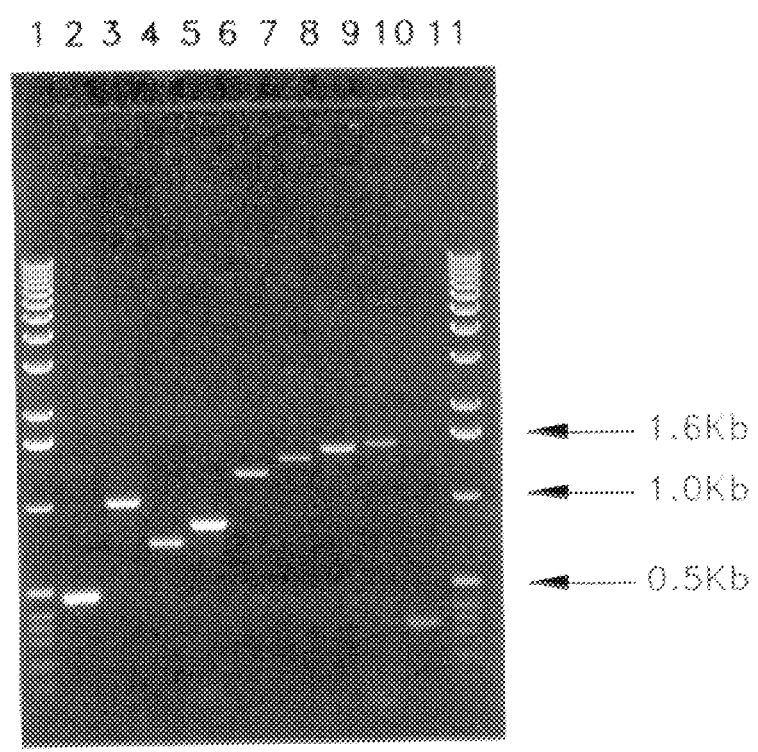
FIG. 6 shows an ethidium bromide/agarose gel illustrating a differential separation of amplified DNA corresponding to specific fragments of the Kell gene.

Nine pairs of forward and reverse primers were used to amplify the 19 KEL exons. These primer pairs were selected to cover the open reading frames of the exons. The sequences of the primers and the target exons (spanning regions) are shown in Table 1. Genomic DNA from a homozygous K1 person was used as template DNA. The PCR products were separated by electrophoresis on 0.8% agarose gels and stained with ethidium bromide. In all cases single products ranging in size from 0.48 to 1.5 kb were obtained. FIG. 6 illustrates the PCR amplification of the KEL exons. Lanes 1 and 11 in FIG. 6 are 1 kb DNA ladder standards. Lanes 2 to 10 contain PCR products of the primer pairs PCR 1, 2, 3, 4, 5, 6, 7, 8 and 9, in that order.

TABLE 1

Primers Used in PCR of KEL Exons

| PCR | Primers | SEQ ID NOS: | Target Exons | Product (kb) |
|---|---|---|---|---|
| 1 | 5'-CAG TCC TCC GAA TCA GCT CCT AGA-3' | 13 | 1*2* | 0.48 |
|   | 5'-CTC TTG GCT CCA GAG AGT TCC CAT-3' | 14 | | |
| 2 | 5'-GAA GGT GGG GAC CAA AGT GAG GAA-3' | 15 | 2*, 3, 4 | 1.0 |
|   | 5'-ACA GGG TTT GGA GCA GTC ATG GTC-3' | 16 | | |
| 3 | 5'-TTT AGT CCT CAC TCC CAT GCT TCC-3' | 4 | 5,6 | 0.74 |
|   | 5'-TAT CAC ACA GGT GTC CTC TCT TCC-3' | 5 | | |
| 4 | 5'-ATA TTC CCC ACC TCC CCA CAC CTG-3' | 17 | 7, 8, 9 | 0.8 |
|   | 5'-ATC TAC GGT GCT CAG GCT CTC CTC-3' | 18 | | |
| 5 | 5'-GGA AGC ATG GGA GTG AGG ACT AAA-3' | 19 | 10 | 1.2 |
|   | 5'-TGG CAT CCA TGG TAC CTC ATG GAA-3' | 20 | | |
| 6 | 5'-GAG GCT TTT GAA ACC CCA GGA TGA-3' | 21 | 11 | 1.3 |
|   | 5'-TTC CCC AGC CAC CTG CCA TCT CAT-3' | 22 | | |
| 7 | 5'-CCC TTT TCC AAG GGT CAG AAG CTG-3' | 23 | 12, 13, 14, 15 | 1.4 |
|   | 5'-GGG CTT ATT TGA CCC CCA GAA TCT-3' | 24 | | |
| 8 | 5'-CCT AAT CCC TGG ATG CCT GCC TGT-3' | 25 | 14*, 15, 16, 17, 18 | 1.5 |
|   | 5'-CAG TGA GGA CAT CTG CAG AAG AGG-3' | 26 | | |
| 9 | 5'-TCC TGT GGA CCC TCC CCC TTC AAT-3' | 27 | 19* | 0.33 |
|   | 5'-GGG CGG AAG CCA AGT GCC AGC TTT T-3' | 28 | | |

The first primer is the forward sequence and the second is the antisense primer. The 2G bases at the 5' end of antisense primer of PCR are not in the gene and were added to create an SmaI site for another purpose. Some PCR products did not cover the entire exons and those exons are marked with asterisks. The PCR products of exons 1 (PCR1) and 19 (PCR 9) contain the entire translated regions. Exon 2 was spanned by overlapping PCR products (PCR 1 & 2) and exon 14 was covered by PCR 7.

EXAMPLE 6

The PCR products obtained in Example 1 were sequenced using the following protocol: The PCR products, separated by electrophoresis on low 2.8% melting agarose, were eluted, ligated to pT7 Blue(R) plasmid vector and transformed in DH5αF' strain of *E. coli*. Plasmid DNA was prepared on a small scale by the alkali lysis method and purified with a Quick Spin™ (Sephadex G50) column. Standard molecular biology procedures were employed, such as are described in detail in Sambrook et al. (Ref. 42). DNA sequencing was performed by an automated system (Applied Biosystems, Model 373A, Version 1.2.0).

The sequenced products were compared to the previously described sequence of K2 cDNA (Ref. 25). It was unexpectedly found that the sequence of K1 DNA encodes an amino acid sequence identical to that of K2 DNA, except for a single base change. This difference between K1 and K2 occurs as a shift from C to T at nucleotide 701 in exon 6.

The PCR product PCR3 (Table 1), which spans exons 5 and 6, had a single base difference when compared to K2 DNA. The base sequences of a portion of exon 6, and the amino acids which they encode, are shown in FIG. 7. The sequence of K2 DNA is on the top and K1 DNA on the bottom. In the PCR3 product, which was 740 bp in length, there was a single cytosine (C) to thymine (T) substitution, corresponding to position 701 of the Kell cDNA. The C to T substitution is marked in bold letters and is highlighted with an arrow. This change predicts a threonine to methionine change at a consensus N-glycosylation site (Asn.X.Thr). An N-linked glycosylation motif in K2, and the disrupted motif in K1, are underlined. Since this single base change was the only difference between K1 and K2 encoding a change in an amino acid, this observation suggested that the threonine to methionine change (Thr→Met) at position 193 would prevent N-glycosylation at asparagine 191 in proteins expressing K1, thus identifying the K1/K2 polymorphism.

EXAMPLE 7
Confirmation of K1/K2 Polymorphism by BsmI Analysis

The C to T substitution at nucleotide position 701 (nt 701) in exon 6 creates a new sequence including the sequence 5'-GAATGCT-3', which is known to define a restriction enzyme site specific for BsmI. As a result, treatment of the 740 bp PCR product which spans exons 5 and 6 (PCR3) with BsmI was hypothesized to provide a means by which to differentiate K1/K2 genotypes. In a PCR method employing digestion with BsmI, the K1/K1 genotype should yield 2 fragments, of 540 and 200 bp; the K2/K2 genotype should yield the uncut 740 bp PCR product and K1/K2 heterozygotes should yield 3 fragments of 740, 540 and 200 bp. To confirm that this base change does in fact identify the K1 genotype, this region was analyzed in 42 different persons of known K1/K2 phenotype.

The PCR3 primer pair (Table 1) was used to generate PCR products (740 bp) by PCR amplification of DNA obtained from various Kell phenotypes. After amplification, the samples were treated with BsmI and separated by electrophoresis on 0.8% agarose gels.

Figure 8:
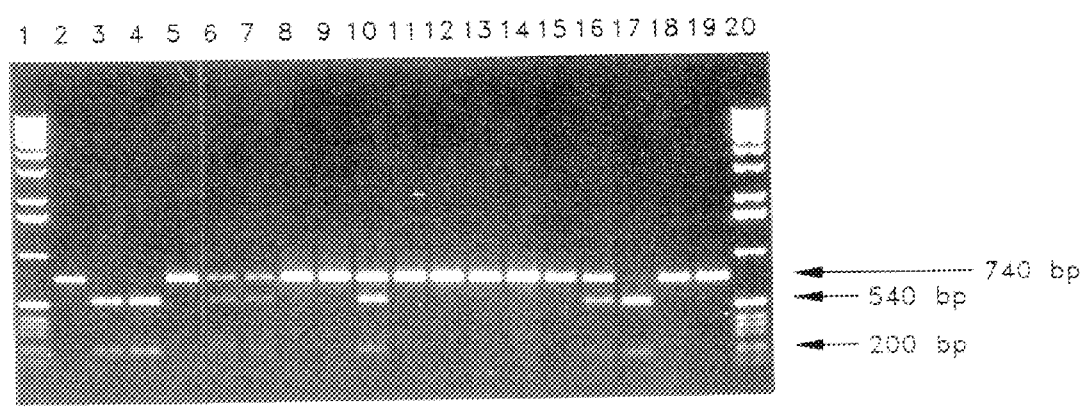
FIG. 8 shows an ethidium bromide/agarose gel illustrating a differential separation of amplified DNA corresponding to K1 DNA and K2 DNA according to the method of the invention.

FIG. 8 illustrates the results obtained in the above-described experiment. The gel lanes are defined as follows:

| Lane | Phenotype |
|---|---|
| 1 | DNA Standard |
| 2 | Untreated PCR3 |
| 3 | K:1, −2 |
| 4 | K:1, −2 |
| 5 | K:−1, 2 |
| 6 | K:1, 2 |

-continued

| Lane | Phenotype |
|---|---|
| 7 | K:1, 2 |
| 8 | K:−1, 2 |
| 9 | $K_o$ |
| 10 | K:1, 2 |
| 11 | K:−1, 2, 3, −4 |
| 12 | K:−1, 2, 6, −7 |
| 13 | McLeod |
| 14 | K:−1, 2, 10 |
| 15 | K:−1, 2, 14, 24 |
| 16 | K:1, 2 |
| 17 | K:1, −2 |
| 18 | K:−1, 2 |
| 19 | K:−1, 2 |
| 20 | DNA Standard |

Lanes 1 and 20 contain 1 kb ladder DNA standards. Lane 2 is untreated PCR3 from K1 homozygotes. Lanes 3 to 19 are treated with BsmI. All K2 homozygote (K:−1,2) samples gave uncut 740 bp products. K1 homozygotes (K:1,−2) yielded only 540 and 200 bp fragments. K1/K2 heterozygotes (K:1,2) had 3 bands, the uncut 740 and the smaller 540 and 200 bp products.

Of the 42 DNA samples tested, 12 were either K1 or K2 homozygotes, 6 were K1/K2 heterozygotes and 24 were K:−1,2 phenotypes, but contained low prevalence or rare Kell phenotypes. These included K3, K6, K10, $K_o$, K14/K24 heterozygote, and a McLeod phenotype. In 40 of the 42 cases the BsmI genotyping agreed with the Kell phenotypes which were determined by serological analysis of red cells. In two cases, genotyping identified one of the samples as K:−1,2 homozygote and the other as a K:1,2 heterozygote. These two samples were, however, serologically identified as having "weak" K1 phenotypes.

None of the other low prevalence or rare Kell phenotypes listed above had the C to T base substitution in exon 6, indicating that this change is specific for the K1/K2 polymorphism.

EXAMPLE 8

In a method of differentially determining K1/K2 genotype, the polymerase chain reaction was employed to test samples of genomic DNA using a unique primer mixture. The primer mixture included the following primers:

| MK1R | ATA CTG ACT CAT CAG AAG TTT CAG CA | (SEQ ID NO:1) |
| MK2F | TGG ACT TCC TTA AAC TTT AAC TGA AC | (SEQ ID NO:3) |
| EI5F | TTT AGT CCT CAC TCC CAT GCT TCC | (SEQ ID NO:4) |
| EI6R | TAT CAC ACA GGT GTC CTC TCT TCC | (SEQ ID NO:5) |

The MK1R primer is specific for K1 DNA, producing a PCR product 540 bp in length. The MK2F primer is specific for K2 DNA, and produces a PCR product 240 bp in length. The other primers EI5F and EI6R are K1/K2 specific, producing PCR products 740 bp in length, and are used as an internal control.

The primer mix included the primers in the following concentrations: 20 ng/μL MK1R; 20 ng/μL MK2F; 30 ng/μL EI5F; and 30 ng/μL EI6R. EI5F and EI6R primers are used in the PCR for two reactions, while the MK1 R and MK2F primers are each used for only one reaction. The concentrations of the primers were adjusted to ensure sufficient quantities of the EI5F and EI6R primers for the duration of the reaction.

Blood samples were obtained from human volunteers. DNA was isolated from leukocytes present in the buffy coat of blood samples using the method described elsewhere herein.

Reaction tubes were set up including one Ampliwax™ and 25 µL of a first reagent cocktail including: 2.5 µL 10× buffer (Promega Co., Madison, Wis.); 4 µL dNTP; 3 µL 25 mM $MgCl_2$; 7 µL primer mix; and 8.5 1µL $H_2O$, to give a preliminary reaction mixture volume of 25 µL. These preliminary mixtures were incubated a 80° C. for 5 min. and cooled to room temperature for 5 min. before proceeding. To each of the tubes were added 23 µL of a second reagent cocktail including: 2.5 µL 10× buffer; 3 µL 25 mM $MgCl_2$; 17 µL $H_2O$; and 0.5 µL taq DNA polymerase (Promega Co., 5 units/µL) and 100 ng of isolated genomic DNA in 2 µL $H_2O$.

The PCR reaction was performed using the following cycling program. The initial cycle comprised 94° C. for 3 minutes, 62° C. for 1 minute, and 72° C. for 30 seconds. Cycles 2–30 each included 94° C. for 30 seconds, 62° C. for 30 seconds, and 72° C. for 30 seconds. In the last cycle, the polymerization step was 72° C. was extended to 10 minutes.

Following completion of the PCR, the amplified products were resolved using ethidium bromide/agarose gel electrophoresis as described in the art.

Figure 9:
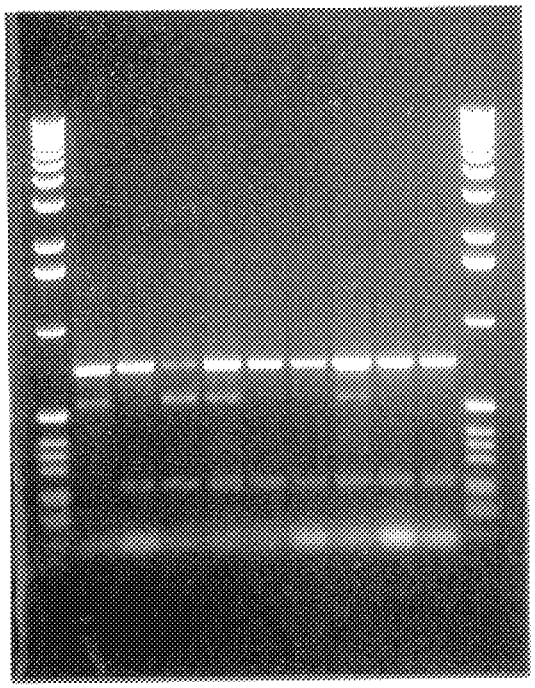
FIG. 9 shows an ethidium bromide/agarose gel electrophoresis resolution of PCR products obtained according to the method of the invention.

The results are of this procedure are shown in FIG. 9. Lanes 1 and 11 are identical control samples including mixed DNA fragments of known size. Lanes 2–4 represent internal control samples from subjects in whom the K1/K2 genotype was already known. Control Lane 2 shows the presence of 540 bp and 740 bp fragments, indicating that the subject is homozygous K1 (K:1,–2). Control Lane 3 shows the presence of 200 bp and 740 bp fragments, indicating that the subject is homozygous K2 (K:–1,2). Control Lane 4 shows the presence of each of the K1 /K2 fragments, i.e., 200 bp, 540 bp, and 740 bp, indicating that the subject is heterozygous (K:1,2).

Lanes 5–7 in FIG. 9 represent samples from a family of test subjects: Lanes 5 and 6 represent parents and Lane 7 represents the fetus. A comparison of the test bands with the control bands reveals that the parent represented in Lane 5 is heterozygous (K:1,2) and that the parent represented in Lane 6 is homozygous K2 (K:–1,2). The fetus is clearly homozygous K2 (K:–1,2).

Lanes 8–10 in FIG. 9 represent samples from another family of test subjects. The first parent, represented in Lane 8, is heterozygous (K:1,2), while the second parent, represented in Lane 9, is homozygous K2 (K:–1,2). The fetus, represented in Lane 10, is identifiable as being homozygous K2 (K:–1,2).

The experimental data provided in Examples 7 and 8 clearly demonstrate the diagnostic efficacy of the method of the invention. The examples show that individuals of each of the three K1/K2 genotypes can be distinguished positively by virtue of the differences between K1 DNA and K2 DNA. More particularly, the newly identified locus of K1/K2 polymorphism can be exploited by means of amplification of Kell DNA using K1- and K2-specific nucleic acid probes, as well as by differential digestion of K1/K2 DNA with a restriction enzyme.

EXAMPLE 9

The molecular basis for the K6/K7 polymorphism has now unexpectedly been found, showing that it is due to a point mutation in exon 17 leading to proline (K6) being encoded instead of leucine (K7) at amino acid position 597 of the Kell protein. This amino acid substitution is in close proximity to the zinc-binding putative enzyme active site of Kell protein.

DNA Preparation.

Leukocyte DNA was prepared from peripheral blood of eight unrelated individuals with K6 phenotype, as described in Examples 5–7, based on a procedure described by John et al. (Ref. 63).

Polymerase Chain Reaction (PCR).

The forward and reverse primers used to copy and amplify the 19 exons of the KEL gene were, for the most part, the same as those previously described elsewhere herein. In a few instances, other primers were designed to produce smaller PCR products to facilitate sequencing. The forward and reverse primers used to amplify an 807 bp segment from exons 17 and 18 are 5'-CTCACCTAGGCAGCACCAACCCTA-3' (SEQ ID NO:64) and 5'-CAGTGAGGACATCTGCAGAAGAGG-3' (SEQ ID NO:26), respectively. The PCR conditions used were the same as previously described in Examples 5–7 above, except that the number of cycles was increased to 35.

DNA Sequencing.

The PCR products were separated by gel electrophoresis on 0.8% low melting agarose gels. After elution the DNA was either directly sequenced or subcloned into pT7Blue (R)T plasmid vector (Novagen, Madison, Wis.), and transformed in DH5αF' strain of E. coli (Gibco BRL Life Technologies, Gaithersburg, Md.). If subcloned, the plasmid DNA was prepared in a small scale by the alkali lysis method and purified with a Quick Spin™ (Sephadex™ G50) column. Standard molecular biology procedures were employed. DNA sequencing was performed by an automated system (Model 373A, Version 1-2.0, Applied Biosystems, Foster City, Calif.).

Restriction Enzyme Digestion of PCR Product.

A short 111 bp sequence of exon 17, predicted to contain the point mutation for the K6 genotype, was copied and amplified by PCR. Only a short segment of exon 17 was copied because exon 17 contains other neighboring MnlI cleavage sites. The following oligonucleotide primers were used for the PCR reaction, 5'-CTCACCTAGGCAGCACCAACCCTA-3' (SEQ ID NO:64) (forward primer, same as described above in this Example, and 5'-TTACCTGGAGGGCATGGTTGTCACT-3' (SEQ ID NO:65) (reverse primer). The PCR product (10 µL of final reaction mixture) was treated with 10 Units of MnlI (New England Biolabs, Beverly, Mass.) and incubated at 37° C. for 90 minutes. The final reaction volumes was 20 µL. The DNA was then separated by electrophoresis on 0.7% agarose gels, supplemented with 1.65% GelTwin™ brand surfactant (J. T. Baker, Philipsburg, N.J.).

Comparison of K6 and K7 DNA sequences.

The base sequences of the PCR products corresponding to the 19 exons of K:6,–7 DNA were compared to a "wild-type" DNA (K:–6,7), which expresses the high incidence Kell phenotypes including K7 (Ref. 43). Two discrete base substitutions were noted, both occurring in exon 17. The changes are shown graphically in FIG. 10. At nt 1910, a T to C change was observed which results in a proline being encoded instead of leucine at amino acid position 597. Another base substitution, A to G, was observed at nt 2019, but this change does not cause the encoding of a different amino acid.

Confirmation of K6/K7 Polymorphism by MnlI Digestion.

The T to C substitution at nt 1910 eliminates a recognition site for the restriction endonuclease MnlI. Thus, wild-type K7 DNA is cleaved at this point when exposed to MnlI, while the low frequency K6 DNA is not affected. This distinct feature may be used to analyze for this point mutation and to determine whether this substitution identifies the K6 genotype. A 111 bp sequence, which spans this region of exon 17, was obtained by PCR of genomic DNA from eight unrelated K:6,–7 and K:–6,7 persons, and treated with MnlI. The K7 (wild-type) DNA contains the MnlI site and upon treatment with MnlI yields a 91 bp and 20 bp products. On the other hand, the K6 PCR product is not cleaved by MnlI, and the 111 bp product remains uncut. Thus, a heterozygote yields both the uncut PCR product and the two smaller bands.

Figure 11:
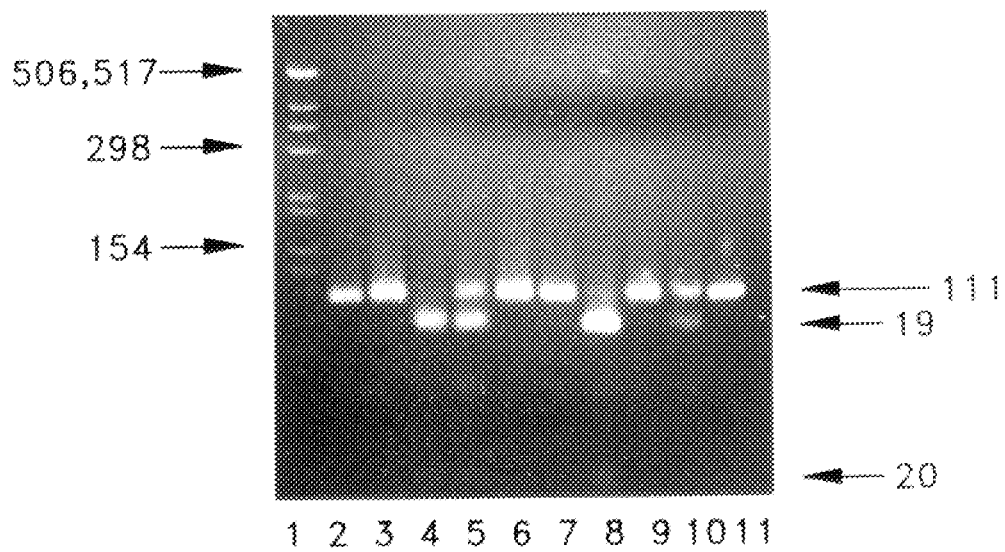
FIG. 11 shows an ethidium bromide/agarose gel electrophoresis resolution of K6/K7 PCR products obtained according to the method of the invention.

The results are shown in FIG. 11. PCR products from seven unrelated K6 phenotype persons all showed 111 bp bands. Four examples are shown (Lanes 3, 6, 7, 9). PCR products from all K7 phenotype persons showed a smaller 91 bp product (Lanes 4 and 8), but the 20 bp product, because of its small size, was difficult to detect by ethidium bromide staining. The K:6,7 heterozygotes (Lanes 5 and 10) showed both the uncut 111 bp band and the smaller 91 bp band.

Chimpanzee red cells carry the K6 ($Js^a$) antigen (Ref. 27). A single DNA sample from a chimpanzee was analyzed and it also yielded the 111 bp uncut PCR product, a pattern which is consistent with a K:6,–7 genotype. This result is shown as Lane 11 in the gel shown in FIG. 11.

EXAMPLE 10

The K6/K7 polymorphism was explored further and a second restriction enzyme cleavage site was identified in association with the point mutation at nt 2019. While this is a silent mutation, it may be exploited according to the invention since it is consistently associated with the expressed mutation at nt 1910.

DNA was prepared from peripheral blood of the seven individuals identified in Example 9, as described therein. The PCR and DNA sequencing were performed as described in Example 9. The 807 bp PCR product was digested with DdeI. Ten microliters (10 μL) of the PCR product was incubated with 10–20 units of DdeI (New England Biolabs, Beverly, Mass.) at 37° C. for 90 minutes, and the enzyme-digested mixture was separated on a 0.7% agarose gels supplemented with 1.65% GelTwin™, as described in Example 9.

Figure 12:
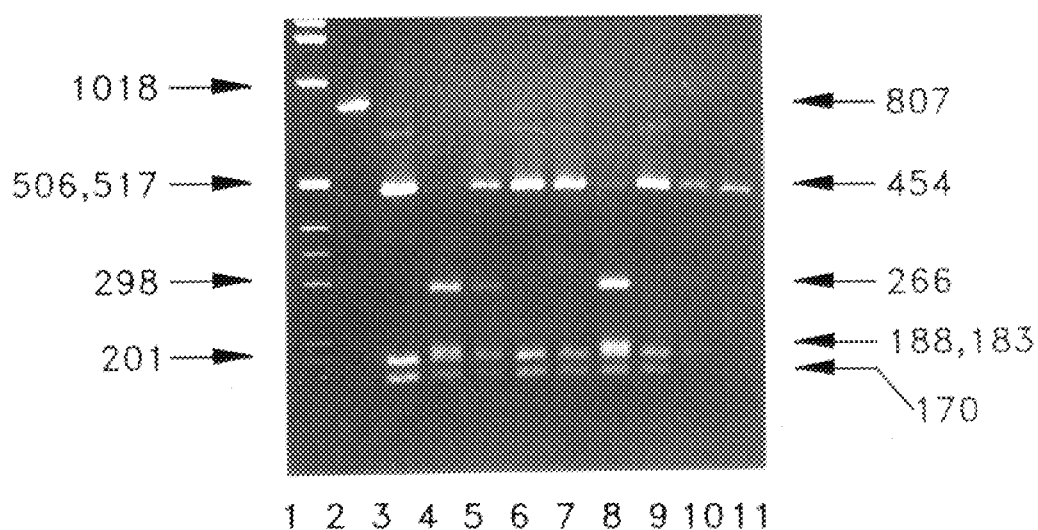
FIG. 12 shows an ethidium bromide/agarose gel electrophoresis resolution of K6/K7 PCR products obtained according to the method of the invention.

The PCR product was found to have several DdeI sites, and multiple bands were obtained upon digestion. DNA from four K6 phenotype individuals yielded three prominent bands of 454, 183, and 170 bp (FIG. 12, Lanes 3, 6, 7, and 9). By contrast, the K& phenotypes yielded four bands (266,188,183, and 170 bp), because the 454 bp band was further digested to 266 and 188 bp products (Lanes 4 and 8). the 188 and 183 bp products are not well separated, and sometimes migrate together. Two heterozygotes (Lanes 5 and 10) could be distinguished from the K6 and K7 homozygotes, because they yielded five bands (454, 266, 188, 183, and 170 bp).

One sample of chimpanzee DNA was also digested using DdeI. As noted above in Example 9, chimpanzee red cells carry type K:6,–7. As shown in FIG. 12, the 454 bp product was uncut by DdeI (Lane 11), again consistent with a K:6,–7 genotype.

A comparison of the base sequence of the coding region of the KEL gene of K6 and K7 DNA showed only 2 base differences, both occurring in exon 17. See FIG. 10. Only one of these base substitutions encoded a different amino acid. A T to C change at nt 1910 changed a leucine to a proline at amino acid residue 597. The other base substitution at nt 2019 is a silent mutation which retains leucine at that position. Both of the base substitutions at nt 1910 and nt 2019 are common to K:6,–7 genotypes, since analysis of the seven unrelated individuals described in Examples 9 and 10 showed these base changes. As expected, K:6,7 heterozygotes possessed both the wild-type and the K:6,–7 sequences.

The pentameric consensus sequence, HEXXH (SEQ ID NO:60), which Kell protein shares with a family of zinc endopeptidases occurs at amino acid residues 581 to 585. Thus, this putative active site is in close proximity to residue 597 which has the leucine (K7) to proline (K6) change. We cannot predict whether this amino acid change influences the putative enzymatic activity of Kell, but its proximity cannot be ignored. It is also of interest that the leucine to proline change occurs at a residue which is located between two cysteine residues (see FIG. 10) yielding a Cys.Pro.Ala.Cys sequence in K6, and a Cys.Leu.Ala.Cys sequence in K7. Because of their distinctive molecular structure, proline residues can induce local structural changes in proteins, and can change the geometry of helices. In this case, because it is situated between two cysteine residues, proline could cause rearrangements of disulfide bonds, thus markedly changing the secondary and tertiary structure of the protein and exposing new epitopes. A computer assisted Chou-Fasman analysis of the secondary structure of Kell protein indicates that substituting proline for leucine at residue 597 would, in fact, alter the turns predicted for that region.

It should be noted that Kell has 16 cysteine residues, with 15 of these residues occurring in the extracellular domain, and one occurring in the membrane-spanning region. This indicates extensive folding of the protein, which is in agreement with early biochemical studies showing inactivation of Kell antigen by reducing reagents. Of all the Kell antigens, K6 and K7 are the ones which are inactivated with the lowest concentrations (1–2 mM) of dithiothreitol (DTT). Other Kell antigens such as K1, K2, K3 and K21 require much higher concentrations (100–200 mM) of DTT for inactivation.

An immunological procedure, termed MAIEA, has been used to map the spatial relationships between Kell epitopes. This method has predicted that K6/K7 is close to the K1/K2 epitope in the native Kell protein. The point mutation which distinguishes the K1/K2 polymorphism occurs at amino acid residue 193, while that for K6/K7 is linearly distant, occurring at amino acid 597. This apparent discrepancy again points to the folded nature of Kell protein and that the epitopes can be far removed from the points of mutation.

The experimental data provided in Examples 9 and 10 again show the diagnostic efficacy of the method of the invention. Specifically, individuals of having various K6/K7 genotypes can be distinguished positively on the basis of differences between K6 DNA and K7 DNA. More particularly, the newly identified locus of K6/K7 polymorphism can be exploited by means of amplification of Kell DNA using K6- and K7-specific nucleic acid probes, as well as by differential digestion of K6/K7 DNA with a restriction enzyme.

EXAMPLE 11

Further studies revealed that a single nucleotide substitution at nt 1601 in exon 13 of the KEL gene is associated with K10 genotype. The molecular basis of K10 is shown in FIG. 13, which provides the nucleotide and amino acid sequences of wild-type Kell DNA in the K10 polymorphism locus, as well as the point mutation (A 1601 T) which causes a change in amino acid sequence (Glu 494 Val). The point mutation at nt 1601 results in the K10 phenotype.

RFLP analysis was performed in general accordance with the methods described elsewhere herein. It was found that the nucleotide substitution creates a new cleavage site for the restriction enzyme AccI, permitting differential detection of amplification products from K10 and wild-type DNA and consequent differential determination of K10 genotype.

EXAMPLE 12

Analysis of the K3/K4/K21 polymorphism locus was performed to establish whether RFLP methods could be used to determine K3/K4/K21 genotype. Studies revealed unexpectedly that two discrete nucleotide substitutions in a single codon are associated with the polymorphism of the K3/K4/K21 locus. The molecular basis of K4 is shown in FIG. 14, which provides the nucleotide and amino acid sequences of K4 DNA, as well as the point mutations which causes changes in amino acid sequence. The point mutation at nt 961 (C→T) cause a change in amino acid sequence (Arg 281 Trp), resulting in the K3 phenotype. The point mutation at nt 962 (G→A) cause a change in amino acid sequence (Arg 281 Gln), resulting in the K21 phenotype.

RFLP analysis was performed in general accordance with the methods described elsewhere herein. It was found that the C 961 T nucleotide substitution creates a new cleavage site for the restriction enzyme NlaIII, permitting differential detection of amplification products from K3 and wild-type K4 DNA and consequent differential determination of K3/K4 genotype. It was also found that the G 962 A nucleotide substitution creates a new cleavage site for the restriction enzyme PvuII, permitting differential detection of amplification products from K21 and wild-type K4 DNA and consequent differential determination of K21/K4 genotype. Together, the discovery of these restriction sites now enables a method for directly determining K3/K4/K21 genotype.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

1. Giblett ER, "A critique of the theoretical hazard of inter- vs. intra-racial transfusion" *Transfusion* 1:233 (1961).
2. Mayne K. M., Bowell P. J., and Pratt G. A. , "The significance of anti-Kell sensitization in pregnancy" *Clin Lab Haematol* 12:379–385 (1990).
3. Duguid J. K. M., and Bromilow I. M., "Haemolytic disease of the newborn due to anti-K" *Vox Sang* 58:69 (1990). 4. Moncharmont P, Juron-Dupraz F, Doillon M, Vignal M, and Debeaux V, "A case of hemolytic disease of the newborn infant due to anti-K (Cellano)" *Acta Haematol* 85:45 (1991).
5. Constantine G, Fitzgibbon N, and Weave J. B., "Anti-Kell in pregnancy" *Brit J Obs Gyn* 98:943 (1991).
6. Leggat H. M., Gibson J. M., Barron S. L., and Reid M. M., "Anti-Kell in pregnancy" *Brit J Obs Gyn* 98:162 (1991).
7. Bowman J. M., Pollock J. M., Manning F. A., Harman C. K., and Menticoglou S, "Maternal Kell blood group alloimmunization" *Obstetrics and Gynecology* 79:239 (1992).
8. Lee S, Zambas E, Marsh W. L., and Redman C. M., "The human Kell blood group gene maps to chromosome 7q33 and its expression is restricted to erythroid cells" *Blood* 81:2804 (1993).
9. Zelinski T, Coghlan G, Myal Y, Shiu RPC, Phillips S, White L, and Lewis M, "Genetic linkage between the Kell blood group system and prolactin-inducible protein loci: Provisional assignment of KEL to chromosome 7" *Ann Hum Genet* 55:137 (1991).
10. Purohit K. R., Weber J. L., Ward L. J., and Keats B. J. B., "The Kell blood group locus is closed to the cystic fibrosis locus on chromosome 7" *Hum Genet* 89:457 (1992).
11. Murphy M. T., Morrison N, Miles J. S., Fraser R. H., Spurr N. K., and Boyd E, "Regional chromosomal assignment of the Kell blood group locus (KEL) to chromosome 7q35–q35 by fluorescence in situ hybridization: Evidence for the polypeptide nature of antigenic variations" *Hum Genet* 91:585 (1993).
12. Giblett E. R., and Chase J, "$Js^a$ a 'new' red cell antigen found in negroes: evidence for an eleventh blood group system" *Brit J Haematol* 5:319–26 (1959).
13. Furuhjelm U, Nevanlinna H. R., Nurkka R, Gavin J, Tippett P, Gooch A, and Sanger R, "The blood group antigen $Ul^a$ (Karhula)" *Vox Sang* 15:118–24 (1968).
14. Marsh W. L., "Blood groups of human red cells in clinical practice of blood transfusion" (Petz, L. D. and Swisher S. N., eds) pp. 79–130, Churchill-Livingstone, New York (1981).
15. Marsh W. L. and Redman C. M., "Recent developments in the Kell blood group system" *Trans Med Rev* 1:4 (1987).
16. Marsh W. L. and Redman C. M., "The Kell blood group system: a review" *Transfusion* 30:151 (1990).
17. Redman C. M. and Marsh W. L., "The Kell antigens and McLeod red cells" in *Protein Blood Group Antigens of the Human Red Cell:structure, Function and Clinical Significance*. (Agre P. C. and Cartron J. P., eds.) pp 53–69, Johns Hopkins University Press, Baltimore, Md. (1992).
18. Redman C. M. and Marsh W. L., "The Kell blood group system and the McLeod phenotypes" *Seminars in Hematology* 40:309 (1993).
19. Redman C. M., Marsh W. L., Mueller K. A., Avellino G. P., and Johnson C. L., "Isolation of Kell-active protein from the red cell membrane" *Transfusion* 24:176 (1984).
20. Wallas C, Simon R, Sharpe M. A., and Byler C, "Isolation of Kell-reactive protein from red cell membranes" *Transfusion* 26:173 (1986).
21. Redman C. M., Avellino G, Pfeffer S. R., Mukherjee T. K., Nichols M, Rubinstein P, and Marsh W. L., "Kell blood group antigens are part of a 93,000 Dalton red cell membrane protein" *J Biol Chem* 261:9521 (1986).
22. Jaber A, Blanchard D, Goossens D, Bloy C, Lambin P, Rouger P, Salmon C, and Cartron JP, "Characterization of blood group Kell (K1 ) antigen with a human monoclonal antibody" *Blood* 73:1597 (1989).
23. Jaber A, Loirot M.J., Willem C, Bloy C, Cartron J. P., and Blanchard D, "Characterization of murine monoclonal antibodies directed against the Kell blood group glycoprotein" *Brit J Haematbl* 79:311 (1991).
24. Parson S. F., Gardner B, and Anstee D. J., "Monoclonal antibodies against Kell glycoprotein: Serology, immunochemistry and quantification of antigen sites" *Transfusion Medicine* 3:137 (1993).
25. Lee S, Zambas E, Marsh W. L., and Redman C. M., "Molecular cloning and primary structure of Kell blood group protein" *Proc Natl Acad Sci (USA)* 88:6353 (1991).
26. Petty A. C., Daniels G. L., and Tippett P, "Application of the MAIEA assay to the Kell blood group system" *Vox Sang* 66:216 (1994).
27. Redman C. M., Lee S, Ten Bokkel Huinink D, Rabin, B.I., Johnson C. L., Oyen R, and Marsh W. L., "Com- 27. parison of human and chimpanzee Kell blood group system" *Transfusion* 239:486–490 (1989).
28. Branch D, Muensch H, Sy Siok Hian A, and Petz D, "Disulfide bonds are a requirement of Kell and Cartwright (Yt$^a$) blood group antigen integrity" Br J Haematol 54:573–578 (1993).
29. Jongeneel C. X., Bouvier J, and Bairoch A, "A unique signature identifies a family of zinc-dependent metallopeptidases" *FEBS Letters* 242:211 (1989).
30. Zelinski T, "The use of DNA restriction fragment length polymorphisms in conjunction with blood group serology" *Transfusion* 31:762–770 (1991).
31. Bause E, "Structural requirements of N-glycosylation proteins" *Biochem J* 209:331–336 (1983).
32. Telen M. J., Le Van Kim C, Guizzo M. L., Cartron J. P., and Colin Y, "Erythrocyte Webb-type glycophorin C variant lacks N-glycosylation due to an asparagine to serine substitution" *Am J Hematol* 37:51–52 (1991).
33. Chang S, Reid M, Conboy J, Kan Y, and Mohandas N, "Molecular characterization of erythrocyte glycophorin C variants" *Blood* 77:644–648 (1991).
34. Innis M. A., Gelfand D. H., Sninsky J. J., and White T. J., *PCR Protocols: A Guide to Methods and Applications*, Academic Press, Inc., San Diego (1990).
35. Landegren U, et al., *Science* 241:1077 (1988).
36. Barany F, *PCR Methods and Applications* 1:5 (1991).
37. Narang et al., *Meth Enzymol* 68:90 (1979.
38. Brown et al., *Meth Enzymol* 68:109 (1979).
39. Beaucage et al., *Tetrahedron Lett* 22:1859 (1981).
40. Glick B. R. and Pasternak J, J., *Molecular Biotechnology: Principles and Applications of Recombinant DNA*, American Society for Microbiology Press, Washington, D.C. (1994).
41. Walker R. H. et al., eds., *Technical Manual*, 10th ed., American Association of Blood Banks, Arlington, Va. (1990).
42. Sambrook J, Fritsch E. F., and Maniatis T, *Molecular Cloning: A Laboratory Manual*, 2d. ed., Cold Spring Harbor Laboratory, NY (1989).
43. Lee S, Zambas E, Green E. D., and Redman C, "Organization of the gene encoding the human Kell blood group protein" *Blood* 85:912–16 (1995).
44. Gerard N. P., Bao L, Yiao-Ping H, Eddy R. L., Shows T. B., and Gerard C, "Characterization of the human C5a receptor gene" *Biochemistry* 32:1243 (1993).
45. Letarte M, Vera R, Tran J. B. L., Addis J. B. L., Ouizuka R. J., Quackenbush E. J., Jongeneel C. Y., and McInnes R. R., "Common acute lymphocytic leukemia antigen is identical to neutral endopeptidase" *J Exp Med* 168:1247 (1988).
46. Shipp M. A., Vijayaraghavan J, Schmidtt E. V., Masteller E. L., D'Adamio L, Heish L. B., and Reinherz E. L., "Common acute lymphoblastic antigen (CALLA) is active neutral endopeptidase 24.11 (enkephalinase): Direct evidence by cDNA transfection analysis" *Proc Natl Acad Sci USA* 86:297 (1989).
47. D'Adamio L, Shipp M. A., Masteller E. L., and Reinherz E. L., "Organization of the gene encoding common acute lymphoblastic leukemia antigen (neutral endopeptidases 24.11):Multiple mini exons and separate 5' untranslated region" *Proc Natl Acad Sci USA* 86:7103 (1989).
48. Bucher P, and Trifonov E. N., "Compilation and analysis of eukaryotic POL II promoter sequences" *Nucleic Acids Res.* 14:10009 (1986).
49. Evans T, Reitman M, and Felsenfeld G, "An erythrocyte-specific DNA-binding factor recognizes a regulatory sequence common to all chicken globin genes" *Proc Natl Acad Sci, USA* 85:5976 (1988).
50. Plum M, Frampton J, Wainwright H, Walker M, Macleod K, Goodwin G, and Harrisson P, "GATAAG: A cis-control region binding an erythroid specific nuclear factor with a role in globin and non-globin gene expression" *Nucleic Acids Res.* 17:73 (1989).
51. Philipsen S, Talbot D, Fraser P, and Grosvelt F, "The β-globin dominant control region: Hypersensitive site 2" *EMBO J.* 9:2159 (1990).
52. Beaupain D, Elouet J. F., and Romeo P. H., "Initiation of transcription of erythroid promoter of the porphobilinogen deaminase gene is regulated by a cis-acting sequence around the cap site" *Nucleic Acids Res.* 18:6509 (1990).
53. Maouche L, Tournamille C, Hattab C, Boffa G, Cartron J. P., and Chretian S, "Cloning of the gene encoding the human erythropoietin receptor" *Blood* 78:2557 (1991).
54. Rahuel C, Vinit M-H, Lemarchandel V, Cartron J. P., and Romeo P-H, "Erythroid specific activity of the glycophorin B promoter requires GATA-1 mediated displacement of a repressor" *EMBO J.* 11:4095 (1992).
55. Cherif-Zahar B, LeVan Kim C, Rouillac C, Raynal V, Cartron J. P., and Colin Y. P., "Organization of the gene (RHCE) encoding the human blood group RhCcEe antigens and characterization of the promoter region" *Genomics* 19:68 (1994).
56. Crotta S, Nicolis S, Ronchi A, ottolenghy S, Ruzzi L, Shimada Y, Migliaccio A. R., and Migliaccio G, "Progressive inactivation of the expression of the erythroid transcription factor in GM- and G-CSF-dependent cell lines" *Nucleic Acid Res.* 18:6864 (1990).
57. Orkin S. H., Tsai S. F., Zan L. I., Martin D, and Whitelaw E, "The erythroid-specific transcription factor GATA-1: Structure and expression" in *Regulation of Hemoglobin Switching*, (Stamatoyannopoulus G, Nienhuis A. W., eds) Alan R Liss, New York. pp 310 (1992).
58. Crossley M, and Orkin S. H., "Regulation of the β globin locus" *Current Opinion in Genetics and Development* 3:232 (1993).
59. Goosens M and Kan Y. W., "DNA analysis in the diagnosis of hemoglobin disorders" *Methods Enzymol* 76:805 (1981).
60. Wahle E and Keller W, "The biochemistry of 3' end cleavage and polyadenylation of messenger RNA precursors" *Ann Rev Biochem* 61:419 (1992).
61. Rastinejad F and Blau H. M., "Genetic complementation reveals a novel regulatory role for 3' untranslated regions in growth and differentiation" *Cell* 72:903 (1993).
62. Jackson R.J., "Cytoplasmic regulation of mRNA function:The importance of the 3' untranslated region" *Cell* 74:9 (1993).
63. John, S. W. M., Weitzner G, Rozen R, and Scriver C. R., "A rapid procedure for extracting genomic DNA from leukocytes" *Nucleic Acids Res* 19:408 (1991).

What is claimed is:

1. A diagnostic method for determining Kell genotype of a subject, comprising:
   (a) obtaining a nucleic acid sample from a subject;
   (b) generating a nucleic acid fragment from said sample, the detection of which permits the differentiation of alleles of a Kell polymorphism;
   (c) detecting said nucleic acid fragment; and
   (d) determining the genotype of said subject with respect to said Kell polymorphism based on said detecting.

2. The diagnostic method of claim 1, comprising generating a nucleic acid fragment which is diagnostic of K1 and/or K2 genotype.

3. The diagnostic method of claim 1, comprising generating a nucleic acid fragment which is diagnostic of K6 and/or K7 genotype.

4. The diagnostic method of claim 1, comprising generating a nucleic acid fragment which is diagnostic of K10 or K(-10) genotype.

5. The diagnostic method of claim 1, comprising generating a nucleic acid fragment which is diagnostic of K3, K4, and/or K21 genotype.

6. The diagnostic method of claim 1, wherein said generating step comprises selectively cleaving said nucleic acid sample to provide at least one cleavage fragment whose detection permits the differentiation of alleles of a Kell polymorphism; and wherein said detecting step comprises detecting said at least one cleavage fragment.

7. The diagnostic method of claim 6, wherein said selectively cleaving step comprises digesting said nucleic acid sample with at least one restriction enzyme which cleaves said nucleic acid sample differentially based on a nucleotide sequence difference at said Kell polymorphism locus.

8. The diagnostic method of claim 7, wherein said nucleic acid sample comprises a Kell K1/K2 polymorphism locus and said at least one restriction enzyme is BsmI.

9. The diagnostic method of claim 7, wherein said nucleic acid sample comprises a Kell K6/K7 polymorphism locus and said at least one restriction enzyme is selected from the group consisting of MnlI, DdeI, and a combination thereof.

10. The diagnostic method of claim 7, wherein said nucleic acid sample comprises a Kell K10/K(-10) polymorphism locus and said at least one restriction enzyme is AccI.

11. The diagnostic method of claim 7, wherein said nucleic acid sample comprises a Kell K3/K4/K21 polymorphism locus and said at least one restriction enzyme is selected from the group consisting of NlaIII, PvuII, and a combination thereof.

12. The diagnostic method of claim 6, wherein said generating step further comprises amplifying a Kell nucleic acid using a Kell allele-nonspecific primer to provide amplified Kell nucleic acid.

13. The diagnostic method of claim 12, wherein said generating step comprises amplifying said Kell nucleic acid prior to said selectively cleaving step.

14. The diagnostic method of claim 12, wherein said generating step comprises amplifying said Kell nucleic acid following said selectively cleaving step.

15. The diagnostic method of claim 12, wherein said amplifying step comprises amplifying nucleic acid by polymerase chain reaction, ligase chain reaction, or a combination thereof.

16. The diagnostic method of claim 1, wherein said generating step comprises:
   differentially amplifying said nucleic acid sample using a Kell allele-specific primer to provide said nucleic acid fragment.

17. The diagnostic method of claim 16, wherein said differentially amplifying step comprises differentially amplifying said nucleic acid sample by polymerase chain reaction, ligase chain reaction, or a combination thereof.

18. The diagnostic method of claim 16, wherein said differentially amplifying step comprises amplifying said nucleic acid sample using a Kell allele-specific primer which differentially amplifies alleles of a Kell polymorphism.

19. The diagnostic method of claim 18, wherein said differentially amplifying step comprises amplifying said nucleic acid sample using an allele-specific primer which differentially amplifies alleles of a K1/K2 polymorphism.

20. The diagnostic method of claim 18, wherein said differentially amplifying step comprises amplifying said nucleic acid sample using an allele-specific primer which differentially amplifies alleles of a K6/K7 polymorphism.

21. The diagnostic method of claim 18, wherein said differentially amplifying step comprises amplifying said nucleic acid sample using an allele-specific primer which differentially amplifies alleles of a K10/K(−10) polymorphism.

22. The diagnostic method of claim 18, wherein said differentially amplifying step comprises amplifying said nucleic acid sample using an allele-specific primer which differentially amplifies alleles of a K3/K4/K21 polymorphism.

23. The diagnostic method of claim 19, wherein said allele-specific primer includes a primer comprising a nucleotide sequence selected from the group consisting of: ATA CTG ACT CAT CAG AAG TTT CAG CA (SEQ ID NO:1), ATA CTG ACT CAT CAG AAG TCT CAG CA (SEQ ID NO:2), and ATA CTG ACT CAT CAG AAG TGT CAG CA (SEQ ID NO:61).

24. The diagnostic method of claim 19, wherein said allele-specific primer includes a primer comprising the nucleotide sequence: TGG ACT TCC TTA AAC TTT AAC TGA AC (SEQ ID NO:3).

25. The diagnostic method of claim 18, wherein said primer includes a primer comprising a nucleotide sequence selected from the group consisting of: TTT AGT CCT CAC TCC CAT GCT TCC (SEQ ID NO:4), and TAT CAC ACA GGT GTC CTC TCT TCC (SEQ ID NO:5), TTA GTC CTC ACT CNC CAT GCT TCC (SEQ ID NO:62), and TCA CAC AGG TGT CCT CTC TTC C (SEQ ID NO:63).

26. The diagnostic method of claim 1, wherein said nucleic acid product comprises one or more nucleic acid fragments; and wherein said generating step comprises:

separating said one or more nucleic acid fragments to provide a fragment pattern, wherein said fragment pattern permits differentiation of alleles of a Kell polymorphism.

27. The diagnostic method of claim 26, wherein said separating step provides a fragment pattern which permits differentiation of K1/K2 genotype.

28. The diagnostic method of claim 26, wherein said separating step provides a fragment pattern which permits differentiation of K6/K7 genotype.

29. The diagnostic method of claim 26, wherein said separating step provides a fragment pattern which permits differentiation of K10/K(−10) genotype.

30. The diagnostic method of claim 26, wherein said separating step provides a fragment pattern which permits differentiation of K3/K4/K21 genotype.

31. The diagnostic method of claim 26, wherein said detecting step comprises detecting one or more of the nucleic acid fragments in the fragment pattern.

32. The diagnostic method of claim 31, wherein said detecting step includes marking said one or more nucleic acid fragments with a sequence non-specific marker.

33. The diagnostic method of claim 31, wherein said detecting step includes specifically marking said one or more nucleic acid fragments with one or more Kell allele-specific hybridization probes.

34. The diagnostic method of claim 33, wherein each of said hybridization probes is detectably labeled.

35. The diagnostic method of claim 1, further comprising determining a non-Kell genotype of said subject.

36. The diagnostic method of claim 1, further comprising determining a Kell phenotype of said subject.

37. The diagnostic method of claim 36, wherein said determining step comprises determining a Kell phenotype of said subject by serological testing.

38. The diagnostic method of claim 1, further comprising obtaining a DNA sample from a subject.

39. The diagnostic method of claim 38, wherein said DNA sample comprises genomic DNA.

40. The diagnostic method of claim 38, wherein said obtaining step comprises obtaining a DNA sample from a biological sample containing erythroid tissue of the subject.

41. The diagnostic method of claim 40, wherein said biological sample comprises amniotic fluid or chorionic villus and wherein said subject is a fetus in utero.

42. The diagnostic method of claim 40, wherein said biological sample comprises a blood sample.

43. A nucleic acid oligomer, comprising a nucleic acid sequence that specifically binds to a region of Kell DNA diagnostic of at least one of K1 and/or K2 DNA; K6 and/or K7 DNA; K10 and/or K(−10) DNA; and K3 and/or K4 and/or K21 DNA.

44. The nucleic acid oligomer of claim 43, wherein said oligomer is detectably labeled.

45. The nucleic acid oligomer of claim 43, wherein said oligomer is attached to a substrate.

46. The nucleic acid oligomer of claim 43, wherein said nucleic acid sequence is exactly complementary to said region of Kell DNA.

47. A nucleic acid oligomer having a nucleic acid sequence that encodes a region of a Kell protein containing at least one of the K1 domain, the K6 domain, the K10 domain, and the K3 or K21 domain.

48. The nucleic acid oligomer of claim 47, wherein said oligomer is detectably labeled.

49. The nucleic acid oligomer of claim 47, wherein said oligomer is attached to a substrate.

50. A nucleic acid primer set, comprising at least one nucleic acid oligomer that specifically binds to or causes elongation through a region of Kell DNA comprising K1 DNA and/or K2 DNA; K6 DNA and/or K7 DNA; K1O DNA and/or K(−10) DNA; or K3 DNA and/or K4 DNA and/or K21 DNA.

51. The nucleic acid primer set of claim 50, wherein the primer set comprises a nucleic acid oligomer that specifically binds to or causes elongation through Kell nucleic acid comprising a K1/K2 polymorphism locus.

52. The nucleic acid primer set of claim 50, wherein the primer set comprises a nucleic acid oligomer that specifically binds to or causes elongation through Kell nucleic acid comprising a K6/K7 polymorphism locus.

53. The nucleic acid primer set of claim 50, wherein the primer set comprises a nucleic acid oligomer that specifically binds to or causes elongation through Kell nucleic acid comprising a K10/K(−10) polymorphism locus.

54. The nucleic acid primer set of claim 50, wherein the primer set comprises a nucleic acid oligomer that specifically binds to or causes elongation through Kell nucleic acid comprising a K3/K4/K21 polymorphism locus.

55. A polypeptide having an amino acid sequence which comprises a region of a Kell protein comprising at least one of the K1 domain, the K6 domain, the K10 domain, the K3 domain, and the K21 domain.

56. The Kell-based polypeptide of claim 55, wherein said polypeptide is detectably labeled.

57. The Kell-based polypeptide of claim 55, wherein said polypeptide is attached to a substrate.

58. The polypeptide of claim 55, wherein said amino acid sequence includes a methionine residue at amino acid 193 of the Kell protein.

59. The polypeptide of claim 55, wherein said amino acid sequence includes a proline residue at amino acid 597 of the Kell protein.

60. The polypeptide of claim 55, wherein said amino acid sequence includes a valine residue at amino acid 494 of the Kell protein.

61. The polypeptide of claim 55, wherein said amino acid sequence includes a tryptophan residue at amino acid 281 of the Kell protein.

62. The polypeptide of claim 55, wherein said amino acid sequence includes a glutamine residue at amino acid 281 of the Kell protein.

63. A diagnostic method for detecting alloimmunization of a patient to a Kell antigen, comprising:

measuring a parameter of immune reactivity of a blood sample of a patient with a peptide probe, wherein said peptide probe comprises an amino acid sequence of at least a portion of a Kell protein comprising the K1 domain, the K6 domain, the K10 domain the K3 domain, or the K21 domain, and wherein said peptide probe is specifically reactive with anti-Kell antibodies in the sample.

64. A diagnostic kit for the differential determination of a Kell genotype, comprising:

(a) a primer which specifically amplifies a region of Kell DNA including at least one of the K1/K2 polymorphism locus, the K6/K7 polymorphism locus, the K10/K(-10) polymorphism locus, and the K3/K4/K21 polymorphism locus; and (b) a container.

65. The diagnostic kit of claim 64, wherein said kit further comprises at least one restriction endonuclease which selectively cleaves Kell nucleic acid comprising at least one of said polymorphism loci to provide nucleic acid fragments whose detection permits the differential identification of a Kell genotype.

66. A diagnostic kit for determining a Kell genotype by detecting target nucleic acid sequences specific to Kell alleles, said kit comprising:

(a) a primer set including at least two PCR primers wherein each of the PCR primers is an oligonucleotide that specifically binds to or causes elongation through a sequence specific to one of at least two Kell alleles, wherein the at least two Kell alleles differ at the K1/K2 polymorphism locus, the K6/K7 polymorphism locus, the K10/K(-10) polymorphism locus, or the K3/K4/K21 polymorphism locus; and (b) a microtiter plate having a plurality of wells and having bound thereto oligonucleotide capture probes which specifically hybridize to said target sequences.

67. A recombinant expression vector capable of transforming a cell to cause expression of Kell protein, comprising a nucleic acid sequence encoding at least a part of a Kell protein comprising the K1 domain, the K6 domain, the K10 domain, the K3 domain, or the K21 domain.

68. A method of producing a cell line transformed to express a Kell protein, comprising transforming a cell by means of the recombinant expression vector of claim 67 to produce a transformed cell, and establishing a stable transformed cell line derived from said transformed cell.

69. A transformed cell line produced according to the method of claim 68.

70. A nucleic acid sequence, which encodes at least a fragment of a Kell protein including at least one of a K1 domain, a K6 domain, a K1O domain, a K3 domain, and a K21 domain.

71. A nucleic acid sequence according to claim 70, comprising a Kell cDNA which encodes a Kell protein which includes at least one of a K1 domain, a K6 domain, a K10 domain, a K3 domain, and a K21 domain.

72. The nucleic acid primer set of claim 51, wherein the primer set comprises:

a K1 primer that specifically binds to or causes elongation through K1 DNA and a K2 primer that specifically binds to or causes elongation through K2 DNA.

73. The nucleic acid primer set of claim 52, wherein the primer set comprises:

a K6 primer that specifically binds to or causes elongation through K6 DNA and a K7 primer that specifically binds to or causes elongation through K7 DNA.

74. The nucleic acid primer set of claim 53, wherein the primer set comprises:

a K10 primer that specifically binds to or causes elongation through K10 DNA and a K(-10) primer that specifically binds to or causes elongation through K(-10) DNA.

75. The nucleic acid primer set of claim 54, wherein the primer set comprises at least two of:

a K3 primer that specifically binds to or causes elongation through K3 DNA, a K4 primer that specifically binds to or causes elongation through K4 DNA, and a K21 primer that specifically binds to or causes elongation through K21 DNA.

* * * * *

UNITED STATES PATENT AND TRADEMARK OFFICE
CERTIFICATE OF CORRECTION

PATENT NO.   : 5,804,379
DATED        : September 8, 1998
INVENTOR(S)  : Lee, et al.

It is certified that error appears in the above-identified patent and that said Letters Patent is hereby corrected as shown below:

| | |
|---|---|
| On the titlep page, Item [54] and Column 1, Line 1, | delete "METHODS" and insert therefor --METHOD--. |
| In Column 16, Lines 14-15, | delete "by marking or some" and insert therefor --by marking or staining some--. |
| In Column 16, Lines 15-16, | delete "specifically or non-staining specifically" and insert therefor --specifically or non-specifically--. |
| In Column 19, Line 50, | delete "Hybond #" and insert therefor --Hybond™--. |
| In Column 25, Line 34, | delete "Triton-X1000" and insert therefor --Triton-X100--. |
| In Column 29, Line 13, | delete "tag DNA" and insert therefor --*taq* DNA--. |

Signed and Sealed this

Twenty-third Day of March, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:1:

ATACTGACTC ATCAGAAGTT TCAGCA       26

( 2 ) INFORMATION FOR SEQ ID NO:2:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:2:

ATACTGACTC ATCAGAAGTC TCAGCA       26

( 2 ) INFORMATION FOR SEQ ID NO:3:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:3:

TGGACTTCCT TAAACTTTAA CTGAAC       26

( 2 ) INFORMATION FOR SEQ ID NO:4:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:4:

TTTAGTCCTC ACTCCCATGC TTCC       24

( 2 ) INFORMATION FOR SEQ ID NO:5:

( i ) SEQUENCE CHARACTERISTICS:
        ( A ) LENGTH: 24 nucleotides ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:5:

TATCACACAG GTGTCCTCTC TTCC 24

( 2 ) INFORMATION FOR SEQ ID NO:6:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE:genomic DNA ( i i i ) HYPOTHETICAL: no ( x i ) SEQUENCE DESCRIPTION: SEQ ID NO:6:

GGAGACTTCC AAGGTCTTAG CTATCACTTA AGCAC 35

( 2 ) INFORMATION FOR SEQ ID NO:7:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:7:

CTGGTTCGGC CCACCTCTGA AGGTTCCAGA ATCGATAG 38

( 2 ) INFORMATION FOR SEQ ID NO:8:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:8:

CTCGGCTCTT CCTCACTTTG GTCC 24

( 2 ) INFORMATION FOR SEQ ID NO:9:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:9:

CTCTTGGCTC CAGAGAGTTC CCAT 24

( 2 ) INFORMATION FOR SEQ ID NO:10:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:10:

CCCACCTTCC ATCTGTCTAT CTTC     24

( 2 ) INFORMATION FOR SEQ ID NO:11:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:11:

GACTCGAGTC GACAACGTTT TTTTTTTTT TTTTT     35

( 2 ) INFORMATION FOR SEQ ID NO:12:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:12:

ATGGGGAGAC TGTCCTG     17

( 2 ) INFORMATION FOR SEQ ID NO:13:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:13:

CAGTCCTCCG AATCAGCTCC TAGA     24

( 2 ) INFORMATION FOR SEQ ID NO:14:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no (x i) SEQUENCE DESCRIPTION: SEQ ID NO:14:

CTCTTGGCTC CAGAGAGTTC CCAT 24

(2) INFORMATION FOR SEQ ID NO:15:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (i i) MOLECULE TYPE: genomic DNA (i i i) HYPOTHETICAL: no (x i) SEQUENCE DESCRIPTION: SEQ ID NO:15:

GAAGGTGGGG ACCAAAGTGA GGAA 24

(2) INFORMATION FOR SEQ ID NO:16:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (i i) MOLECULE TYPE: genomic DNA (i i i) HYPOTHETICAL: no (x i) SEQUENCE DESCRIPTION: SEQ ID NO:16:

ACAGGGTTTG GAGCAGTCAT GGTC 24

(2) INFORMATION FOR SEQ ID NO:17:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (i i) MOLECULE TYPE: genomic DNA (i i i) HYPOTHETICAL: no (x i) SEQUENCE DESCRIPTION: SEQ ID NO:17:

ATATTCCCCA CCTCCCCACA CCTG 24

(2) INFORMATION FOR SEQ ID NO:18:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (i i) MOLECULE TYPE: genomic DNA (i i i) HYPOTHETICAL: no (x i) SEQUENCE DESCRIPTION: SEQ ID NO:18:

ATCTACGGTG CTCAGGCTCT CCTC 24

(2) INFORMATION FOR SEQ ID NO:19:

(i) SEQUENCE CHARACTERISTICS:
        (A) LENGTH: 24 nucleotides
        (B) TYPE: nucleic acid
        (C) STRANDEDNESS: single (D) TOPOLOGY: linear (ii) MOLECULE TYPE: genomic DNA (iii) HYPOTHETICAL: no (xi) SEQUENCE DESCRIPTION: SEQ ID NO:19:

GGAAGCATGG GAGTGAGGAC TAAA 24

(2) INFORMATION FOR SEQ ID NO:20:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:20:

TGGCATCCAT GGTACCTCAT GGAA 24

(2) INFORMATION FOR SEQ ID NO:21:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:21:

GAGGCTTTTG AAACCCCAGG ATGA 24

(2) INFORMATION FOR SEQ ID NO:22:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:22:

TTCCCCAGCC ACCTGCCATC TCAT 24

(2) INFORMATION FOR SEQ ID NO:23:

(i) SEQUENCE CHARACTERISTICS:
(A) LENGTH: 24 nucleotides
(B) TYPE: nucleic acid
(C) STRANDEDNESS: single
(D) TOPOLOGY: linear (ii) MOLECULE TYPE: genomic DNA (iii) HYPOTHETICAL: no (xi) SEQUENCE DESCRIPTION: SEQ ID NO:23:

CCCTTTTCCA AGGGTCAGAA GCTG 24

(2) INFORMATION FOR SEQ ID NO:24:

( i ) SEQUENCE CHARACTERISTICS:
    ( A ) LENGTH: 24 nucleotides
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( x i ) SEQUENCE DESCRIPTION: SEQ ID NO:24:

GGGCTTATTT GACCCCAGA ATCT    24

( 2 ) INFORMATION FOR SEQ ID NO:25:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:25:

CCTAATCCCT GGATGCCTGC CTGT    24

( 2 ) INFORMATION FOR SEQ ID NO:26:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:26:

CAGTGAGGAC ATCTGCAGAA GAGG    24

( 2 ) INFORMATION FOR SEQ ID NO:27:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:27:

TCCTGTGGAC CCTCCCCCTT CAAT    24

( 2 ) INFORMATION FOR SEQ ID NO:28:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:28:

GGGCGGAAGC CAAGTGCCAG CTTTT                                                                    25

( 2 ) INFORMATION FOR SEQ ID NO:29:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:29:

AATAAAAGCT GGCACTTGGC TTCCGCCGGA ATTC                                                           34

( 2 ) INFORMATION FOR SEQ ID NO:30:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:30:

AATAAAAGCT GGCACTTGGC TTCCG                                                                    25

( 2 ) INFORMATION FOR SEQ ID NO:31:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:31:

AATAAAAGCT GGCACTTGGC TTCC                                                                     24

( 2 ) INFORMATION FOR SEQ ID NO:32:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:32:

AATAAAAGCT GGCACTTGGC TTC                                                                      23

( 2 ) INFORMATION FOR SEQ ID NO:33:

( i ) SEQUENCE CHARACTERISTICS:
        ( A ) LENGTH: 19 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:33:

AATAAAAGCT GGCACTTGG                                                                19

( 2 ) INFORMATION FOR SEQ ID NO:34:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:34:

AATAAAAGCT GGCACTTGGC TTCC                                                          24

( 2 ) INFORMATION FOR SEQ ID NO:35:

( i ) SEQUENCE CHARACTERISTICS:
        ( A ) LENGTH: 34 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:35:

AATAAAAGCT GGCACTTGGC TTCCGCTTGT CTCT                                               34

( 2 ) INFORMATION FOR SEQ ID NO:36:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:36:

AATAAAAGCT GGCACTTGGC TTCCGCTTGT CTCTT                                              35

( 2 ) INFORMATION FOR SEQ ID NO:37:

( i ) SEQUENCE CHARACTERISTICS:
        ( A ) LENGTH: 148 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:37:

GAAGTGCCCC TTCTCCAGGA TCAAGGAACT GGGGCGGGGG GTGTTTCCTG                               50

GACCCCAGTC CTCCGAATCA GCTCCTAGAG TGGAACCAGG AAGGATTCTG                              100

GAGCCACAGA AGATAGACAG ATG GTAAGTCCCC TTTTGGAGTC AGAGG                               148
                                          Met ( 2 ) INFORMATION FOR SEQ ID NO:38:

( i ) SEQUENCE CHARACTERISTICS:
        ( A ) LENGTH: 128 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:38:

```
CTCCTTCTCC CTCCACTCAC TTCAG GAA GGT GGG GAC CAA AGT GAG GAA          49
                            Glu Gly Gly Asp Gln Ser Glu Glu
                            1                 5

GAG CCG AGG GAA CGC AGC CAG GCA GGT GGA ATG GGA ACT CTC TGG          94
Glu Pro Arg Glu Arg Ser Gln Ala Gly Gly Met Gly Thr Leu Trp
    10              15                  20

AGC CAA GAG GTAAGTGGCC TCCTCTCCTG GGTCT                             128
Ser Gln Glu
    25
```

( 2 ) INFORMATION FOR SEQ ID NO:39:

( i ) SEQUENCE CHARACTERISTICS:
        ( A ) LENGTH: 207 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:39:

```
TTTCACCTCT TGGTTCCTCC CACAG AGC ACT CCA GAA GAG AGG CTG CCC          49
                            Ser Thr Pro Glu Glu Arg Leu Pro
                            1                 5

GTG GAA GGG AGC AGG CCA TGG GCA GTG GCC AGG CGG GTG CTG ACA          94
Val Glu Gly Ser Arg Pro Trp Ala Val Ala Arg Arg Val Leu Thr
    10              15                  20

GCT ATC CTG ATT TTG GGC CTG CTC CTT TGT TTT TCT CTC CTT TGT         139
Ala Ile Leu Ile Leu Gly Leu Leu Leu Cys Phe Ser Leu Leu Cys
    25              30                  35

TTT TCT GTG CTT TTG TTC TAC AAC TTC CAG AAC TGT GGC CCT C           182
Phe Ser Val Leu Leu Phe Tyr Asn Phe Gln Asn Cys Gly Pro
    40              45                  50

GTAAGCAAGA TCCCAGACCC CCCAA                                         207
```

( 2 ) INFORMATION FOR SEQ ID NO:40:

( i ) SEQUENCE CHARACTERISTICS:
        ( A ) LENGTH: 227 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:40:

```
CCCAGCTCTG AGCTTTTCCC CACAG GC CCC TGT GAG ACA TCT GTG TGT           48
                               Arg Pro Cys Glu Thr Ser Val Cys
                               1                 5
```

| | | | | | | | | | | | | | | |
|---|---|---|---|---|---|---|---|---|---|---|---|---|---|---|
| TTG | GAT | CTC | CGG | GAT | CAT | TAC | CTG | GCC | TCT | GGG | AAC | ACA | AGT | GTG | 93 |
| Leu | Asp | Leu | Arg | Asp | His | Tyr | Leu | Ala | Ser | Gly | Asn | Thr | Ser | Val | |
| | | 10 | | | 15 | | | | | 20 | | | | | |
| GCC | CCC | TGC | ACC | GAC | TTC | TTC | AGC | TTT | GCC | TGT | GGA | AGG | GCC | AAA | 138 |
| Ala | Pro | Cys | Thr | Asp | Phe | Phe | Ser | Phe | Ala | Cys | Gly | Arg | Ala | Lys | |
| | 25 | | | | | 30 | | | | | 35 | | | | |
| GAG | ACC | AAT | AAT | TCT | TTT | CAG | GAG | CTT | GCC | ACA | AAG | AAC | AAA | AAC | 183 |
| Glu | Thr | Asn | Asn | Ser | Phe | Gln | Glu | Leu | Ala | Thr | Lys | Asn | Lys | Asn | |
| | 40 | | | | | 45 | | | | | 50 | | | | |

CGA CTT CGG AGA ATA CTG G GTGAGGAAAG CAGGGTGGAA GATGC    227
Arg Leu Arg Arg Ile Leu
        55

( 2 ) INFORMATION FOR SEQ ID NO:41:

( i ) SEQUENCE CHARACTERISTICS:
        ( A ) LENGTH: 181 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:41:

TTTAGTCCTC ACTCCCATGC TTCCTTTCTA G AG GTC CAG AAT TCC TGG    48
                                  Glu Val Gln Asn Ser Trp
                                   1               5

| | | | | | | | | | | | | | | |
|---|---|---|---|---|---|---|---|---|---|---|---|---|---|---|
| CAC | CCA | GGC | TCT | GGG | GAG | GAG | AAA | GCC | TTC | CAG | TTC | TAC | AAC | TCC | 93 |
| His | Pro | Gly | Ser | Gly | Glu | Glu | Lys | Ala | Phe | Gln | Phe | Tyr | Asn | Ser | |
| | | | 10 | | | | 15 | | | | | | 20 | | |
| TGC | ATG | GAT | ACA | CTT | GCC | ATT | GAA | GCT | GCA | GGG | ACT | GGT | CCC | CTC | 138 |
| Cys | Met | Asp | Thr | Leu | Ala | Ile | Glu | Ala | Ala | Gly | Thr | Gly | Pro | Leu | |
| | | | 25 | | | | | 30 | | | | | 35 | | |

AGA CAA GTT ATT GAG GAG GTGAGAAAAG TTGGGATATT AACTT    181
Arg Gln Val Ile Glu Glu
            40

( 2 ) INFORMATION FOR SEQ ID NO:42:

( i ) SEQUENCE CHARACTERISTICS:
        ( A ) LENGTH: 197 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:42:

TCAGCCCCCT CTCTCTCCTT TAAAG CTT GGA GGC TGG CGC ATC TCT GGT    49
                             Leu Gly Gly Trp Arg Ile Ser Gly
                              1               5

| | | | | | | | | | | | | | | |
|---|---|---|---|---|---|---|---|---|---|---|---|---|---|---|
| AAA | TGG | ACT | TCC | TTA | AAC | TTT | AAC | CGA | ACG | CTG | AGA | CTT | CTG | ATG | 94 |
| Lys | Trp | Thr | Ser | Leu | Asn | Phe | Asn | Arg | Thr | Leu | Arg | Leu | Leu | Met | |
| | | 10 | | | | | 15 | | | | | 20 | | | |
| AGT | CAG | TAT | GGC | CAT | TTC | CCT | TTC | TTC | AGA | GCC | TAC | CTA | GGA | CCT | 139 |
| Ser | Gln | Tyr | Gly | His | Phe | Pro | Phe | Phe | Arg | Ala | Tyr | Leu | Gly | Pro | |
| | 25 | | | | | 30 | | | | | 35 | | | | |
| CAT | CCT | GCC | TCT | CCA | CAC | ACA | CCA | GTC | ATC | CAG | | | | | 182 |
| His | Pro | Ala | Ser | Pro | His | Thr | Pro | Val | Ile | Gln | GTGAGGGATG | | | | |
| | 40 | | | | | 45 | | | | | | | | | |

CACTGGCGAA GACAC    197

( 2 ) INFORMATION FOR SEQ ID NO:43:

( i ) SEQUENCE CHARACTERISTICS:
        ( A ) LENGTH: 113 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:43:

```
TCTCTCCAGT CTCTCTTGTG CCCAG ATA GAC CAG CCA GAG TTT GAT GTT          49
                            Ile Asp Gln Pro Glu Phe Asp Val
                            1               5

CCC CTC AAG CAA GAT CAA GAA CAG AAG ATC TAT GCC CAG GTAAG            93
Pro Leu Lys Gln Asp Gln Glu Gln Lys Ile Tyr Ala Gln
        10              15                  20

ATGGCACATG GACAAAGGCC                                               113
```

( 2 ) INFORMATION FOR SEQ ID NO:44:

( i ) SEQUENCE CHARACTERISTICS:
        ( A ) LENGTH: 239 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:44:

```
TGTGACTGAC ATTTCCTTCC TCCAG ATC TTT CGG GAA TAC CTG ACT TAC          49
                            Ile Phe Arg Glu Tyr Leu Thr Tyr
                            1               5

CTG AAT CAG CTG GGA ACC TTG CTG GGA GGA GAC CCA AGC AAG GTG          94
Leu Asn Gln Leu Gly Thr Leu Leu Gly Gly Asp Pro Ser Lys Val
        10              15                  20

CAA GAA CAC TCT TCC TTG TCA ATC TCC ATC ACT TCA CGG CTG TTC         139
Gln Glu His Ser Ser Leu Ser Ile Ser Ile Thr Ser Arg Leu Phe
    25              30                  35

CAG TTT CTG AGG CCC CTG GAG CAG CGG CGG GCA CAG GGC AAG CTC         184
Gln Phe Leu Arg Pro Leu Glu Gln Arg Arg Ala Gln Gly Lys Leu
    40              45                  50

TTC CAG ATG GTC ACT ATC GAC CAG CTC AAG GTGCCTGGAA                  224
Phe Gln Met Val Thr Ile Asp Gln Leu Lys
    55              60

CTGGGGGGCA GAAGA                                                    239
```

( 2 ) INFORMATION FOR SEQ ID NO:45:

( i ) SEQUENCE CHARACTERISTICS:
        ( A ) LENGTH: 199 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:45:

```
CTCAGCTTTG TGTCCCTCCT CTAAG GAA ATG GCC CCC GCC ATC GAC TGG          49
                            Glu Met Ala Pro Ala Ile Asp Trp
                            1               5
```

| | | | | | | | | | | | | | | |
|---|---|---|---|---|---|---|---|---|---|---|---|---|---|---|
| TTG | TCC | TGC | TTG | CAA | GCG | ACA | TTC | ACA | CCG | ATG | TCC | CTG | AGC | CCT | 94
| Leu | Ser | Cys | Leu | Gln | Ala | Thr | Phe | Thr | Pro | Met | Ser | Leu | Ser | Pro |
| | 10 | | | | | 15 | | | | | 20 | | | |

| | | | | | | | | | | | | | | |
|---|---|---|---|---|---|---|---|---|---|---|---|---|---|---|
| TCT | CAG | TCC | CTC | GTG | GTC | CAT | GAC | GTG | GAA | TAT | TTG | AAA | AAC | ATG | 139
| Ser | Gln | Ser | Leu | Val | Val | His | Asp | Val | Glu | Tyr | Leu | Lys | Asn | Met |
| | 25 | | | | | 30 | | | | | 35 | | | |

| | | | | | | | | | | |
|---|---|---|---|---|---|---|---|---|---|---|
| TCA | CAA | CTG | GTG | GAG | GAG | ATG | CTG | CTA | AAG | CAG | AG GTTCGCCGCA | 184
| Ser | Gln | Leu | Val | Glu | Glu | Met | Leu | Leu | Lys | Gln | Arg |
| | 40 | | | | | 45 | | | | | 50 |

GGTGGGATTG GGGAG 199

(2) INFORMATION FOR SEQ ID NO:46:

(i) SEQUENCE CHARACTERISTICS:
        (A) LENGTH: 180 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:46:

| | | | | | | | | | | |
|---|---|---|---|---|---|---|---|---|---|---|
| GTGTGGGTCT | CTTTTGTCTC | CATAG | G | GAC | TTT | CTG | CAG | AGC | CAC | ATG | 47
| | | | | Asp | Phe | Leu | Gln | Ser | His | Met |
| | | | | 1 | | | | 5 | | |

| | | | | | | | | | | | | | | |
|---|---|---|---|---|---|---|---|---|---|---|---|---|---|---|
| ATC | TTA | GGG | CTG | GTG | GTG | ACC | CTT | TCT | CCA | GCC | CTG | GAC | AGT | CAA | 92
| Ile | Leu | Gly | Leu | Val | Val | Thr | Leu | Ser | Pro | Ala | Leu | Asp | Ser | Gln |
| | 10 | | | | | 15 | | | | | 20 | | | |

| | | | | | | | | | | | | | | |
|---|---|---|---|---|---|---|---|---|---|---|---|---|---|---|
| TTC | CAG | GAG | GCA | CGC | AGA | AAG | CTC | AGC | CAG | AAA | CTG | CGG | GAA | CTG | 137
| Phe | Gln | Glu | Ala | Arg | Arg | Lys | Leu | Ser | Gln | Lys | Leu | Arg | Glu | Leu |
| | 25 | | | | | 30 | | | | | 35 | | | |

| | | | | | | | |
|---|---|---|---|---|---|---|---|
| ACA | GAG | CAA | CCA | CCC | ATG | GTGAGGAGAG | GAGCGGGTGT ATTTG | 180
| Thr | Glu | Gln | Pro | Pro | Met |
| | 40 | | | | |

(2) INFORMATION FOR SEQ ID NO:47:

(i) SEQUENCE CHARACTERISTICS:
        (A) LENGTH: 161 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:47:

| | | | | | | | | | |
|---|---|---|---|---|---|---|---|---|---|
| ACTCATTCCA | GCTTTGTCTC | CATAG | CCT | GCC | CGC | CCA | CGA | TGG | ATG AAG | 49
| | | | Pro | Ala | Arg | Pro | Arg | Trp | Met Lys |
| | | | 1 | | | | 5 | | |

| | | | | | | | | | | | | | | |
|---|---|---|---|---|---|---|---|---|---|---|---|---|---|---|
| TGC | GTG | GAG | GAG | ACA | GGC | ACG | TTC | TTC | GAG | CCC | ACG | CTG | GCG | GCT | 94
| Cys | Val | Glu | Glu | Thr | Gly | Thr | Phe | Phe | Glu | Pro | Thr | Leu | Ala | Ala |
| | 10 | | | | | 15 | | | | | 20 | | | |

| | | | | | | | | | | | | | | |
|---|---|---|---|---|---|---|---|---|---|---|---|---|---|---|
| TTG | TTT | GTT | CGT | GAG | GCC | TTT | GGC | CCG | AGC | ACC | CGA | AGT | GCT | | 136
| Leu | Phe | Val | Arg | Glu | Ala | Phe | Gly | Pro | Ser | Thr | Arg | Ser | Ala | |
| | 25 | | | | | 30 | | | | | 35 | | | |

GTATGTGAGA GCTCTTCCCA GCCCA 161

(2) INFORMATION FOR SEQ ID NO:48:

(i) SEQUENCE CHARACTERISTICS:
        (A) LENGTH: 149 nucleotides (B) TYPE: nucleic acid
(C) STRANDEDNESS: single
(D) TOPOLOGY: linear (i i) MOLECULE TYPE: genomic DNA (i i i) HYPOTHETICAL: no (x i) SEQUENCE DESCRIPTION: SEQ ID NO:48:

| CTGTCCCTGG | ACCTCACTCC | CACAG | GCC | ATG | AAA | TTA | TTC | ACT | GCG | ATC | 49 |
|---|---|---|---|---|---|---|---|---|---|---|---|
| | | | Ala | Met | Lys | Leu | Phe | Thr | Ala | Ile | |
| | | | 1 | | | | 5 | | | | |

| CGG | GAT | GCC | CTC | ATC | ACT | CGC | CTC | AGA | AAC | CTT | CCC | TGG | ATG | AAT | 94 |
|---|---|---|---|---|---|---|---|---|---|---|---|---|---|---|---|
| Arg | Asp | Ala | Leu | Ile | Thr | Arg | Leu | Arg | Asn | Leu | Pro | Trp | Met | Asn | |
| 10 | | | | | 15 | | | | | 20 | | | | | |

| GAG | GAG | ACC | CAG | AAC | ATG | GCC | CAG | GAC | AAG | GTCAGGCCAG | 134 |
|---|---|---|---|---|---|---|---|---|---|---|---|
| Glu | Glu | Thr | Gln | Asn | Met | Ala | Gln | Asp | Lys | | |
| 25 | | | | | 30 | | | | | | |

GCGTCCTGGC TGGTG     149

(2) INFORMATION FOR SEQ ID NO:49:

(i) SEQUENCE CHARACTERISTICS:
(A) LENGTH: 128 nucleotides
(B) TYPE: nucleic acid
(C) STRANDEDNESS: single
(D) TOPOLOGY: linear (i i) MOLECULE TYPE: genomic DNA (i i i) HYPOTHETICAL: no (x i) SEQUENCE DESCRIPTION: SEQ ID NO:49:

| TAGCCTCTTC | TGTGTCTCTC | TCCAG | GTT | GCT | CAA | CTG | CAG | GTG | GAG | ATG | 49 |
|---|---|---|---|---|---|---|---|---|---|---|---|
| | | | Val | Ala | Gln | Leu | Gln | Val | Glu | Met | |
| | | | 1 | | | | 5 | | | | |

| GGG | GCT | TCA | GAA | TGG | GCC | CTG | AAG | CCA | GAG | CTG | GCC | CGA | CAA | GAA | 94 |
|---|---|---|---|---|---|---|---|---|---|---|---|---|---|---|---|
| Gly | Ala | Ser | Glu | Trp | Ala | Leu | Lys | Pro | Glu | Leu | Ala | Arg | Gln | Glu | |
| 10 | | | | | 15 | | | | | 20 | | | | | |

| TAC | AAC | GAT | GTGGGTCCCT | GTGTTTTCCA | GCTCC | 128 |
|---|---|---|---|---|---|---|
| Tyr | Asn | Asp | | | | |
| 25 | | | | | | |

(2) INFORMATION FOR SEQ ID NO:50:

(i) SEQUENCE CHARACTERISTICS:
(A) LENGTH: 151 nucleotides
(B) TYPE: nucleic acid
(C) STRANDEDNESS: single
(D) TOPOLOGY: linear (i i) MOLECULE TYPE: genomic DNA (i i i) HYPOTHETICAL: no (x i) SEQUENCE DESCRIPTION: SEQ ID NO:50:

| AAGTCACCTC | CTGCCTCTTC | CCCAG | ATA | CAG | CTT | GGA | TCG | AGC | TTC | CTG | 49 |
|---|---|---|---|---|---|---|---|---|---|---|---|
| | | | Ile | Gln | Leu | Gly | Ser | Ser | Phe | Leu | |
| | | | 1 | | | | 5 | | | | |

| CAG | TCT | GTC | CTG | AGC | TGT | GTC | CGG | TCC | CTC | CGA | GCT | AGA | ATT | GTC | 94 |
|---|---|---|---|---|---|---|---|---|---|---|---|---|---|---|---|
| Gln | Ser | Val | Leu | Ser | Cys | Val | Arg | Ser | Leu | Arg | Ala | Arg | Ile | Val | |
| 10 | | | | | 15 | | | | | | | 25 | | | |

| CAG | AGC | TTC | TTG | CAG | CCT | CAC | CCC | CAA | CAC | AG | GTATGACAGC | AGGGG | 141 |
|---|---|---|---|---|---|---|---|---|---|---|---|---|---|
| Gln | Ser | Phe | Leu | Gln | Pro | His | Pro | Gln | His | Arg | | | |
| 30 | | | | | 35 | | | | | | | | |

AGACACAGGC     151

( 2 ) INFORMATION FOR SEQ ID NO:51:

( i ) SEQUENCE CHARACTERISTICS:
        ( A ) LENGTH: 161 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:51:

```
GAGTTCACAT GTCCTCTTCC CACAG G TGG AAG GTG TCC CCT TGG GAC           47
                              Trp Lys Val Ser Pro Trp Asp
                               1               5

GTC AAT GCT TAC TAT TCG GTA TCT GAC CAT GTG GTA GTC TTT CCA         92
Val Asn Ala Tyr Tyr Ser Val Ser Asp His Val Val Val Phe Pro
         10                  15                      20

GCT GGA CTC CTC CAA CCC CCA TTC TTC CAC CCT GGC TAT CCC AG         136
Ala Gly Leu Leu Gln Pro Pro Phe Phe His Pro Gly Tyr Pro Arg
         25                  30                      35

GTATGGGTCA CTCTGTAAGG GTAGG                                        161
```

( 2 ) INFORMATION FOR SEQ ID NO:52:

( i ) SEQUENCE CHARACTERISTICS:
        ( A ) LENGTH: 118 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:52:

```
GTCAAATAAG CCCTTGTCTC CCTAG A GCC GTG AAC TTT GGC GCT GCT           47
                              Ala Val Asn Phe Gly Ala Ala
                               1               5

GGC AGC ATC ATG GCC CAC GAG CTG TTG CAC ATC TTC TAC CAG CTC         92
Gly Ser Ile Met Ala His Glu Leu Leu His Ile Phe Tyr Gln Leu
         10                  15                      20

T GTGGGTAACA GGGGCCACTG GGAGG                                      118
```

( 2 ) INFORMATION FOR SEQ ID NO:53:

( i ) SEQUENCE CHARACTERISTICS:
        ( A ) LENGTH: 220 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:53:

```
TGTTCTCTTG TCCCATTTTC AACAG TA CTG CCT GGG GGC TGC CTC GCC          48
                              Leu Leu Pro Gly Gly Cys Leu Ala
                               1                5

TGT GAC AAC CAT GCC CTC CAG GAA GCT CAC CTG TGC CTG AAG CGC         93
Lys Asp Asn His Ala Leu Gln Glu Ala His Leu Cys Leu Lys Arg
         10                  15                      20

CAT TAT GCT GCC TTT CCA TTA CCT AGC AGA ACC TCC TTC AAT GAC        138
His Tyr Ala Ala Phe Pro Leu Pro Ser Arg Thr Ser Phe Asn Asp
         25                  30                      35
```

| | | | | | | | | | | | | | | |
|---|---|---|---|---|---|---|---|---|---|---|---|---|---|---|
| TCC | CTC | ACA | TTC | TTA | GAG | AAT | GCT | GCA | GAC | GTT | GGG | GGG | CTA | GCC | 183
| Ser | Leu | Thr | Phe | Leu | Glu | Asn | Ala | Ala | Asp | Val | Gly | Gly | Leu | Ala |
| | 40 | | | | | 45 | | | | | 50 | | | |

| | | | | | | | |
|---|---|---|---|---|---|---|---|
| ATC | GCG | CTG | CAG | GTATGCAAGT | GTCAAGGGCC | ACAGT | 220
| Ile | Ala | Leu | Gln | | | |
| | | | 55 | | | |

(2) INFORMATION FOR SEQ ID NO:54:

(i) SEQUENCE CHARACTERISTICS:
        (A) LENGTH: 146 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:54:

| | | | | | | | | | | |
|---|---|---|---|---|---|---|---|---|---|---|
| CCCTTCTCTA | CCCACCCCTA | CCCAG | GCA | TAC | AGC | AAG | AGG | CTG | TTA | CGG | 49
| | | | Ala | Tyr | Ser | Lys | Arg | Leu | Leu | Arg |
| | | | 1 | | | | 5 | | | |

| | | | | | | | | | | | | |
|---|---|---|---|---|---|---|---|---|---|---|---|---|
| CAC | CAT | GGG | GAG | ACT | GTC | CTG | CCC | AGC | CTG | GAC | CTC | AGC | CCC | CAG | 94
| His | His | Gly | Glu | Thr | Val | Leu | Pro | Ser | Leu | Asp | Leu | Ser | Pro | Gln |
| | 10 | | | | | 15 | | | | | 20 | | | |

| | | | | | | | | | |
|---|---|---|---|---|---|---|---|---|---|
| CAG | ATC | TTC | TTT | CGA | AGC | TAT | GCC | CAG | GTAGGCAGCG | GCCACCTCCC | 141
| Gln | Ile | Phe | Phe | Arg | Ser | Tyr | Ala | Gln | | |
| | 25 | | | | | 30 | | | | |

GCCAC          146

(2) INFORMATION FOR SEQ ID NO:55:

(i) SEQUENCE CHARACTERISTICS:
        (A) LENGTH: 313 nucleotides
        (B) TYPE: nucleic acid
        (C) STRANDEDNESS: single
        (D) TOPOLOGY: linear (ii) MOLECULE TYPE: genomic DNA (iii) HYPOTHETICAL: no (xi) SEQUENCE DESCRIPTION: SEQ ID NO:55:

| | | | | | | | | | |
|---|---|---|---|---|---|---|---|---|---|
| TTCAATAACC | TCTCTTCCTG | CTCAG | GTG | ATG | TGT | AGG | AAG | CCC | AGC | CCC | 49
| | | | Val | Met | Cys | Arg | Lys | Pro | Ser | Pro |
| | | | 1 | | | | 5 | | | |

| | | | | | | | | | | | | | | |
|---|---|---|---|---|---|---|---|---|---|---|---|---|---|---|
| CAG | GAC | TCT | CAC | GAC | ACT | CAC | AGC | CCT | CCA | CAC | CTC | CGA | GTC | CAC | 94
| Gln | Asp | Ser | His | Asp | Thr | His | Ser | Pro | Pro | His | Leu | Arg | Val | His |
| | 10 | | | | | 15 | | | | | 20 | | | |

| | | | | | | | | | | | | | | |
|---|---|---|---|---|---|---|---|---|---|---|---|---|---|---|
| GGG | CCC | CTC | AGC | AGC | ACC | CCA | GCC | TTT | GCC | AGG | TAT | TTC | CGC | TGT | 139
| Gly | Pro | Leu | Ser | Ser | Thr | Pro | Ala | Phe | Ala | Arg | Tyr | Phe | Arg | Cys |
| | 25 | | | | | 30 | | | | | 35 | | | |

| | | | | | | | | | | | | | | |
|---|---|---|---|---|---|---|---|---|---|---|---|---|---|---|
| GCA | CGT | GGT | GCT | CTC | TTG | AAC | CCC | TCC | AGC | CGC | TGC | CAG | CTC | TGG | 184
| Ala | Arg | Gly | Ala | Leu | Leu | Asn | Pro | Ser | Ser | Arg | Cys | Gln | Leu | Trp |
| | 40 | | | | | 45 | | | | | 50 | | | |

| | | | | |
|---|---|---|---|---|
| TAACTTGGTT | ACCAAAGATG | CCACAGCACA | GAAATATCGA | CCAACACCTC | 234
| CCTGGTCACA | TCCATGGAAT | CAGAGCAAGA | TTTCCTTTCT | GCTTCTGTTC | 284
| CAAAAATAAA | AGCTGGCACT | TGGCTTCCG | | | 313

(2) INFORMATION FOR SEQ ID NO:56:

(i) SEQUENCE CHARACTERISTICS:
        (A) LENGTH: 327 nucleotides ( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( x i ) SEQUENCE DESCRIPTION: SEQ ID NO:56:

| | | | | | |
|---|---|---|---|---|---|
| GTCACAGTGC | AAGACAAAAG | GAGCAGACCA | AGGGCAAGAT | TGCTTGGGGA | 50 |
| GTGAAGACTC | CCTCCCTCTT | CTCCCCTGAG | AAGCTGAGAT | AAAGGGGGAG | 100 |
| GAGAAGCCTG | GGTGCCCCCC | ACTGATAAGC | AGGCTCCACC | CAGAGGCCAG | 150 |
| TCCTGTGTGT | CTGGGGACAA | GGCGAAAGAG | CAGCAGAAGT | GCCCCTTCTC | 200 |
| CAGGATCAAG | GAACTGGGGC | GGGGGGTGTT | TCCTGGACCC | CAGTCCTCCG | 250 |
| AATCAGCTCC | TAGAGTGGAA | CCAGGAAGGA | TTCTGGAGCC | ACAGAAGATA | 300 |
| GACAGAGTGT | AAGTCCCCTT | TTGGAGT | | | 327 |

( 2 ) INFORMATION FOR SEQ ID NO:57:

( i ) SEQUENCE CHARACTERISTICS:
( A ) LENGTH: 45 nucleotides
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( x i ) SEQUENCE DESCRIPTION: SEQ ID NO:57:

```
TGG ACT TCC TTA AAC TTT AAC CGA ACG CTG AGA CTT CTG ATG AGT      45
Trp Thr Ser Leu Asn Phe Asn Arg Thr Leu Arg Leu Leu Met Ser
1               5                   10                  15
```

( 2 ) INFORMATION FOR SEQ ID NO:58:

( i ) SEQUENCE CHARACTERISTICS:
( A ) LENGTH: 45 nucleotides
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( x i ) SEQUENCE DESCRIPTION: SEQ ID NO:58:

```
TGG ACT TCC TTA AAC TTT AAC CGA ATG CTG AGA CTT CTG ATG AGT      45
Trp Thr Ser Leu Asn Phe Asn Arg Met Leu Arg Leu Leu Met Ser
1               5                   10                  15
```

( 2 ) INFORMATION FOR SEQ ID NO:59:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( v ) FRAGMENT TYPE: internal fragment ( x i ) SEQUENCE DESCRIPTION: SEQ ID NO:59:

```
His Glu Leu Leu His
1               5
```

( 2 ) INFORMATION FOR SEQ ID NO:60:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
        ( A ) NAME/KEY: variable residues
        ( B ) LOCATION: 3-4
        ( C ) OTHER INFORMATION: /note= "consensus sequence found
            in active sites of zinc neutral peptidases"

( x i ) SEQUENCE DESCRIPTION: SEQ ID NO:60:

```
His  Glu  Xaa  Xaa  His
1                   5
```

( 2 ) INFORMATION FOR SEQ ID NO:61:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:61:

```
ATACTGACTC ATCAGAAGTG TCAGCA                                   26
```

( 2 ) INFORMATION FOR SEQ ID NO:62:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:62:

```
TTAGTCCTCA CTCNCCATGC TTCC                                     24
```

( 2 ) INFORMATION FOR SEQ ID NO:63:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO:63:

```
TCACACAGGT GTCCTCTCTT CC                                       22
```

( 2 ) INFORMATION FOR SEQ ID NO:64:

( i ) SEQUENCE CHARACTERISTICS:
        ( A ) LENGTH: 24 nucleotides
        ( B ) TYPE: nucleic acid
        ( C ) STRANDEDNESS: single -continued (D) TOPOLOGY: linear (i i) MOLECULE TYPE: genomic DNA (i i i) HYPOTHETICAL: no (x i) SEQUENCE DESCRIPTION: SEQ ID NO:64:

CTCACCTAGG CAGCACCAAC CCTA                    24

(2) INFORMATION FOR SEQ ID NO:65:

(i) SEQUENCE CHARACTERISTICS:
    (A) LENGTH: 25 nucleotides
    (B) TYPE: nucleic acid
    (C) STRANDEDNESS: single
    (D) TOPOLOGY: linear (i i) MOLECULE TYPE: genomic DNA (i i i) HYPOTHETICAL: no (x i) SEQUENCE DESCRIPTION: SEQ ID NO:65:

TTACCTGGAG GGCATGGTTG TCACT                   25